(12) United States Patent
Bullington et al.

(10) Patent No.: US 11,259,727 B2
(45) Date of Patent: Mar. 1, 2022

(54) STERILE BODILY-FLUID COLLECTION DEVICE AND METHODS

(71) Applicant: Magnolia Medical Technologies, Inc., Seattle, WA (US)

(72) Inventors: Gregory J. Bullington, Seattle, WA (US); Richard G. Patton, Seattle, WA (US); Shan E. Gaw, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 229 days.

(21) Appl. No.: 16/274,835

(22) Filed: Feb. 13, 2019

(65) Prior Publication Data

US 2019/0175085 A1    Jun. 13, 2019

Related U.S. Application Data

(63) Continuation of application No. 14/096,826, filed on Dec. 4, 2013, now Pat. No. 10,251,590.
(Continued)

(51) Int. Cl.
*A61B 5/157*  (2006.01)
*A61B 10/00*  (2006.01)
(Continued)

(52) U.S. Cl.
CPC .............. *A61B 5/157* (2013.01); *A61B 5/154* (2013.01); *A61B 5/150221* (2013.01);
(Continued)

(58) Field of Classification Search
CPC .............. A61B 5/157; A61B 5/150221; A61B 5/150992; A61B 5/154; A61B 10/0045; A61B 5/15003; A61B 5/155
See application file for complete search history.

(56) References Cited

U.S. PATENT DOCUMENTS 2,707,953 A   5/1955  Ryan
2,992,974 A   7/1961  Belcove et al.
(Continued)

FOREIGN PATENT DOCUMENTS

CN    2907683 Y    6/2007
CN    102548524 A    7/2012
(Continued)

OTHER PUBLICATIONS

Office Action for Canadian Application No. 2,932,536, dated Nov. 8, 2019, 6 pages.
(Continued)

*Primary Examiner* — Patrick Fernandes
(74) *Attorney, Agent, or Firm* — Cooley LLP

(57) ABSTRACT

An apparatus includes a pre-sample reservoir, a diversion mechanism, and a flow metering mechanism. The diversion mechanism has an inlet port couplable to a lumen-defining device to receive bodily-fluids from a patient, a first outlet port fluidically couplable to the pre-sample reservoir, and a second outlet port fluidically couplable to a sample reservoir. The diversion mechanism defines a first fluid flow path and a second flow path that are configured to place the first outlet port and the second outlet port, respectively, in fluid communication with the inlet port. The flow metering mechanism is configured to meter a flow of a predetermined volume of bodily-fluid through the first fluid flow path into the pre-sample reservoir, to meter a flow of a second volume of bodily-fluid through the second fluid flow path into the sample reservoir, and to display a volumetric indicator associated with the predetermined volume and the second volume.

17 Claims, 28 Drawing Sheets

Related U.S. Application Data

(60) Provisional application No. 61/733,199, filed on Dec. 4, 2012.

(51) Int. Cl.
  *A61B 5/15* (2006.01)
  *A61B 5/154* (2006.01)
  *A61B 5/155* (2006.01)

(52) U.S. Cl.
  CPC .... *A61B 5/150992* (2013.01); *A61B 10/0045* (2013.01); *A61B 5/15003* (2013.01); *A61B 5/155* (2013.01)

(56) References Cited

U.S. PATENT DOCUMENTS

| | | | |
|---|---|---|---|
| 3,013,557 | A | 12/1961 | Pallotta |
| 3,098,016 | A | 7/1963 | Cooper et al. |
| 3,382,865 | A | 5/1968 | Worral, Jr. |
| 3,405,706 | A | 10/1968 | Cinqualbre |
| 3,467,095 | A | 9/1969 | Ross |
| 3,494,351 | A | 2/1970 | Horn |
| 3,494,352 | A | 2/1970 | Russo et al. |
| 3,577,980 | A | 5/1971 | Cohen |
| 3,604,410 | A | 9/1971 | Whitacre |
| 3,635,798 | A | 1/1972 | Kirkham et al. |
| 3,648,684 | A | 3/1972 | Barnwell et al. |
| 3,741,197 | A | 6/1973 | Sanz et al. |
| 3,777,773 | A | 12/1973 | Tolbert |
| 3,817,240 | A | 6/1974 | Ayres |
| 3,834,372 | A | 9/1974 | Turney |
| 3,835,835 | A | 9/1974 | Thompson et al. |
| 3,848,579 | A | 11/1974 | Villa-Real |
| 3,848,581 | A * | 11/1974 | Cinqualbre ...... A61B 5/150236 600/575 |
| 3,874,367 | A | 4/1975 | Ayres |
| 3,886,930 | A | 6/1975 | Ryan |
| 3,890,203 | A | 6/1975 | Mehl |
| 3,890,968 | A | 6/1975 | Pierce et al. |
| 3,937,211 | A | 2/1976 | Merten |
| 3,945,380 | A | 5/1976 | Dabney et al. |
| 3,960,139 | A | 6/1976 | Bailey |
| 3,978,846 | A | 9/1976 | Bailey |
| 4,056,101 | A | 11/1977 | Geissler et al. |
| 4,057,050 | A | 11/1977 | Sarstedt |
| 4,063,460 | A | 12/1977 | Svensson |
| 4,077,395 | A | 3/1978 | Woolner |
| 4,106,497 | A | 8/1978 | Percarpio |
| 4,133,863 | A | 1/1979 | Koenig |
| 4,150,089 | A | 4/1979 | Linet |
| 4,154,229 | A | 5/1979 | Nugent |
| 4,166,450 | A | 9/1979 | Abramson |
| 4,193,400 | A | 3/1980 | Loveless et al. |
| 4,207,870 | A | 6/1980 | Eldridge |
| 4,212,308 | A | 7/1980 | Percarpio |
| 4,257,416 | A | 3/1981 | Prager |
| 4,275,730 | A | 6/1981 | Hussein |
| 4,340,067 | A | 7/1982 | Rattenborg |
| 4,340,068 | A | 7/1982 | Kaufman |
| 4,349,035 | A | 9/1982 | Thomas et al. |
| 4,370,987 | A | 2/1983 | Bazell et al. |
| 4,398,544 | A | 8/1983 | Nugent et al. |
| 4,412,548 | A | 11/1983 | Hoch |
| 4,416,290 | A | 11/1983 | Lutkowski |
| 4,425,235 | A | 1/1984 | Cornell et al. |
| 4,444,203 | A | 4/1984 | Engelman |
| 4,459,997 | A | 7/1984 | Sarstedt |
| 4,509,534 | A | 4/1985 | Tassin, Jr. |
| 4,608,996 | A | 9/1986 | Brown |
| 4,654,027 | A | 3/1987 | Dragan et al. |
| 4,657,027 | A | 4/1987 | Paulsen |
| 4,657,160 | A | 4/1987 | Woods et al. |
| 4,673,386 | A | 6/1987 | Gordon |
| 4,676,256 | A | 6/1987 | Golden |
| 4,679,571 | A | 7/1987 | Frankel et al. |
| 4,705,497 | A | 10/1987 | Shitaokoshi et al. |
| 4,714,461 | A | 12/1987 | Gabel |
| 4,772,273 | A | 9/1988 | Alchas |
| 4,865,583 | A | 9/1989 | Tu |
| 4,886,072 | A | 12/1989 | Percarpio et al. |
| 4,890,627 | A | 1/1990 | Haber et al. |
| 4,904,240 | A | 2/1990 | Hoover |
| 4,988,339 | A | 1/1991 | Vadher |
| 5,027,827 | A | 7/1991 | Cody et al. |
| 5,032,116 | A | 7/1991 | Peterson et al. |
| 5,045,185 | A | 9/1991 | Ohnaka et al. |
| 5,066,284 | A | 11/1991 | Mersch et al. |
| 5,084,034 | A | 1/1992 | Zanotti |
| 5,097,842 | A | 3/1992 | Bonn |
| 5,100,394 | A | 3/1992 | Dudar et al. |
| 5,108,927 | A | 4/1992 | Dom |
| 5,116,323 | A | 5/1992 | Kreuzer et al. |
| 5,122,129 | A | 6/1992 | Olson et al. |
| 5,135,489 | A | 8/1992 | Jepson et al. |
| 5,222,502 | A | 6/1993 | Kurose |
| 5,269,317 | A | 12/1993 | Bennett |
| 5,330,464 | A | 7/1994 | Mathias et al. |
| 5,417,673 | A | 5/1995 | Gordon |
| 5,431,811 | A | 7/1995 | Tusini et al. |
| 5,439,450 | A | 8/1995 | Haedt |
| 5,450,856 | A | 9/1995 | Norris |
| 5,466,228 | A | 11/1995 | Evans |
| 5,485,854 | A | 1/1996 | Hollister |
| 5,507,299 | A | 4/1996 | Roland |
| 5,520,193 | A | 5/1996 | Suzuki et al. |
| 5,575,777 | A | 11/1996 | Cover et al. |
| 5,603,700 | A | 2/1997 | Daneshvar |
| 5,632,906 | A | 5/1997 | Ishida et al. |
| 5,691,486 | A | 11/1997 | Behringer et al. |
| 5,749,857 | A | 5/1998 | Cuppy |
| 5,762,633 | A | 6/1998 | Whisson |
| 5,772,608 | A | 6/1998 | Dhas |
| 5,811,658 | A | 9/1998 | Van Driel et al. |
| 5,824,001 | A | 10/1998 | Erskine |
| 5,865,812 | A | 2/1999 | Correia |
| 5,871,699 | A | 2/1999 | Ruggeri |
| 5,911,705 | A | 6/1999 | Howell |
| 5,922,551 | A | 7/1999 | Durbin et al. |
| 5,961,472 | A | 10/1999 | Swendson et al. |
| 5,971,956 | A | 10/1999 | Epstein |
| 5,980,830 | A | 11/1999 | Savage et al. |
| 6,106,509 | A | 8/2000 | Loubser |
| 6,210,909 | B1 | 4/2001 | Guirguis |
| 6,224,561 | B1 | 5/2001 | Swendson et al. |
| 6,328,726 | B1 | 12/2001 | Ishida et al. |
| 6,364,890 | B1 | 4/2002 | Lum et al. |
| 6,387,086 | B2 | 5/2002 | Mathias et al. |
| 6,403,381 | B1 | 6/2002 | Mann et al. |
| 6,478,775 | B1 | 11/2002 | Galt et al. |
| 6,506,182 | B2 | 1/2003 | Estabrook et al. |
| 6,520,948 | B1 | 2/2003 | Mathias et al. |
| 6,569,117 | B1 | 5/2003 | Ziv et al. |
| 6,626,884 | B1 | 9/2003 | Dillon et al. |
| 6,638,252 | B2 | 10/2003 | Moulton et al. |
| 6,648,835 | B1 | 11/2003 | Shemesh |
| 6,692,479 | B2 | 2/2004 | Kraus et al. |
| 6,695,004 | B1 | 2/2004 | Raybuck |
| 6,716,187 | B1 | 4/2004 | Jorgensen et al. |
| 6,733,433 | B1 | 5/2004 | Fell |
| 6,736,783 | B2 | 5/2004 | Blake et al. |
| 6,746,420 | B1 | 6/2004 | Prestidge et al. |
| 6,843,775 | B2 | 1/2005 | Hyun |
| 6,860,871 | B2 | 3/2005 | Kuracina et al. |
| 6,905,483 | B2 | 6/2005 | Newby et al. |
| 6,913,580 | B2 | 7/2005 | Stone |
| 6,945,948 | B2 | 9/2005 | Bainbridge et al. |
| 7,044,941 | B2 | 5/2006 | Mathias et al. |
| 7,052,603 | B2 | 5/2006 | Schick |
| 7,055,401 | B2 | 6/2006 | Prybella et al. |
| 7,087,047 | B2 | 8/2006 | Kraus et al. |
| 7,241,281 | B2 | 7/2007 | Coelho et al. |
| 7,306,736 | B2 | 12/2007 | Collins et al. |
| 7,335,188 | B2 | 2/2008 | Graf |
| 7,384,416 | B2 | 6/2008 | Goudaliez et al. |

(56) References Cited

U.S. PATENT DOCUMENTS

| | | |
|---|---|---|
| 7,461,671 B2 | 12/2008 | Ehwald et al. |
| 7,479,131 B2 | 1/2009 | Mathias et al. |
| 7,614,857 B2 | 11/2009 | Fuechslin et al. |
| 7,615,033 B2 | 11/2009 | Leong |
| 7,666,166 B1 | 2/2010 | Emmert et al. |
| 7,744,573 B2 | 6/2010 | Gordon et al. |
| 7,766,879 B2 | 8/2010 | Tan et al. |
| 8,070,725 B2 | 12/2011 | Christensen |
| 8,197,420 B2 | 6/2012 | Patton |
| 8,349,254 B2 | 1/2013 | Hoshino et al. |
| 8,377,040 B2 | 2/2013 | Burkholz et al. |
| 8,383,044 B2 | 2/2013 | Davis et al. |
| 8,412,300 B2 | 4/2013 | Sonderegger |
| 8,523,826 B2 | 9/2013 | Layton, Jr. |
| 8,535,241 B2 | 9/2013 | Bullington et al. |
| 8,540,663 B2 | 9/2013 | Davey et al. |
| 8,568,371 B2 | 10/2013 | Slopes et al. |
| 8,574,203 B2 | 11/2013 | Stout et al. |
| 8,603,009 B2 | 12/2013 | Tan et al. |
| 8,795,198 B2 | 8/2014 | Tan et al. |
| 8,827,958 B2 | 9/2014 | Bierman et al. |
| 8,864,684 B2 | 10/2014 | Bullington et al. |
| 9,060,724 B2 | 6/2015 | Bullington et al. |
| 9,138,572 B2 | 9/2015 | Zeytoonian et al. |
| 9,155,495 B2 | 10/2015 | Bullington et al. |
| 9,204,864 B2 | 12/2015 | Bullington et al. |
| 9,314,201 B2 | 4/2016 | Burkholz et al. |
| 9,855,386 B2 | 1/2018 | Close et al. |
| 9,877,675 B2 | 1/2018 | Baid |
| 9,895,092 B2 | 2/2018 | Burkholz |
| 9,950,084 B2 | 4/2018 | Bullington et al. |
| 10,251,590 B2 | 4/2019 | Bullington et al. |
| 10,772,548 B2 | 9/2020 | Bullington et al. |
| 2001/0039058 A1 | 11/2001 | Iheme et al. |
| 2002/0002349 A1 | 1/2002 | Flaherty et al. |
| 2002/0004647 A1 | 1/2002 | Leong |
| 2002/0183651 A1 | 12/2002 | Hyun |
| 2002/0193751 A1 | 12/2002 | Theeuwes et al. |
| 2003/0013991 A1 | 1/2003 | Stone |
| 2003/0055381 A1 | 3/2003 | Wilkinson |
| 2003/0069543 A1 | 4/2003 | Carpenter et al. |
| 2003/0105414 A1 | 6/2003 | Leong |
| 2003/0208151 A1 | 11/2003 | Kraus et al. |
| 2004/0009542 A1 | 1/2004 | Dumont et al. |
| 2004/0010228 A1 | 1/2004 | Swenson et al. |
| 2004/0054283 A1 | 3/2004 | Corey et al. |
| 2004/0054333 A1 | 3/2004 | Theeuwes et al. |
| 2004/0127816 A1 | 7/2004 | Galvao |
| 2004/0147855 A1 | 7/2004 | Marsden |
| 2005/0004524 A1 | 1/2005 | Newby et al. |
| 2005/0148993 A1 | 7/2005 | Mathias et al. |
| 2005/0161112 A1 | 7/2005 | Ehwald et al. |
| 2005/0199077 A1 | 9/2005 | Prybella et al. |
| 2005/0240161 A1 | 10/2005 | Crawford |
| 2005/0245885 A1 | 11/2005 | Brown |
| 2005/0273019 A1 | 12/2005 | Conway et al. |
| 2005/0281713 A1 | 12/2005 | Hampsch et al. |
| 2006/0251622 A1 | 11/2006 | Suzuki et al. |
| 2006/0287639 A1 | 12/2006 | Sharp |
| 2007/0088279 A1 | 4/2007 | Shue et al. |
| 2007/0100250 A1 | 5/2007 | Kline |
| 2007/0119508 A1 | 5/2007 | West et al. |
| 2007/0287948 A1 | 12/2007 | Sakiewicz |
| 2008/0086085 A1 | 4/2008 | Brown |
| 2008/0108954 A1 | 5/2008 | Mathias et al. |
| 2008/0145933 A1 | 6/2008 | Patton |
| 2008/0167577 A1 | 7/2008 | Weilbacher et al. |
| 2008/0185056 A1 | 8/2008 | Diodati et al. |
| 2008/0254471 A1* | 10/2008 | Bordano .................. A01N 1/02 435/6.18 |
| 2008/0319346 A1 | 12/2008 | Crawford et al. |
| 2009/0050213 A1 | 2/2009 | Biddell et al. |
| 2009/0192447 A1 | 7/2009 | Andersen et al. |
| 2009/0306601 A1 | 12/2009 | Shaw et al. |
| 2010/0010372 A1 | 1/2010 | Brown et al. |
| 2010/0042048 A1 | 2/2010 | Christensen |
| 2010/0057004 A1 | 3/2010 | Christensen et al. |
| 2010/0094171 A1 | 4/2010 | Conway et al. |
| 2010/0152681 A1 | 6/2010 | Mathias |
| 2010/0268118 A1 | 10/2010 | Schweiger |
| 2011/0306899 A1 | 12/2011 | Brown et al. |
| 2012/0035540 A1 | 2/2012 | Ferren et al. |
| 2012/0265099 A1 | 10/2012 | Goodnow, II et al. |
| 2012/0265128 A1 | 10/2012 | Kolln |
| 2014/0066880 A1 | 3/2014 | Prince et al. |
| 2015/0018715 A1 | 1/2015 | Walterspiel |
| 2016/0113560 A1 | 4/2016 | Bullington et al. |
| 2016/0174888 A1 | 6/2016 | Berthier et al. |
| 2016/0361006 A1 | 12/2016 | Bullington et al. |

FOREIGN PATENT DOCUMENTS

| | | |
|---|---|---|
| CN | 102971040 A | 3/2013 |
| CN | 103477201 A | 12/2013 |
| DE | 2 203 858 B2 | 5/1973 |
| DE | 2 541 494 A1 | 3/1977 |
| DE | 299 13 417 U1 | 12/2000 |
| DE | 100 38 026 A1 | 2/2001 |
| DE | 102 43 129 A1 | 4/2004 |
| EP | 0 448 795 | 10/1991 |
| WO | WO 1986/005568 | 9/1986 |
| WO | WO 1991/018632 | 12/1991 |
| WO | WO 1992/016144 | 10/1992 |
| WO | WO 1997/018845 | 5/1997 |
| WO | WO 2000/041624 | 7/2000 |
| WO | WO 2001/008546 | 2/2001 |
| WO | WO 2003/008012 | 1/2003 |
| WO | WO 2003/047660 | 6/2003 |
| WO | WO 2003/078964 | 9/2003 |
| WO | WO 2005/068011 | 7/2005 |
| WO | WO 2006/031500 | 3/2006 |
| WO | WO 2007/033319 | 3/2007 |
| WO | WO 2008/101025 | 8/2008 |
| WO | WO 2011/069145 | 6/2011 |
| WO | WO 2012/012127 | 1/2012 |
| WO | WO 2014/089186 | 6/2014 |
| WO | WO 2016/054252 | 4/2016 |

OTHER PUBLICATIONS

Office Action for Canadian Application No. 2,932,536, dated Oct. 23, 2020, 6 pages.

Extended European Search Report for EP Application No. 19190772. 4, dated Feb. 10, 2020, 7 pages.

Notice of Reasons for Rejection for Japanese Application No. 2018-086721, dated Mar. 15, 2019, 6 pages.

Notice of Reasons for Rejection for Japanese Application No. 2019-230734, dated Jan. 22, 2021, 9 pages.

Barnard, D. R. & Arthur, M. M., "Fibronectin (cold insoluble globulin) in the neonate," Clinical and Laboratory Observations, 102(3): 453-455 (1983).

Baxter, "IV Tubing and Access Devices" authored by and published by Baxter, dated Nov. 6, 2006, 105 pages.

BD Saf-T-Intima Closed IV Catheter System, Becton, Dickinson and Company, 2015 Brochure. Retrieved from the Internet (Sep. 11, 2019) <https://www.bd.com/en-us/offerings/capabilities/infusion-therapy/iv-catheters/bd-saf-tintima-closed-iv-catheter-system>, 2 pages.

BD Vacutainer Passive Shielding Blood Collection Needle Brochure; Becton Dickinson and Company (2005), 2 pages.

Brecher, M. E. et al., "Bacterial Contamination of Blood Components," Clinical Microbiology Reviews, 18(1):195-204 (2005).

Cartridge and Test Information, Abbott, Art: 714258-01O Rev. Date: Aug. 15, 2016, 6 pages.

Challiner, A. et al., Queen Alexandra Hospital, Portsmouth P06 3LY, "Venous/arterial blood management protection system," Correspondence, p. 169.

De Korte, D. et al., "Diversion of first blood volume results in a reduction of bacterial contamination for whole-blood collections," Vox Sanguinis, 83:13-16 (2002).

(56) References Cited

OTHER PUBLICATIONS

De Korte, D. et al., "Effects of skin disinfection method, deviation bag, and bacterial screening on clinical safety of platelet transfusions in the Netherlands," Transfusion, 46: 476-485 (2006).
Edwards Lifesciences, "Conservation. Safety. Simplicity. Edwards VAMP and VAMP Jr. Systems," 2002 Brochure. Retrieved from the Internet (Sep. 11, 2019) <https://www.medline.com/media/catalog/Docs/MKT/VAMPSYSTEMBROCHURE.PDF>, 4 pages.
Ernst, D. J. et al., "NCCLS simplifies the order of draw: a brief history," MLO, 26-27 (2004).
Gottlieb, T., "Hazards of Bacterial Contamination of Blood Products," Anaesth Intens Care, 21: 20-23 (1993).
Hillyer, C. D. et al., "Bacterial Contamination of Blood Components Risks, Strategies, and Regulation," Hematology, 575-589 (2003).
Li, Y. et al., "Direct labeling and visualization of blood vessels with lipophilic carbocyanine dye DiI," Nature Protocols, 3(11): 1703-1708 (2008).
Liumbruno, G. M. et al., "Reduction of the risk of bacterial contamination of blood components through diversion of the first part of the donation of blood and blood components," Blood Transfus, 7: 86-93 (2009).
Mayer, G. A., "A Method for the Reliable Determination of Clotting Time in Whole Blood," Can Med Assoc J., 72(12): 927-929 (1955).
McDonald, C. P., "Interventions Implemented to Reduce the Risk of Transmission of Bacteria by Transfusion in the English National Blood Service," Transfus Med Hemother, 38:255-258 (2011).
Meissner, G. F. et al., "A Method Based on the Use of Whole Venous Blood in Capillary Tubes," American Journal of Clinical Pathology, 33(2): 29-31 (1963).
Murphy, M., "Better Blood Transfusion," Journal of the Intensive Core Society, 4(3): 78-80 (2003).
Napolitano, M. et al., "Quality control of bacterial contamination of blood components: the feasibility of diversion system testing," Blood Transfus, 2: 231-232 (2004).
Norberg, A. et al., "Contamination Rates of Blood Cultures Obtained by Dedicated Phlebotomy vs Intravenous Catheter," JAMA, 289(6): 726-729 (2003).
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Pall Corp., "Leukotrap Filtration Systems for Whole Blood Derived Platelets: Leukotrap RC PL and Leukotrap PL Systems," 2005 Brochure, 2 pages.
Perez, P. et al., "Multivariate analysis of determinants of bacterial contamination of whole-blood donations," Vox Sanguinis, 82:55-60 (2002).
Quilici, N. et al., "Differential Quantitative Blood Cultures in the Diagnosis of Catheter-Related Sepsis in Intensive Care Units," Clinical Infectious Diseases 25:1066-1070 (1997).
Sheppard, C. A. et al., "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1): 11-19 (2000).
Tang, M. et al., "Closed Blood Conservation Device for Reducing Catheter-Related Infections in Children After Cardiac Surgery," Critical Care Nurse, 34(5): 53-61 (2014).
Wang, P. et al., "Strategies on Reducing Blood Culture Contamination," Reviews in Medical Microbiology, 23:63-66 (2012).
Weinbaum, F. I. et al., "Doing It Right the First Time: Quality Improvement and the Contaminant Blood Culture," Journal of Clinical Microbiology, 35(3): 563-565 (1997).
Weinstein, M. P., "Current Blood Culture Methods and Systems: Clinical Concepts, Technology, and Interpretation of Results," Clinical Infectious Diseases, 23: 40-46 (1996).
Weinstein, M. P., "Minireview: Blood Culture Contamination: Persisting Problems and Partial Progress," Journal of Clinical Microbiology, 41(6): 2275-2278 (2003).
Weinstein, M. P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Ziegler, et al., "Controlled Clinical Laboratory Comparison of Two Supplemented Aerobic and Anaerobic Media Used in Automated Blood Culture Systems To Detect Bloodstream Infections," J. Clinical Microbiology, 36(3):657-661 (1998).
Zimmon, D. S. et al., "Effect of Portal Venous Blood Flow Diversion on Portal Pressure," J Clin Invest, 65(6): 1388-1397 (1980).
Zundert, A. V., "New Closed IV Catheter System," Acta Anaesth. Belg., 56: 283-285 (2005).
Office Action for U.S. Appl. No. 14/096,826, dated Jul. 26, 2017, 12 pages.
Office Action for U.S. Appl. No. 14/096,826, dated Mar. 8, 2018, 14 pages.
Office Action for U.S. Appl. No. 14/728,318, dated May 19, 2017, 26 pages.
Office Action for U.S. Appl. No. 14/728,318, dated Jan. 8, 2018, 36 pages.
Office Action for U.S. Appl. No. 14/728,318, dated Dec. 20, 2018, 26 pages.
Office Action for U.S. Appl. No. 14/728,318, dated Jul. 18, 2019, 27 pages.
Notification of the First Office Action for Chinese Application No. 201380072185.0, dated Sep. 28, 2016, 17 pages.
Supplementary European Search Report for EP Application No. 13860741.1, dated Jun. 7, 2016, 5 pages.
Extended European Search Report for EP Application No. 17204012.3, dated Feb. 14, 2018, 7 pages.
International Search Report and Written Opinion for International Application No. PCT/US2013/073080, dated Feb. 18, 2014, 14 pages.
Notice of Reasons for Rejection for Japanese Application No. 2015-545813, dated Jul. 4, 2017, 14 pages.
Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.
BD Medical Surgical Systems Catalogue (Canadian Version), BD Medical, 2010, 51 pages.
Calam, R. R., "Recommended 'Order of Draw' for Collecting Blood Specimens Into Additive-Containing Tubes," Letter to the Editor, Clinical Chemistry, 28(6): 1399 (1982), 1 page.
Hall, K. K. et al., "Updated Review of Blood Culture Contamination," Clinical Microbiology Reviews, 19(4):788-802 (2006).
Kim, J. Y. et al., "The Sum of the Parts is Greater Than the Whole: Reducing Blood Culture Contamination," Annals of Internal Medicine, 154:202-203 (2011).
Levin, P. D. et al., "Use of the Nonwire Central Line Hub to Reduce Blood Culture Contamination," Chest, 143(3):640-645 (2013).
Order of Draw for Multiple Tube Collections, LabNotes, a newsletter from BD Diagnostics,—Preanalytical Systems, 17(1):3 (2007).
Patton, R. G. et al., "Innovation for Reducing Blood Culture Contamination: Initial Specimen Diversion Technique," Journal of Clinical Microbiology, 48(12):4501-4503 (2010).
Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.
Schuur, J., "Blood Cultures: When Do they Help and When Do They Harm?" Brigham & Women's Hospital, Department of Emergency Medicine, (June 21-23, 2012), 42 pages.
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Stohl, S. et al., "Blood Cultures at Central Line Insertion in the Intensive Care Unit: Comparison with Peripheral Venipuncture," Journal of Clinical Microbiology, 49(7):2398-2403 (2011).

(56) References Cited

OTHER PUBLICATIONS

Wagner et al., "Diversion of Initial Blood Flow to Prevent Whole-Blood Contamination by Skin Surface Bacteria: an in vitro model," Transfusion, 40:335-338 (2000).

\* cited by examiner

STERILE BODILY-FLUID COLLECTION DEVICE AND METHODS

CROSS-REFERENCE TO RELATED APPLICATIONS

This application is a continuation of U.S. patent application Ser. No. 14/096,826, entitled "Sterile Bodily-Fluid Collection Device and Methods," filed Dec. 4, 2013, which claims priority to and the benefit of U.S. Provisional Patent Application Ser. No. 61/733,199, entitled "Sterile Bodily-Fluid Collection Device and Methods," filed Dec. 4, 2012, the disclosures of which are incorporated herein by reference in their entireties.

BACKGROUND

Embodiments described herein relate generally to the parenteral procurement of bodily-fluid samples, and more particularly to devices and methods for parenterally-procuring bodily-fluid samples with reduced contamination from microbes or other contaminants exterior to the bodily-fluid source, such as dermally-residing microbes.

Health care practitioners routinely perform various types of microbial tests on patients using parenterally-obtained bodily-fluids. In some instances, patient samples (e.g., bodily-fluids) are tested for the presence of one or more potentially undesirable microbes, such as bacteria, fungi, or yeast (e.g., Candida). Microbial testing may include incubating patient samples in one or more sterile vessels containing culture media that is conducive to microbial growth, real-time diagnostics, and/or molecular PCR-based approaches. Generally, when such microbes are present in the patient sample, the microbes flourish over time in the culture medium. After a variable amount of time (e.g., a few hours to several days), organism growth can be detected by automated, continuous monitoring. Such automated monitoring can detect carbon dioxide produced by organism growth. The culture medium can then be tested for the presence of the microbes. The presence of microbes in the culture medium suggests the presence of the same microbes in the patient sample which, in turn, suggests the presence of the same microbes in the bodily-fluid of the patient from which the sample was obtained. Accordingly, when microbes are determined to be present in the culture medium, the patient may be prescribed one or more antibiotics or other treatments specifically designed to treat or otherwise remove the undesired microbes from the patient.

Patient samples, however, can become contaminated during procurement and/or can be otherwise susceptible to false positive results. One way in which contamination of a patient sample may occur is by the transfer of microbes from a bodily surface (e.g., dermally-residing microbes) dislodged during needle insertion into a patient and subsequently transferred to a culture medium with the patient sample. The bodily surface and/or other undesirable external microbes may be dislodged either directly or via dislodged tissue fragments, hair follicles, sweat glands and other skin adnexal structures. Another possible source of contamination is from the person drawing the patient sample. For example, a doctor, phlebotomist, nurse, etc. can transfer contaminants from their body (e.g., finger, arms, etc.) to the patient sample and/or to the equipment containing the patient sample. Expanding further, equipment and/or devices used during a patient sample procurement process (e.g., patient to needle, needle/tubing to sample vessels, etc.) often include multiple fluidic interfaces that can each introduce points of potential contamination. The use of such equipment and/or devices typically includes manual intervention to connect and/or fluidically couple various interfaces. Since these interfaces are not preassembled and sterilized as a single fluidically coupled system, external contaminants can be introduced to the patient sample via the user (e.g., doctor, phlebotomist, etc.) and/or other sources (e.g. ambient air, contaminants on surfaces of tables and counters in patient room, microbes transferred from linens or clothing, etc.). In some instances, such contaminants may thrive in a culture medium and eventually yield a positive microbial test result, thereby falsely indicating the presence of such microbes in vivo.

In some instances, false positive results and/or false negative results can be attributed to a specific volume of the patient sample. For example, overfilling of volume-sensitive blood culture bottles can lead to false positive results as noted in the instructions for use and/or warning labeling from manufacturers of such culture bottles, as well as associated automated continuous monitoring microbial detection systems. On the other hand, as another example, insufficient patient sample volume within a culture medium can result in false negative results. By way of example, in a study performed by the Mayo Clinic entitled, "Optimized Pathogen Detection with 30- Compared to 20-Milliliter Blood Culture Draws," published in the December 2011 issue of Journal of Clinical Microbiology, a patient sample volume of 20 milliliters (mL) can result in detection of about 80% of bacteremias present in a patient sample, a patient sample volume of 40 mL can result in detection of about 88% of the bacteremias, and a patient sample volume of 60 mL can result in detection of about 99% of the bacteremias.

Such inaccurate results as a result of contamination, insufficient patient sample volume, and/or the like are a concern when attempting to diagnose or treat a suspected illness or condition. For example, false negative results from microbial tests may result in a misdiagnosis and/or delayed treatment of a patient illness which, in some cases, could result in the death of the patient. Conversely, false positive results from microbial tests may result in the patient being unnecessarily subjected to one or more anti-microbial therapies, which may cause serious side effects to the patient including, for example, death, as well as produce an unnecessary burden and expense to the health care system due to extended length of patient stay and/or other complications associated with erroneous treatments. Additionally, the use of diagnostic imaging equipment attributable to these false positive results is also a concern from both a cost as well as patient safety perspective as unnecessary exposure to concentrated radiation associated with a variety of imaging procedures (e.g., CT scans) has many known adverse impacts on long-term patient health.

As such, a need exists for sterile "all-in-one" bodily-fluid collection devices and methods that reduce microbial contamination in bodily-fluid test samples by, for example, minimizing exposure of the patient sample and/or fluidic interfaces to ambient non-sterile conditions and/or other sources of external contamination. Additionally, a need exists for such bodily-fluid collection devices to include a means for accurately metering, measuring, and/or otherwise assessing and confirming a volume of bodily-fluid transferred from a patient to a sample reservoir or culture medium that can be visually, tactically, or otherwise communicated to a healthcare practitioner procuring the patient sample in substantially real-time (e.g. at the patient bedside).

SUMMARY

Devices for parenterally-procuring bodily-fluid samples with reduced contamination from microbes exterior to the bodily-fluid source, such as dermally-residing microbes and/or other undesirable external contaminants, are described herein. In some embodiments, an apparatus for obtaining a bodily fluid sample from a patient includes a pre-sample reservoir, a diversion mechanism, and a flow metering mechanism. The pre-sample reservoir is configured to receive a first volume of bodily-fluid withdrawn from the patient. The diversion mechanism includes an inlet port, a first outlet port, and a second outlet port, and defines a first fluid flow path and a second fluid flow path. The inlet port can be coupled to a lumen-defining device for receiving bodily-fluids from the patient. The first outlet port and the second outlet port are configured to fluidically couple the pre-sample reservoir and a sample reservoir, respectively, to the diversion mechanism. The first fluid flow path is configured to place the first outlet port in fluid communication with the inlet port and a second fluid flow path configured to place the second outlet port in fluid communication with the inlet port. The flow metering mechanism is in fluid communication with the first fluid flow path and the second fluid flow path. The flow metering mechanism is configured to meter a flow of the first volume of bodily-fluid through the first fluid flow path into the pre-sample reservoir and to meter a flow of a second volume of bodily-fluid through the second fluid flow path into the sample reservoir. The flow metering mechanism is configured to display a volumetric indicator associated with the first volume and the second volume.

DETAILED DESCRIPTION

Figure 1:
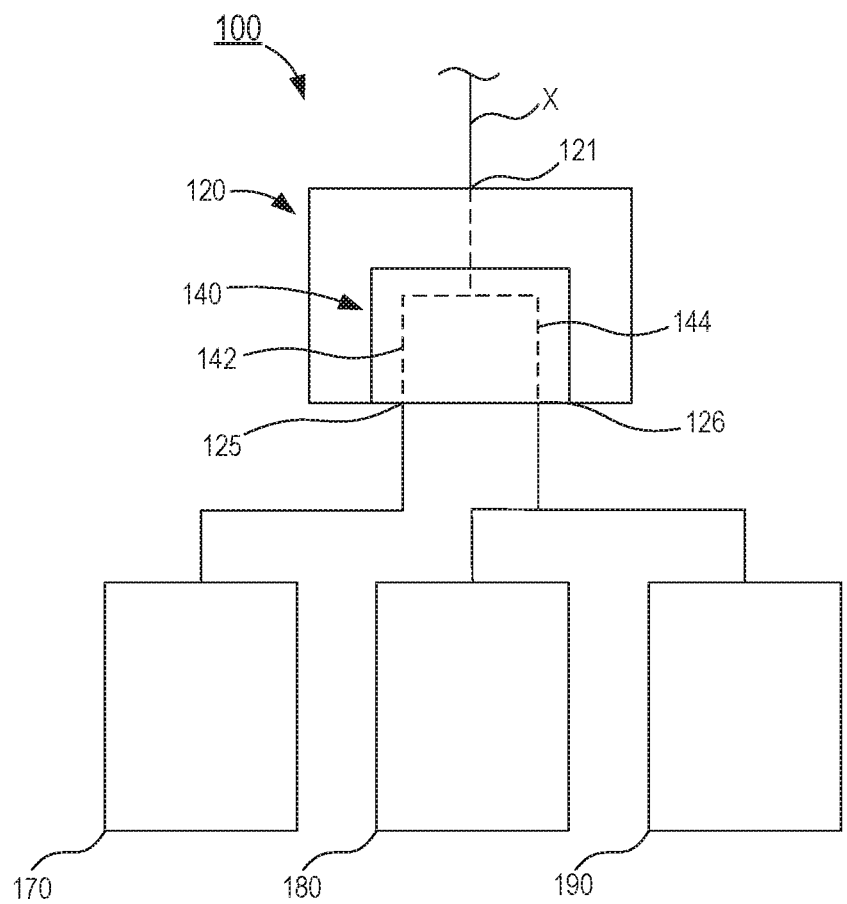
FIG. 1 is a schematic illustration of a bodily-fluid collection device according to an embodiment.

Devices for parenterally-procuring bodily-fluid samples with reduced contamination from microbes exterior to the bodily-fluid source, such as dermally-residing microbes and/or other undesirable external contaminants, are described herein. In some embodiments, an apparatus for obtaining a bodily fluid sample from a patient includes a pre-sample reservoir, a diversion mechanism, and a flow metering mechanism. The pre-sample reservoir is configured to receive a first volume of bodily-fluid withdrawn from the patient. The diversion mechanism includes an inlet port, a first outlet port, and a second outlet port, and defines a first fluid flow path and a second fluid flow path. The inlet port can be coupled to a lumen-defining device for receiving bodily-fluids from the patient. The first outlet port and the second outlet port are configured to fluidically couple the pre-sample reservoir and a sample reservoir, respectively, to the diversion mechanism. The first fluid flow path is configured to place the first outlet port in fluid communication with the inlet port and a second fluid flow path configured to place the second outlet port in fluid communication with the inlet port. The flow metering mechanism is in fluid communication with the first fluid flow path and the second fluid flow path. The flow metering mechanism is configured to meter a flow of the first volume of bodily-fluid through the first fluid flow path into the pre-sample reservoir and to meter a flow of a second volume of bodily-fluid through the second fluid flow path into the sample reservoir. The flow metering mechanism is configured to display a volumetric indicator associated with the first volume and the second volume.

In some embodiments, an apparatus for obtaining a bodily-fluid sample from a patient includes a pre-sample reservoir, a diversion mechanism, a flow controller, and a movable member. The pre-sample reservoir is configured to receive a first volume of bodily-fluid withdrawn from the patient. The diversion mechanism includes an inlet port, a first outlet port, and a second outlet port. The inlet port is couplable to a lumen-defining device for receiving bodily-fluids from the patient. The first outlet port fluidically couples the pre-sample reservoir to the diversion mechanism and the second outlet port fluidically couples a sample reservoir to the diversion mechanism. The flow controller is at least partially disposed within the diversion mechanism and can be moved between a first configuration, in which the flow controller defines at least a portion of a fluid flow path between the inlet port and the first outlet port, and a second configuration, in which the flow controller defines at least a portion of a fluid flow path between the inlet port and the second outlet port. The movable member movably coupled to the diversion mechanism and movable through the second outlet port between a first configuration, in which the sample reservoir is fluidically isolated from the fluid flow path between the inlet port and the second outlet port, and a second configuration, in which the sample reservoir is in fluid communication with the fluid flow path between the inlet port and the second outlet port. The sample reservoir is configured to receive a second volume of bodily-fluid withdrawn from the patient when the flow controller is in its second configuration and the movable member is in its second configuration.

In some embodiments, an apparatus for obtaining a bodily-fluid sample from a patient includes a pre-sample, reservoir, a diversion mechanism, and a flow controller. The pre-sample reservoir is configured to receive a first volume of bodily-fluid withdrawn from the patient. The diversion mechanism includes a housing and a distribution member. The housing defines a first aperture in fluid communication with the pre-sample reservoir and a second aperture. The distribution member is at least partially disposed within the housing and defines a fluid flow channel in fluid communication with the second aperture. The distribution member includes a coupling portion that is in fluid communication with the flow channel and is configured to be physically and fluidically coupled to a sample reservoir. The flow controller includes an inlet port couplable to a lumen-defining device for receiving bodily-fluids from the patient. The flow controller is rotatably coupled to the diversion mechanism and movable between a first configuration, in which the inlet port is in fluid communication with the first aperture, and a second configuration, in which the inlet port is in fluid communication with the second aperture.

In some embodiments, a method of using a flow-metering transfer device having a diversion mechanism with an inlet port configured to be selectively placed in fluid communication with a pre-sample reservoir and a sample reservoir, and a flow-metering mechanism configured to meter a flow of bodily-fluid from the patient to the pre-sample reservoir and to the sample reservoir includes establishing fluid communication between the patient and the inlet port of the flow-metering transfer device. Fluid communication is then established between the port and the pre-sample reservoir. A flow of bodily-fluid transferred from the patient to the pre-sample reservoir is metered. The method includes verifying a pre-sample volume of bodily-fluid disposed in the pre-sample reservoir is a first pre-sample volume of bodily-fluid via the flow-metering mechanism of the flow-metering transfer device. With the pre-sample volume disposed in the pre-sample reservoir, the pre-sample reservoir is fluidically isolated from the port to sequester the pre-sample volume of bodily-fluid in the pre-sample reservoir. With the pre-sample reservoir fluidically isolated, the method includes establishing fluid communication between the port and the sample reservoir. A flow of bodily-fluid transferred from the patient to the sample reservoir is metered. The method includes verifying a sample volume of bodily-fluid disposed in the sample reservoir is a first sample volume of bodily-fluid via the flow-metering mechanism of the flow-metering transfer device.

In some embodiments, an apparatus includes a diversion mechanism and a flow controller. The diversion mechanism can define an inlet port, a first outlet port, a second outlet port, and a third outlet port. The first outlet port is fluidically coupled to a pre-sample reservoir, the second outlet port is fluidically coupled to a first sample reservoir, and the third outlet port is fluidically coupled to a second sample reservoir, and so forth. All of the fluid reservoirs can be fluidically isolated from each other. The flow controller includes various fluidic channels that can allow fluidic movement in specified directions and can be configured to be operably coupled to the diversion mechanism. In use, when the diversion mechanism is at a first configuration, the flow controller can allow a flow of bodily-fluid to enter the pre-sample reservoir. The diversion mechanism can be moved to a second configuration, where the flow controller can allow a flow of bodily-fluid to enter the first sample reservoir. Additionally, the diversion mechanism can then be moved to a third configuration, whereby the flow controller can allow a flow of bodily-fluid to enter the second sample reservoir.

In some embodiments, a bodily-fluid collection device can be configured to selectively divert a first, predetermined volume of a bodily-fluid to a pre-sample reservoir before permitting the flow of a second volume of the bodily-fluid into a first sample reservoir and/or a third volume of the bodily-fluid into a second sample reservoir. In this manner, the second and/or third volumes of bodily-fluid can be used for diagnostic or other testing, while the first volume of bodily-fluid, which may contain microbes from a bodily surface or other source external to the patient from which the sample is procured, is isolated. In some embodiments, the bodily-fluid collection device can include additional sample reservoirs (e.g., 3, 4, 5, 6 or more) depending on the analysis and/or testing protocols to be performed.

In some embodiments, a bodily-fluid collection device can include flow metering to ensure the proper volume of bodily-fluid is collected from a patient and/or transferred into a specific pre-sample and/or sample reservoir. The bodily-fluid collection device can be configured to automatically divert and/or control the fluid flow after metered volumes of bodily-fluid are collected. For example, after a first metered pre-sample volume is collected, a diversion mechanism can be configured to divert the bodily-fluid flow to a first sample reservoir and then after a first metered sample volume is collected, the diversion mechanism can be configured to divert the bodily-fluid flow to a second sample reservoir and so on. In some embodiments, the bodily-fluid collection device can include a metered volume display such as, for example, a liquid crystal display (LCD), to provide a visual indication to the user of how much bodily-fluid has been collected into each specific, individual sample reservoir. In some embodiments, multiple displays can be provided to allow for customized pre-sample and/or sample volume collection.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the terms "first, predetermined amount," "first amount," and "first volume" describe an amount of bodily-fluid configured to be received or contained by a first reservoir or a pre-sample reservoir. While the terms "first amount" and "first volume" do not explicitly describe a predetermined amount, it should be understood that the first amount is the first, predetermined amount unless explicitly described differently.

As used herein, the terms "second amount" and "second volume" describe an amount of bodily-fluid configured to be received or contained by a second reservoir or sample reservoir. The second amount can be any suitable amount of bodily-fluid and need not be predetermined. Conversely, when explicitly described as such, the second amount received and contained by the second reservoir or sample reservoir can be a second, predetermined amount.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used herein, the terms "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "about," "approximately," and "substantially" when used in connection with a numerical value is intended to convey that the value so defined is nominally the value stated. Said another way, the terms about, approximately, and substantially when used in connection with a numerical value generally include the value stated plus or minus a given tolerance. For example, in some instances, a suitable tolerance can be plus or minus 10% of the value stated; thus, about 0.5 would include 0.45 and 0.55, about 10 would include 9 to 11, about 1000 would include 900 to 1100. In other instances, a suitable tolerance can be plus or minus an acceptable percentage of the last significant figure in the value stated. For example, a suitable tolerance can be plus or minus 10% of the last significant figure; thus, about 10.1 would include 10.09 and 10.11, approximately 25 would include 24.5 and 25.5. Such variance can result from manufacturing tolerances or other practical considerations (such as, for example, tolerances associated with a measuring instrument, acceptable human error, or the like).

When describing a relationship between a predetermined volume of bodily-fluid and a collected volume of bodily-fluid it is to be understood that the values include a suitable tolerance such as those described above. For example, when stating that a collected volume of bodily-fluid is substantially equal to a predetermined volume of bodily-fluid, the collected volume and the predetermined volume are nominally equal within a suitable tolerance. In some instances, the tolerances can be determined by the intended use of the collected volume of bodily-fluid. For example, in some instances, an assay of a blood culture can be about 99% accurate when the collected volume of blood is within 1.0% to 5.0% of the manufacturer's (or evidence-based best practices) recommended volume. By way of an example, a manufacturer's recommended volume for an assay of a bodily-fluid can be 10 milliliters (mL) per sample collection bottle, with a total of four or six collection bottles used (i.e., an aggregate volume of 40 ml to 60 ml) plus or minus 5% for about 99% confidence. Thus, a collected volume of 10.5 mL would provide results with over about 99% confidence, while a collected volume of 11 mL would provide results with less than about 99% confidence. In other instances, a suitable tolerance can be 0.1%, 0.5%, 1.0%, 2.0%, 3.0%, 4.0%, 5.0%, 6.0%, 7.0%, 8.0%, 9.0%, 10.0%, or any fraction of a percent therebetween. In still other instances, a tolerance can be greater than 10.0%. Thus, any of the embodiments described herein can include and/or can be used in conjunction with any suitable flow-metering mechanism and/or device that is configured to meter a flow and/or otherwise measure a volume of bodily-fluid within a suitable tolerance. Moreover, the flow-metering mechanism and/or device can be arranged such as to minimize or eliminate tolerance stacking that can result from a combination of inaccurate measurement, human error, and/or the like.

FIG. 1 is a schematic illustration of a portion of a bodily-fluid collection device 100, according to an embodiment. Generally, the bodily-fluid collection device 100 (also referred to herein as "fluid collection device" or "collection device") is configured to permit the withdrawal of bodily-fluid from a patient such that a first portion or volume of the withdrawn fluid is diverted away from a second and/or third portion or volume of the withdrawn fluid that is to be used as a biological sample, such as for testing for the purpose of medical diagnosis and/or treatment. In other words, the collection device 100 is configured to transfer a first, predetermined volume of a bodily-fluid to a pre-sample collection reservoir and a second and third volume (or, in some embodiments, a fourth, fifth and so on) of bodily-fluid to one or more sample collection reservoirs fluidically isolated from the pre-sample collection reservoir, as described in more detail herein.

The collection device 100 includes a diversion mechanism 120, a flow controller 140, a pre-sample reservoir 170, a first sample reservoir 180, and a second sample reservoir 190, different than the first sample reservoir 180. The diversion mechanism 120 includes an inlet port 121 and at least two outlet ports, such as a first outlet port 125, and a second outlet port 126 as shown in FIG. 1. In some embodiments, the diversion mechanism 120 can include a set of outlet ports equal to a total number of pre-sample reservoirs and sample reservoirs. For example, the diversion mechanism 120 can include five outlet ports when the collection device 100 has one pre-sample reservoir and four sample reservoirs. In some embodiments, the diversion mechanism 120 can be operatively coupled to an actuator (not shown in FIG. 1) which can facilitate the movement of the diversion mechanism 120 between multiple configurations. The inlet port 121 is configured to be fluidically coupled to a medical device defining a pathway X for withdrawing and/or conveying the bodily-fluid from the patient to the collection device 100. For example, the inlet port 121 can be fluidically coupled to a needle or other lumen-defining device (e.g., flexible sterile tubing). In this manner, the diversion mechanism 120 can receive the bodily-fluid from the patient via the needle or any other lumen-defining device.

The first outlet port 125 of the diversion mechanism 120 can be fluidically coupled to the pre-sample reservoir 170. In some embodiments, the pre-sample reservoir 170 is monolithically formed with the first outlet port 125 and/or a portion of the diversion mechanism 120. In other embodiments, the pre-sample reservoir 170 can be mechanically and/or fluidically coupled to the diversion mechanism 120 via an adhesive, a resistance fit, a mechanical fastener, any number of mating recesses, a threaded coupling, and/or any other suitable coupling or combination thereof. Similarly stated, the pre-sample reservoir 170 can be physically (e.g., mechanically) coupled to the diversion mechanism 120 such that an interior volume defined by the pre-sample reservoir 170 is in fluid communication with the first outlet port 125 of the diversion mechanism 120. In still other embodiments, the pre-sample reservoir 170 can be operably coupled to the first outlet port 125 of the diversion mechanism 120 via an intervening structure (not shown in FIG. 1), such as flexible sterile tubing. More particularly, the intervening structure can define a lumen configured to place the pre-sample reservoir 170 in fluid communication with the first outlet port 125.

The pre-sample reservoir 170 is configured to receive and contain the first, predetermined volume of the bodily-fluid. In some embodiments, the pre-sample reservoir 170 is configured to contain the first volume of the bodily-fluid such that the first volume is fluidically isolated from a second and/or third volume of the bodily-fluid (which can be the same or different than the first volume of bodily-fluid) that is subsequently withdrawn from the patient. The pre-sample reservoir 170 can be any suitable reservoir for containing a bodily-fluid, such as a pre-sample reservoir described in detail in U.S. Pat. No. 8,197,420 entitled, "Systems and Methods for Parenterally Procuring Bodily-Fluid Samples with Reduced Contamination," issued Jun. 12, 2012 (referred to henceforth as the "'420 patent"), the disclosure of which is incorporated herein by reference in its entirety.

In some embodiments, the second outlet port 126 of the diversion mechanism 120 is configured to be fluidically coupled to a lumen-defining device that can be coupled to the first sample reservoir 180 and the second sample reservoir 190. Optionally, in other embodiments, the second outlet port 126 of the diversion mechanism 120 can be coupled to the first sample reservoir 180 and the diversion mechanism 120 can have a third outlet port (not shown) coupled to the second sample reservoir 190. In some embodiments, the first sample reservoir 180 can be monolithically formed with the second outlet port 126 and/or a portion of the diversion mechanism 120. In other embodiments, the first sample reservoir 180 can be mechanically coupled to the second outlet port 126 or operably coupled to the second outlet port 126 via an intervening structure, such as described above with reference to the pre-sample reservoir 170. The first sample reservoir 180 is configured to receive and contain the second volume of the bodily-fluid. For example, the second volume of bodily-fluid can be an amount withdrawn from the patient subsequent to withdrawal of the first pre-sample volume. In some embodiments, the first sample reservoir 180 is configured to contain the second volume of the bodily-fluid in such a manner that the second volume is fluidically isolated from the first volume of the pre-sample bodily-fluid.

The first sample reservoir 180 and the second sample reservoir 190 can be any suitable sterile reservoir for containing a bodily-fluid including, for example, a sample reservoir as described in the '420 patent incorporated by reference above. In some embodiments, the second volume can be any suitable volume of bodily-fluid and need not be predetermined. In other embodiments, the transfer of the bodily-fluid to the first sample reservoir 180 and/or the second sample reservoir 190 can be metered or the like such that the second volume is a second predetermined volume.

The second sample reservoir 190 can be any suitable sample reservoir. In some embodiments, the second sample reservoir 190 can be substantially similar to the first sample reservoir 180 described above. The second sample reservoir 190 can be fluidically coupled to the second output port 126 as described above. The fluidic coupling of the second outlet port 126 to the second sample reservoir 190 can be substantially similar to the fluidic coupling of the second outlet port 126 to the first sample reservoir 180, as described in detail above. Therefore, such portions are not described in further detail herein and should be considered substantially similar unless explicitly described differently. Furthermore, additional outlet ports of the diversion mechanism 120 and sample reservoirs (not shown in FIG. 1) can be substantially similar to the second outlet port 126 and the first sample reservoir 180.

In some embodiments, the pre-sample reservoir 170, the first sample reservoir 180, and the second sample reservoir 190 can be coupled to (or formed with) the diversion mechanism 120 in a similar manner. In other embodiments, the pre-sample reservoir 170, the first sample reservoir 180, and the second sample reservoir 190 need not be similarly coupled to the diversion mechanism 120. For example, in some embodiments, the pre-sample reservoir 170 can be monolithically formed with the diversion mechanism 120 (e.g., the first outlet port 124) and the first sample reservoir 180 and/or the second sample reservoir 190 can be operably coupled to the diversion mechanism 120 (e.g., the second outlet port 126) via an intervening structure, such as a flexible sterile tubing or any combination thereof.

In some embodiments, the collection device 100 can further include an actuator (not shown in FIG. 1) and a flow controller 140 that defines a first fluid flow path 142, a second fluid flow path 144, and optionally additional fluid flow paths (not shown in FIG. 1). In some embodiments, the actuator can be included in or otherwise operably coupled to the diversion mechanism 120. In this manner, the actuator can be configured to control fluid movement within the flow controller 140 (e.g., between different configurations). For example, the actuator can be movable between a first position, corresponding to a first configuration of the flow controller 140, a second position, (different than the first position) corresponding to a second configuration of the flow controller 140, and so on. In some embodiments, the actuator can be configured for uni-directional movement. For example, the actuator can be moved from its first position to its second position, but cannot be moved from its second position to its first position. Similarly, the actuator can be moved from its second position to a third position, but cannot be moved from its third position back to its second position. In this manner, the flow controller 140 is prevented from being moved into its second or third configuration before its first configuration, thus requiring that the first amount of the bodily-fluid be directed to the pre-sample reservoir 170 and not the sample reservoirs 180 and/or 190 which is designed to contain the second and/or third volume of the withdrawn fluid that is to be used as a biological sample, such as for testing for the purpose of medical diagnosis and/or treatment.

The flow controller 140 is configured such that when in the first configuration, the first fluid flow path 142 fluidically couples the inlet port 121 to the first outlet port 125, and when in the second configuration, the second fluid flow path 144 fluidically couples the inlet port 121 to the second outlet port 126. In some embodiments, an actuator as described above can be configured to move the flow controller 140 in a translational motion between the first configuration, and the second configuration, and optionally a third or fourth configuration. For example, in some embodiments, the flow controller 140 can be in the first configuration when the flow controller 140 is in a distal position relative to the collection device 100. In such embodiments, the actuator can be actuated to move the flow controller 140 in the proximal direction to a proximal position relative to the collection device 100, thereby placing the flow controller 130 in the second configuration. In other embodiments, the actuator can also be actuated to move the flow controller 140 in a rotational motion between the first configuration and the second configuration or optionally a third or fourth configuration.

Accordingly, when the flow controller 140 is in the first configuration, the second outlet port 126 (and optionally additional outlet ports coupled to sample reservoirs) is fluidically isolated from the inlet port 121. Similarly, when the flow controller 140 is in the second configuration, the first outlet port 125 is fluidically isolated from the inlet port 121. And optionally, if the flow controller 140 is in a third configuration (not shown in FIG. 1), the first outlet port 125 and the second outlet port 126 are fluidically isolated from the inlet port 121. In this manner, the flow controller 140 can direct, or divert the first amount of the bodily-fluid to the pre-sample fluid reservoir 170 via the first outlet port 125 when the flow controller 140 is in the first configuration and can direct, or divert the second amount of the bodily-fluid to the first sample fluid reservoir 180 via the second outlet port 126 when the flow controller 140 is in the second configuration.

In some embodiments, at least a portion of the actuator can be operably coupled to the pre-sample fluid reservoir 170. In this manner, the actuator (or at least the portion of the actuator) can be configured to introduce or otherwise facilitate the development of a vacuum within the "pre-sample" fluid reservoir 170, thereby initiating flow of the bodily-fluid through the collection device 100 and into the pre-sample fluid reservoir 170 when the diversion mechanism 120 is in its first configuration. The actuator can include any suitable mechanism for actuating the flow of bodily-fluid into the collection device 100, such as, for example, a rotating disc, a plunger, a slide, a dial, a button, a handle, a lever, and/or any other suitable mechanism or combination thereof. Examples of suitable actuators are described in more detail herein with reference to specific embodiments.

In some embodiments, the diversion mechanism 120 can be configured such that the first amount of bodily-fluid need to be conveyed to the pre-sample fluid reservoir 170 before the diversion mechanism 120 will permit the flow of the second amount of bodily-fluid to be conveyed through the diversion mechanism 120 to the first sample fluid reservoir 180 and/or to the second sample fluid reservoir 190. In this manner, the diversion mechanism 120 can be characterized as requiring compliance by a health care practitioner regarding the collection of the first, predetermined amount (e.g., a pre-sample) prior to a collection of the second and/or third amount (e.g., a sample) of bodily-fluid. Similarly stated, the diversion mechanism 120 can be configured to prevent a health care practitioner from collecting the second amount, or the sample, of bodily-fluid into the first sample fluid reservoir 180 without first diverting the first amount, or pre-sample, of bodily-fluid to the pre-sample reservoir 170. In this manner, the health care practitioner is prevented from including (whether intentionally or unintentionally) the first amount of bodily-fluid, which is more likely to contain bodily surface microbes and/or other undesirable external contaminants, in the bodily-fluid sample to be used for analysis. In other embodiments, the fluid collection device 100 need not include a forced-compliance feature or component.

In some embodiments, the diversion mechanism 120 can have a fourth configuration (not shown in FIG. 1), different than the first, second, and third configurations. When in the fourth configuration, the diversion mechanism 120 can fluidically isolate the inlet port 121 from the first outlet port 125, the second outlet port 126, and optionally a third outlet port simultaneously. Therefore, when the diversion mechanism 120 is in its fourth configuration, flow of bodily-fluid from the inlet port 121 to the pre-sample fluid reservoir 170, the first sample fluid reservoir 180, and the second sample fluid reservoir 190 is prevented. In use, for example, the diversion mechanism 120 can be actuated (e.g., manually or automatically) to place the diversion mechanism 120 in the first configuration such that a bodily-fluid can flow from the inlet port 121 to the pre-sample fluid reservoir 170, then moved to the second configuration such that the bodily-fluid can flow from the inlet port 121 to the first sample fluid reservoir 180, and optionally moved to the third configuration such that the bodily-fluid can flow from the inlet port 121 to the second sample fluid reservoir 190, then moved to the fourth configuration to stop the flow of bodily-fluid into and/or through the diversion mechanism 120. In this manner, the device is effectively "locked" and self-contained in the fourth configuration such that any residual bodily-fluid in the device 100 is prevented from being communicated and/or otherwise exposing health care practitioner and/or patient to potential dangerous fluids. This optional safety feature can prevent potential exposure to bodily-fluid samples that can be infected with pathogens such as HIV, Hepatitis C, etc.

In some embodiments, one or more portions of the collection device 100 are disposed within a housing (not shown in FIG. 1). For example, in some embodiments, at least a portion of one or more of the diversion mechanism 120, the first pre-sample reservoir 170, and the sample reservoirs 180 and 190 can be disposed within the housing. In such an embodiment, at least a portion of the diversion mechanism 120 is accessible through the housing to allow the user to actuate the flow controller 140 to control the flow of bodily-fluid from the patient (e.g., a vein) to the collection device 100. Examples of suitable housings are described in more detail herein with reference to specific embodiments.

In some embodiments, the collection device 100 can optionally include one or more flow metering devices that can meter a flow of bodily-fluid through the collection device. For example, a flow metering device can be in fluid communication with the first fluid flow path 142 and/or the second fluid flow path 144 to meter a flow of bodily-fluid therethrough. In other embodiments, a flow metering device can be in fluid communication with and/or otherwise disposed in the first port 125 and/or the second port 126. The flow metering device can include an indicator or the like (e.g., a dial, a display, color, a haptic output device, an electrical signal output device such as a wireless radio signal, Bluetooth radio signal, etc.) that can be configured to provide an indication to a user that is associated with a predetermined volume being transferred to the pre-sample reservoir 170, the first sample reservoir 180, and/or the second sample reservoir 190. In some embodiments, the flow metering device can be operably coupled to, for example, an actuator or the like such as those described above. In such embodiments, the flow metering device can be operable in actuating the actuator to move the flow controller 140 between its first configuration and its second configuration based on a desired volume of bodily-fluid having flown through the flow metering device. Thus, the flow metering device can be used to ensure a desired volume of bodily-fluid is transferred to the pre-sample reservoir 170, the first sample reservoir 180, and/or the second sample reservoir 190, which in turn, can prevent insufficient, inaccurate and/or false results in, for example, microbial testing to the patient sample or the like.

Referring now to FIGS. 2-13, a collection device 200 includes a diversion mechanism 220, a flow controller 240, a pre-sample reservoir 270, a first sample reservoir 280, and a second sample reservoir 290, different than the first sample reservoir 280. As further described herein, the collection device 200 can be moved between a first, a second, and a third configuration to deliver a flow of a bodily-fluid that is substantially free from microbes exterior the body, such as, for example, dermally residing microbes and/or other undesirable external contaminants. The collection device 200 can be any suitable shape, size, or configuration. For example, while shown in FIGS. 2-13 with the sample reservoirs 280 and/or 290 as being oriented vertically with respect to the housing 201, the collection device 200 can have the sample reservoirs 280 and/or 290 oriented in a plane with respect to the housing 201, or conically disposed with respect to the housing 201, and/so forth.

Figure 2:
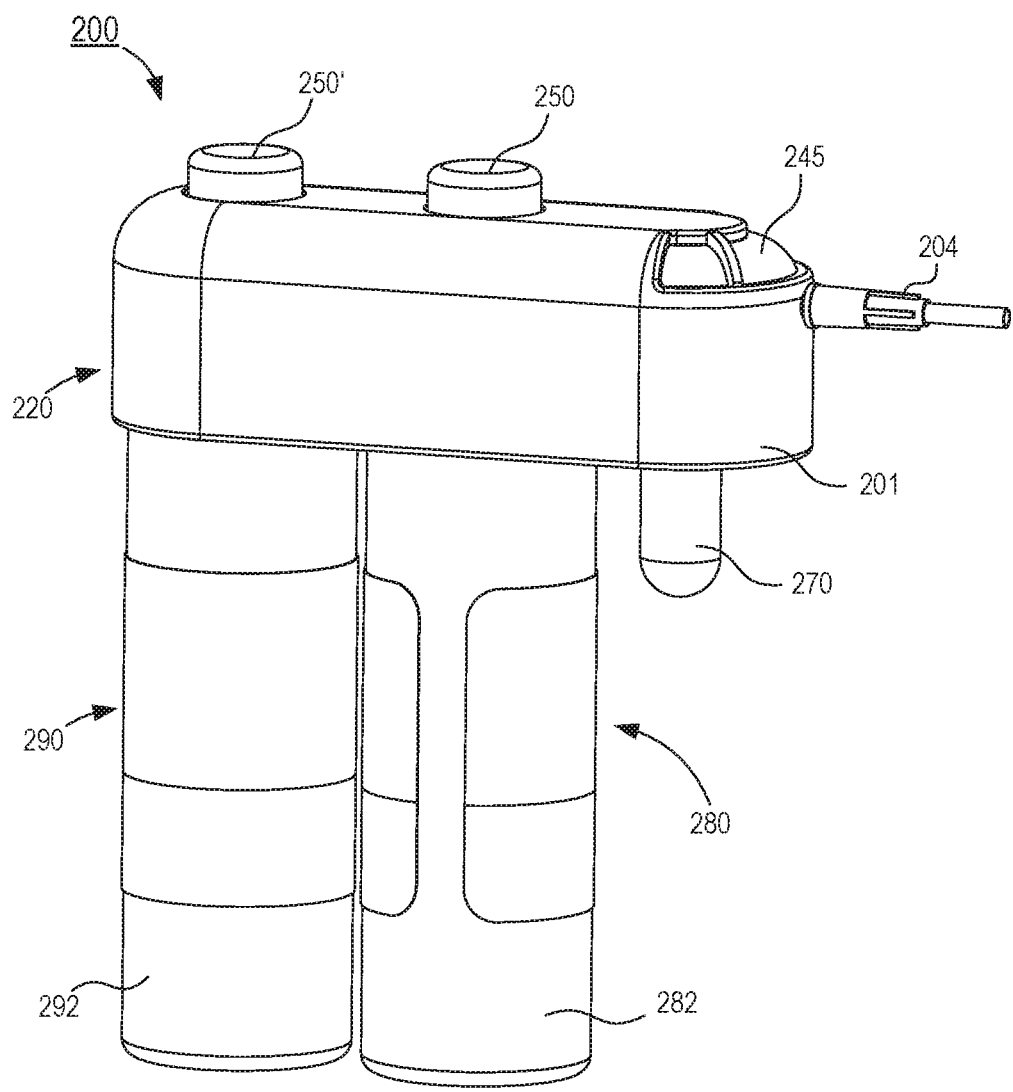
FIG. 2 is a perspective view of the bodily-fluid collection device according to an embodiment.
Figure 3:
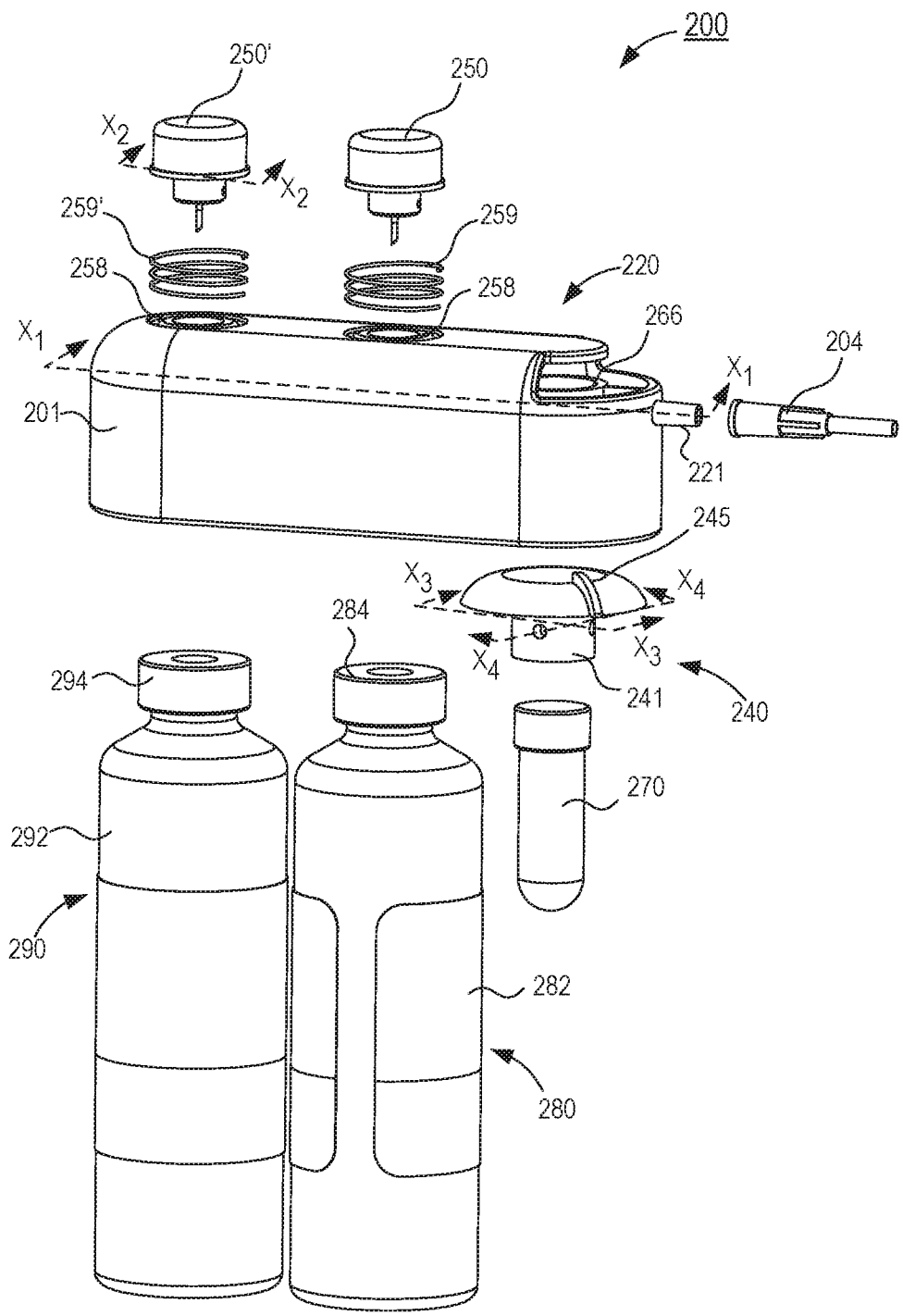
FIG. 3 is an exploded perspective view of the bodily-fluid collection device of FIG. 2.
Figure 4:
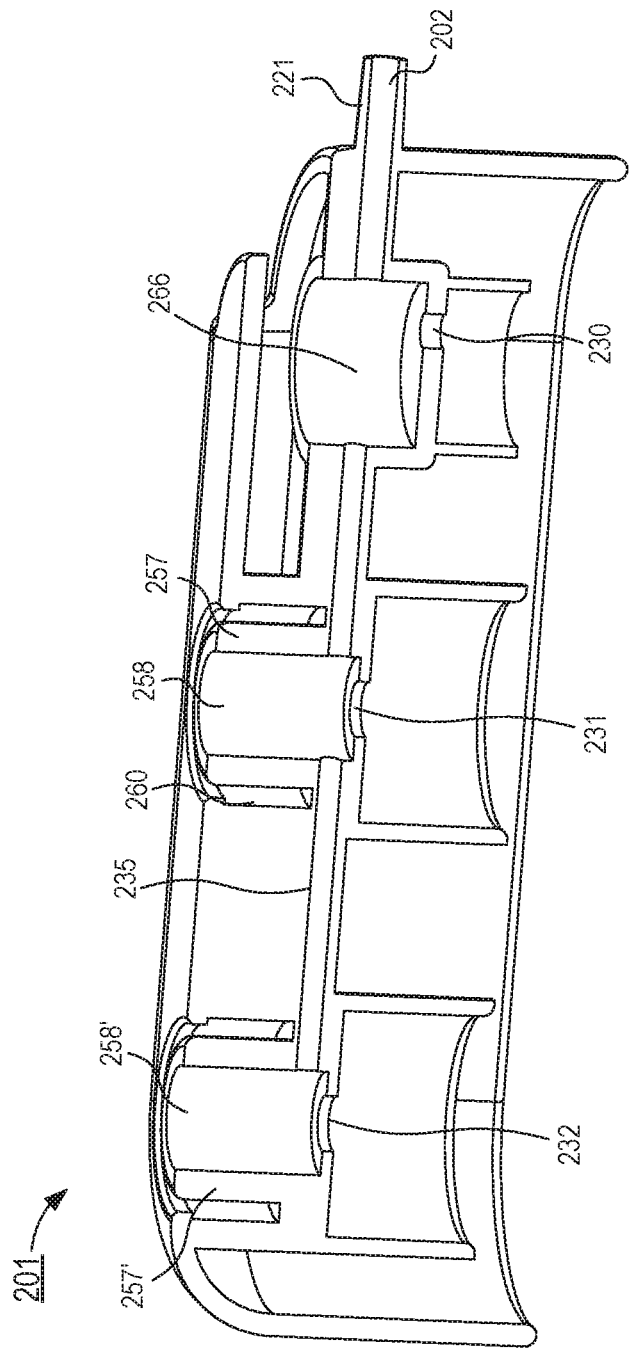
FIG. 4 is a cross-sectional side view of a housing included in the bodily-fluid collection device of FIG. 2, taken along the line $X_1$-$X_1$ in FIG. 3.

The diversion mechanism 220 includes a housing 201 and movable members 250 and 250'. As shown in FIGS. 2-4, the housing 201 is coupled to the pre-sample reservoir 270, the first sample reservoir 280, and the second sample reservoir 290. The housing 201 includes an inlet port 221, a first outlet port 230, a second outlet port 231, a third outlet port 232, and defines an inner flow channel 235 that can define a fluid flow path for collecting bodily-fluids from the patient. The inlet port 221 can be selectively placed in fluid communication with the inner flow channel 235. More specifically, the inlet port 221 defines an inlet lumen 202 that can be placed in fluid communication with the inner flow channel 235. In this manner, the inlet port 221 extends from a portion of the housing 201 such that the inner flow channel 235 can be placed in fluid communication with a volume substantially outside the housing 201, via the inlet lumen 202. The inlet port 221 can be fluidically coupled to a medical device (not shown) that defines a fluid flow pathway for withdrawing and/or conveying bodily-fluid from a patient to the collection device 200. For example, the inlet port 221 can be fluidically coupled to a needle or other lumen-defining device (e.g., flexible sterile tubing) either directly or indirectly via an adapter 204. Similarly stated, the inlet lumen 202 defined by the inlet port 221 is placed in fluid communication with a lumen defined by a lumen-defining device, when the lumen-defining device is coupled to the inlet port 221. Expanding further, when the lumen-defining device is disposed within a portion of a body of the patient (within a vein or the spinal cavity of a patient, for example), the inner flow channel 235 of the housing 201 can be placed in fluid communication with the portion of the body of the patient.

The inner flow channel 235 defined by the housing 201 is a central lumen that extends along a length of the housing 201 and that can be placed in fluid communication with the bodily-fluid of the patient following venipuncture (other method employed to gain access to bodily-fluid) as described herein. The inner flow channel 235 forms a fluid flow pathway for transferring bodily-fluid between the inlet port 221 and the first outlet port 230, the second outlet port 231, and the third outlet port 232. More specifically, when the inner flow channel 235 is placed in fluid communication with the patient (e.g., via the medical device coupled to the inlet port 221), the first outlet port 230, the second outlet port 231, and the third outlet port 232 can be selectively placed in fluid communication with the inner flow channel 235 to allow bodily-fluid to flow into at least one of the pre-sample reservoir 270, the first sample reservoir 280, or the second sample reservoir 290. In some embodiments, the bodily-fluid is prevented from flowing to the second outlet port 231 and the third outlet port 232 prior to a predetermined volume of bodily-fluid being collected in the pre-sample reservoir 270. In some embodiments, the second outlet port 231 and the third outlet port 232 can be placed in fluid communication with the inner flow channel 235 simultaneously. In some embodiments, the second outlet port 231 and the third outlet port 232 can be placed in fluid communication with the inner flow channel 235 sequentially.

Figure 5:
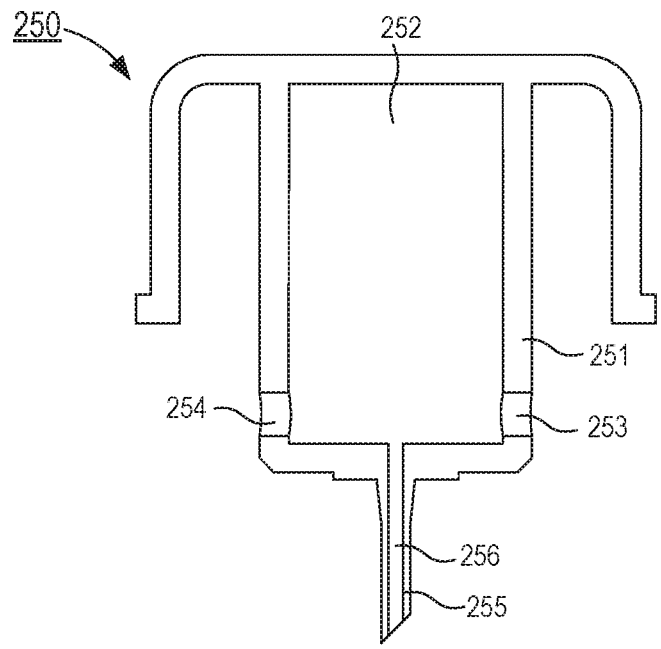
FIG. 5 is a cross-sectional view of a movable member included in the bodily-fluid collection device of FIG. 2, taken along the line $X_2$-$X_2$ in FIG. 3.

The movable members 250, 250' are configured to be actuated (e.g., moved) by the user from a first position and a second position relative to the housing 201 to direct fluid flow into the first sample reservoir 280 and the second sample reservoir 290. The movable members 250 and 250' are substantially the same and therefore are described with reference to a single movable member 250. As shown in FIG. 5, the movable member 250 includes a boss 251 that defines an inner cavity 252, an inlet port 253, a first outlet port 254, and a piercing member 255 that defines a lumen 256 fluidically coupled to the inner cavity 252. The inlet port 253 and the outlet port 254 extend through the walls of the boss 251 that defines the inner chamber 252 of the movable member 250. The movable member 250 is configured to be mounted on a support 257 of the housing 201 (see FIG. 4)

such that the boss 251 is disposed within a bore 258 (see FIG. 4) and at least a portion of the movable member 250 is received in an annular chamber 260. Optionally, a bias member 259 (e.g., a spring) can be disposed in the annular chamber 260 to return the movable member 250 back to its first position after being actuated by the user. In some embodiments, the movable member 250, the annular chamber 260, the bore 258 or the boss 251 can include mechanical locking features configured to hold the movable member 250 in the second position (e.g., a depressed position) after being actuated by the user.

As described herein, in the first configuration, the movable member 250 is disposed in a manner such that the movable member 250 is spaced apart from the inner flow channel 235. In such a configuration, no fluid flow path can be established between a part of the body of a patient (e.g., a vein, spinal cavity, etc.) and the sample reservoirs 280 and/or 290. Said another way, when in the movable member 250 is in its first configuration, the first sample reservoir 280 and the second sample reservoir 290 are fluidically isolated from the inner flow channel 235 defined by the housing 201. The movable member 250 can be actuated by the user to move the movable member 250 from the first configuration to the second configuration and into alignment with the inner flow channel 235. The force exerted by the user can be sufficient to deform (e.g., compress) the bias member 259, thereby allowing the piercing member 255 to be inserted into the sample reservoir 280 and/or 290. In the second configuration, the inlet port 253 and the outlet port 254 are substantially aligned with the inner flow channel 235 placing the inner cavity 252 in fluid communication with the inner flow channel 235. Thus, with the movable member 250 in the second configuration, a fluid flow pathway is established between the inner flow channel 235, the inner cavity 252, the lumen 256 of the piercing member 255, and the sample reservoir 280. Said another way, in such a configuration, bodily-fluid can flow from the patient (e.g., a vein, spinal cavity, etc.), through the diversion mechanism 220, and into the first sample reservoir 280 and/or the second sample reservoir 290 as described in greater detail herein.

The pre-sample reservoir 270 can be any suitable reservoir for containing a bodily-fluid such as, for example, single use disposable collection tubes, vacuum based collection tubes, and/or the like. The pre-sample reservoir 270 is configured to be fluidically coupled to the first outlet port 230 of the collection device 200 (either directly or via an intervening structure such as sterile flexible tubing) in any suitable manner. For example, in some embodiments, a portion of the pre-sample reservoir 270 can form a friction fit within a portion of the first outlet port 230. In other embodiments, the pre-sample reservoir 270 can be coupled to the first outlet port 230 via a threaded coupling, an adhesive, a snap fit, a mechanical fastener and/or any other suitable coupling method. In some embodiments, the pre-sample reservoir 270 can be monolithically formed with the housing 201. The pre-sample reservoir 270 can be configured to maintain negative pressure conditions (vacuum conditions) inside (the pre-sample reservoir 270) that can allow drawing of bodily-fluid from the inlet port 221 to the pre-sample reservoir 270 through outlet port 230 via vacuum suction. The pre-sample reservoir 270 is configured to contain the first amount of the bodily-fluid, where the first amount of bodily-fluid can be a predetermined or undetermined amount, such that the first amount of bodily-fluid is fluidically isolated from a second and/or third amount of the bodily-fluid that is subsequently withdrawn from the patient.

The sample reservoirs 280 and/or 290 can be any suitable reservoirs for containing a bodily-fluid, including, for example, single use disposable collection tubes, vacuum based collection tubes, a sample reservoir as described in the '420 patent incorporated by reference above, and/or the like. In some embodiments, sample reservoirs 280 and/or 290 can be substantially similar to or the same as known sample containers such as, for example, a Vacutainer®, or the like. The sample reservoir 280 and 290 include a sample container 282 and 292, respectively, and a vacuum seal 284 and 294, respectively. The vacuum seal 284 or 294 maintains negative pressure conditions (vacuum conditions) inside the sample container 282 or 292, respectively, that can allow drawing of bodily-fluid from the inner flow channel 235 to the sample container 282 or 292, respectively via vacuum suction. The sample reservoirs 280 and/or 290 can be configured to be fluidically coupled to the second outlet port 231 and third outlet port 232, respectively, of the collection device 200 (either directly or via an intervening structure such as sterile flexible tubing) in any suitable manner. The sample reservoirs 280 and/or 290 can be moved relative to the outlet ports 231 and/or 232 to place the sample reservoirs 280 and/or 290 in fluid communication with the outlet ports 231 and/or 232. The sample reservoirs 280 and 290 can be configured to contain a second or third amount of the bodily-fluid. The second or third amount of bodily-fluid can be a predetermined or undetermined amount, such that the second or third amount of bodily-fluid is fluidically isolated from the first amount of the bodily-fluid that is withdrawn from the patient. In some configurations, the sample reservoirs 280 and/or 290 can be coupled to the collection device 200 by being monolithically formed with the housing 201 in a manner similar to the pre-sample reservoir 270, thus, they are not described in detail herein. In some instances, the sample reservoirs 280 and/or 290 can be transparent such that the user can have visual feedback to confirm bodily-fluid flow into the sample reservoirs 280 and/or 290.

In some embodiments, the sample reservoirs 280 and 290 and the diversion mechanism 220 (and/or the portions of the collection device 200 other than the sample reservoirs 280 and 290) are independently formed (e.g., not monolithically formed) and coupled together during, for example, a manufacturing process. In some instances, the sample reservoirs 280 and 290 can be coupled to the diversion mechanism 220 in a substantially sterile or hermetic environment (e.g., an environment filled with ethylene oxide or the like). Thus, the interface between the sample reservoirs 280 and 290 and the diversion mechanism 220 is substantially sterilized prior to use. Moreover, the collection device 200 can be shipped and/or stored in a preassembled manner such as to maintain the substantially sterile interface between the sample reservoirs 280 and 290, and the diversion mechanism 220.

Figure 6:
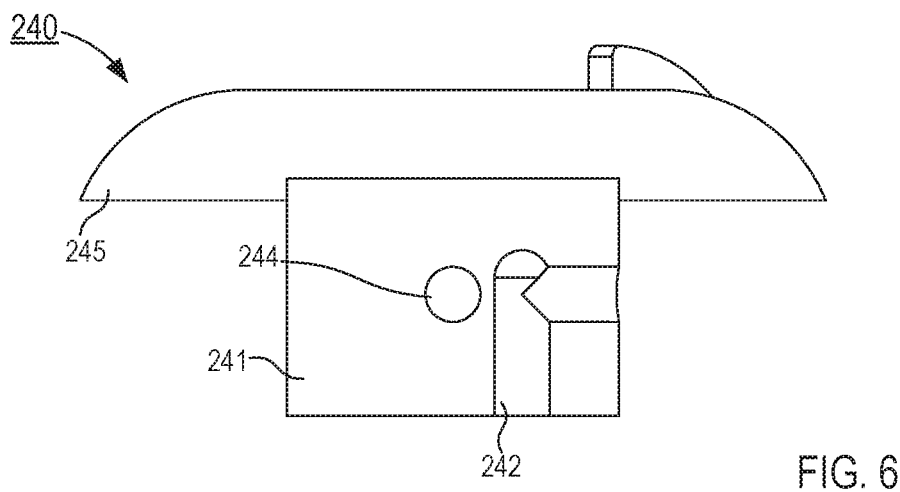
FIGS. 6 and 7 are cross-sectional views of a flow controller included in the bodily-fluid collection device of FIG. 2, taken along the line $X_3$-$X_3$ and $X_4$-$X_4$ in FIG. 3, respectively.
Figure 7:
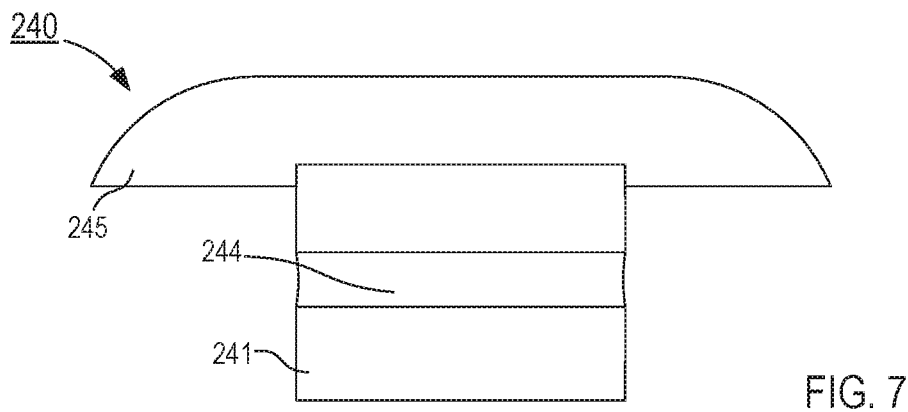

As shown in FIGS. 6 and 7, the flow controller 240 includes a first member 241 and a second member 245. The first member 241 is configured to be disposed in a recess 266 of the housing 201 (see e.g., FIG. 4), and can be made of any number of materials that are biocompatible such as, for example, titanium, graphite, pyrolytic carbon, polyester, polycarbonate, polyurethane, elastomeric material and/or the like. In some embodiments, the second member 245 serves as an actuator to move the first member 241 from a first configuration to a second configuration. More specifically, when the first member 241 is disposed in the recess 266, the second member 245 can be moved between a first position and a second position to move the flow controller 240 between the first and second configuration. In some embodiments, the housing 201 can selectively limit movement of the second member 245 from its first position to its second position. In some embodiments, the housing 201 can be configured to prevent movement of the second member 245 once it has been moved to the second position. Said another way, the housing 201 can include a locking mechanism that prevents the second member 245 from being moved from the second position back to the first position. The second member 245 and/or the housing 201 can also include mechanical detents and/or other indicators that provide visual or tactile feedback to ensure precise positioning of the second member 245.

The first member 241 can include multiple channels for directing fluid flow following a venipuncture (and/or other method of accessing a patient's bodily-fluid). For example, as shown in FIGS. 6 and 7, the first member 241 includes a first flow channel 242 and a second flow channel 244. When the second member 245 is in the first position (see e.g., FIGS. 8 and 9), the flow controller 240 is placed in the first configuration and the first flow channel 242 establishes fluid communication between the inlet port 221 and the first outlet port 230 while fluidically isolating the inlet port 221 from the inner flow channel 235. When the second member 245 is in the second position (see e.g., FIGS. 10-13), the flow controller 240 is placed in the second configuration and the second flow channel 244 establishes fluid communication between the inlet port 221 and the inner flow channel 235 while fluidically isolating the inlet port 221 from the first outlet port 230. Additional second member 245 positions corresponding to additional first member 241 flow channels and/or flow controller 240 configurations can be included to further direct/isolate fluid flow between the patient and the collection device 200. For example, the second member 245 can have a third position corresponding to a third configuration of the flow controller 240 that substantially prevents fluid flow between the patient and the collection device 200 altogether. Said another way, in some embodiments, the dial can be moved to a third position after all bodily-fluid samples are taken from the patient to substantially seal the samples in the collection device 200 from the external environment.

Figure 8:
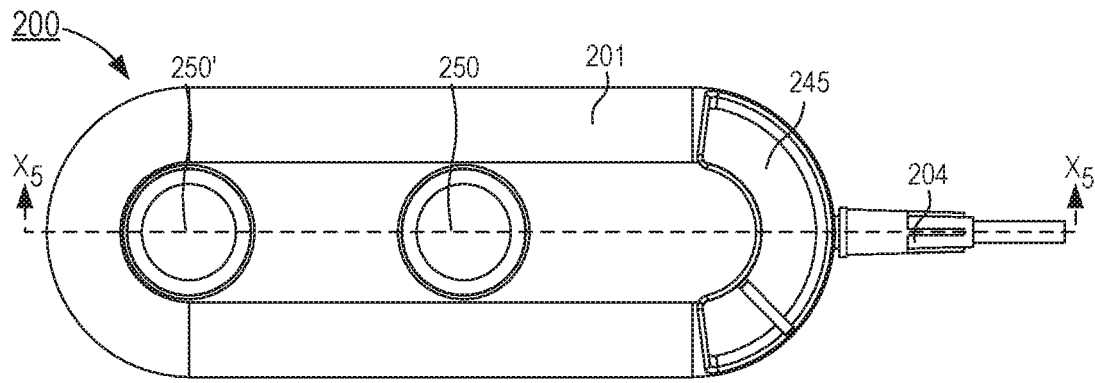
FIG. 8 is a top view of the bodily-fluid collection device of FIG. 2 in a first configuration.
Figure 9:
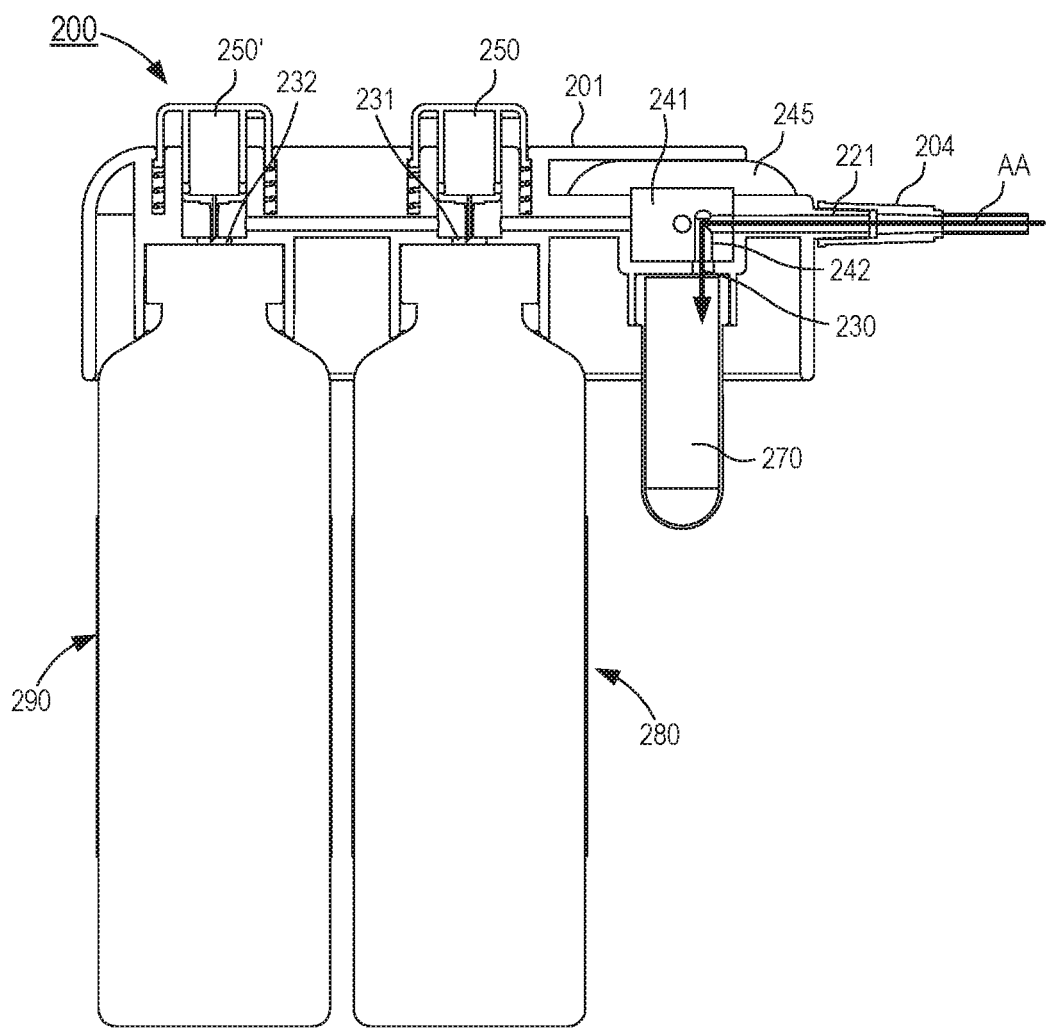
FIG. 9 is a cross-sectional view of the bodily-fluid collection device of FIG. 2 in the first configuration, taken along the line $X_5$-$X_5$ in FIG. 8.

In operation, the collection device 200 can be used to collect bodily-fluids (e.g., blood) from a patient with reduced contamination from dermally-residing microbes and/or other undesirable external contaminants. For example, the inlet port 221 of the collection device 200 is fluidically coupled to a needle or other lumen-defining device (e.g., flexible sterile tubing) via the adapter 204. Following venipuncture (or other bodily-fluid access method), the second member 245 is rotated until it reaches the first position as shown in FIGS. 8 and 9. Alternatively, the second member 245 can be pre-set in the first position and the collection device 200 can be otherwise sealed to preserve the vacuum in the pre-sample reservoir 270 and the sterility of the collection device 200. For example, the inlet port 221 and/or the adapter 204 can include a valve that is opened when the collection device 200 is coupled to the needle or other lumen-defining device.

As described above, when the second member 245 is in the first position, the flow controller 240 is placed in the first configuration and the first flow channel 242 of the first member 241 establishes fluid communication between the inlet port 221 and the first outlet port 230 while fluidically isolating the inlet port 221 from the inner flow channel 235. Additionally, the first and second sample reservoirs 280 and 290 are fluidically isolated from the inlet port 221 in the first configuration and a fluid flow path is defined between a portion of the body of a patient (e.g. a vein) and the pre-sample reservoir 270 as indicated by the arrow AA in FIG. 9. As described above, fluid reservoirs used in the collection device 200 such as the pre-sample reservoir 270, and the sample reservoirs 280 and 290 can be configured to define a negative pressure (i.e., a pressure less than the fluid pressure of the portion of the body that the collection device 200 is being used to withdraw bodily-fluid from) so that once fluid communication is established between a portion of the body of the patient (e.g., a vein) and the pre-sample reservoir 270, the negative pressure within the pre-sample reservoir 270 is such that the pressure differential between the pre-sample reservoir 270 and the portion of the body of the patient draws the bodily-fluid into the pre-sample reservoir 270. In this first configuration, the flow controller 240 also fluidically isolates the pre-sample reservoir 270 from the inner flow channel 235. Thus, a first amount (predetermined or undetermined) of bodily-fluid can be received into the pre-sample reservoir 270 immediately after venipuncture (for example) and isolated from subsequent samples. In this manner, the collection device 200 can be used to prevent the first amount of bodily-fluid, which is most likely to contain bodily surface microbes and/or other undesirable external contaminants, from contaminating subsequent amounts of the bodily-fluid samples that are collected and used for diagnostic or other testing that can be impacted by the contaminants.

Figure 10:
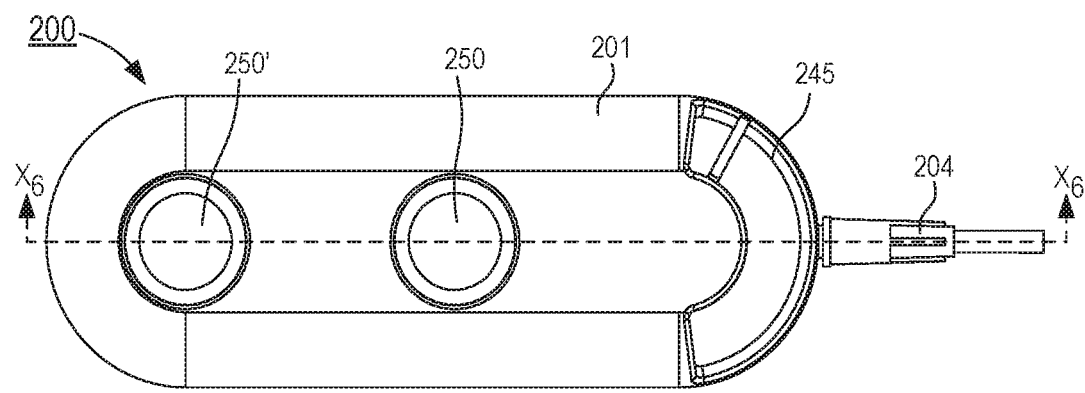
FIG. 10 is a top view of the bodily-fluid collection device of FIG. 2 in a second configuration.
Figure 11:
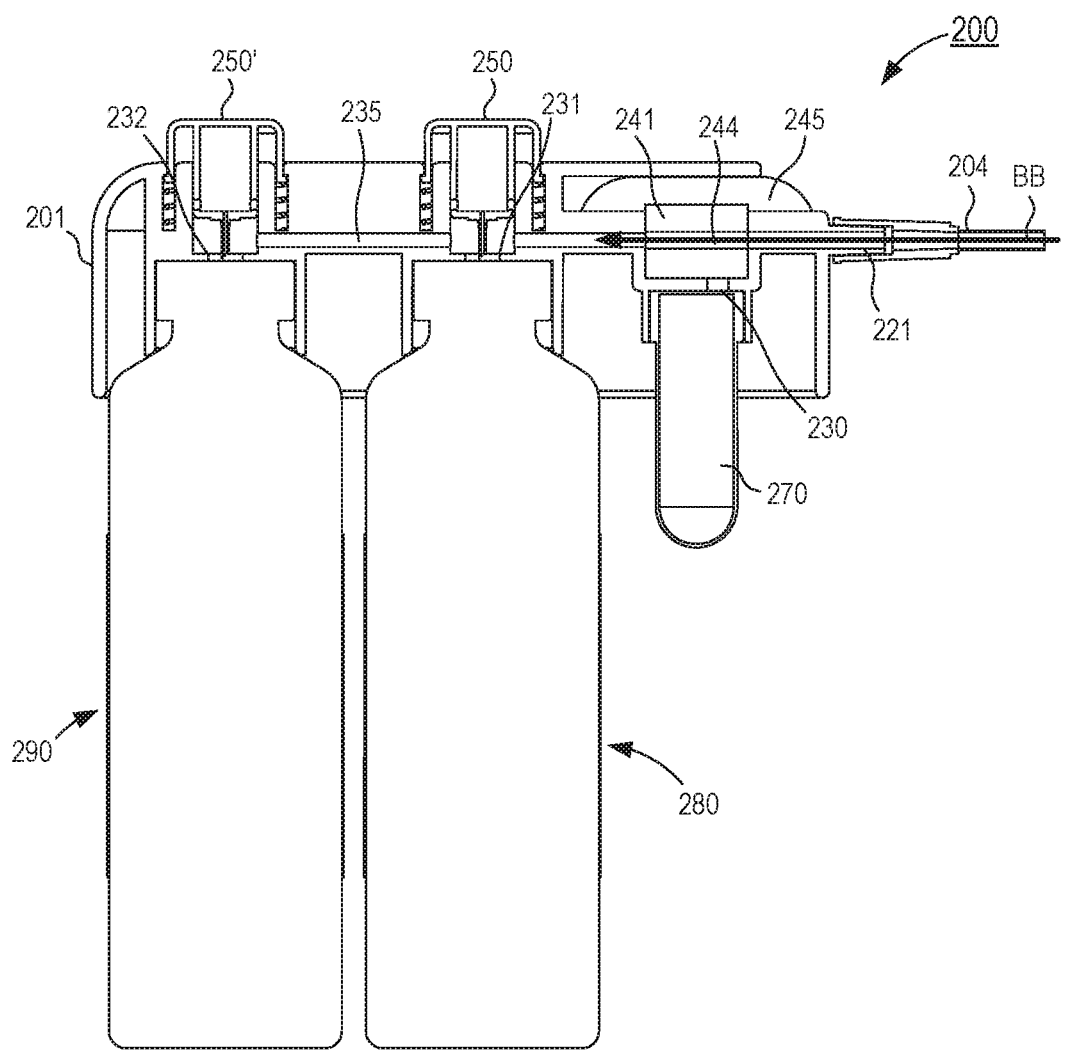
FIG. 11 is a cross-sectional view of the bodily-fluid collection device of FIG. 2 in the second configuration, taken along the line $X_6$-$X_6$ in FIG. 10.
Figure 12:
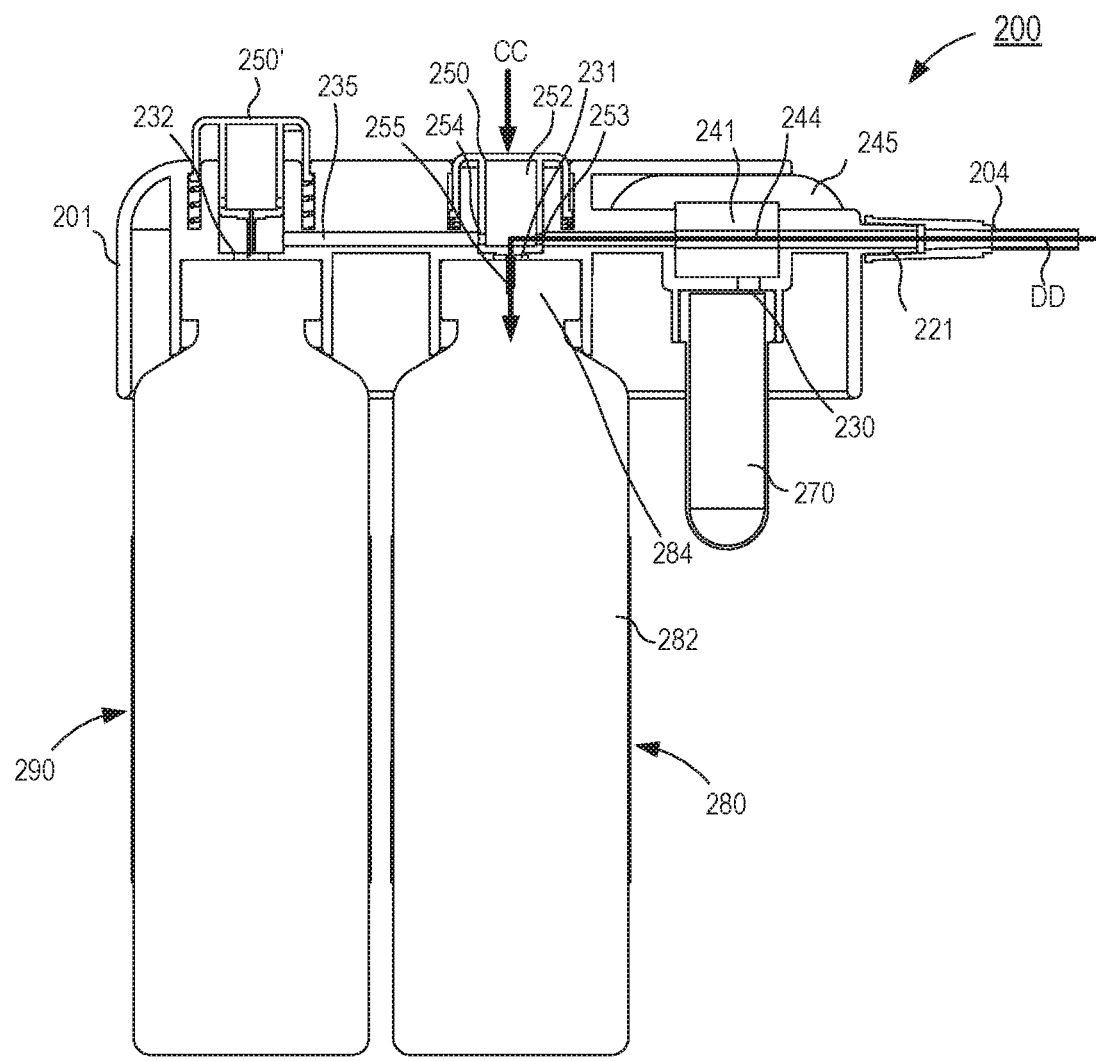
FIGS. 12 and 13 are cross-sectional views of the bodily-fluid collection device of FIG. 2, in a third configuration and a fourth configuration, respectively, taken along the line $X_6$-$X_6$ in FIG. 10.

Following collection of the volume of bodily-fluid pre-sample in the pre-sample reservoir 270, the second member 245 can be rotated until it reaches the second position as shown in FIGS. 10 and 11. When the second member 245 is in the second position, the flow controller 240 is placed in the second configuration and the second flow channel 244 of the first member 241 establishes fluid communication between the inlet port 221 and the inner flow channel 235, while fluidically isolating the first outlet port 230 (i.e., the pre-sample reservoir 270) from the inlet port 221. Said another way, in the second configuration, the flow controller 240 establishes a fluid flow path between a portion of the body of a patient (e.g. a vein) and the inner flow channel 235 via the second flow channel 244 as indicated by arrow BB in FIG. 11.

With the flow controller 240 in the second configuration, the movable members 250 and/or 250' can be actuated (i.e., depressed) from the first position to the second position by the user to establish fluid communication between a part of the body of a patient (e.g., a vein) and the first sample reservoir 280 and/or the second sample reservoir 290. More specifically, the movable member 250 is moved from its first position to its second configuration to pass the piercing member 255 through the outlet port 231 in such a manner that the piercing member 255 can puncture the vacuum seal 284 of the first sample reservoir 280 to be disposed inside the sample, container 282, as indicated by the arrow CC in FIG. 12. While in the second position, the inlet port 253 and the outlet port 254 of the movable member 250 are substantially aligned with, and in fluid communication with, the inner flow channel 235, which allows the bodily-fluid to flow from the inner flow channel 235, into the inner cavity 252 of the movable member 250, and out the lumen 256 of the piercing member 255 into the first sample reservoir 280. The pressure differential between the sample reservoir 280 (e.g., vacuum or negative pressure) and the inner flow channel 235 draws the bodily-fluid into the sample reservoir 280. Said another way, in the second configuration, the movable member 250 establishes a fluid flow path between the inner flow channel 235 and the first sample reservoir 280 as indicated by the arrow DD in FIG. 12. Once a desired volume of bodily-fluid (e.g., the second amount) is collected in the first sample reservoir 280, the user can release the movable member 250 allowing the bias member 259 to move the button 250 back to its first position. With the movable member 250 back in its first position, the piercing member 255 is removed from the first sample reservoir 280 and the seal 284 (e.g., a self sealing septum) fluidically isolates the first sample reservoir 280 from the inner flow channel 235.

Figure 13:
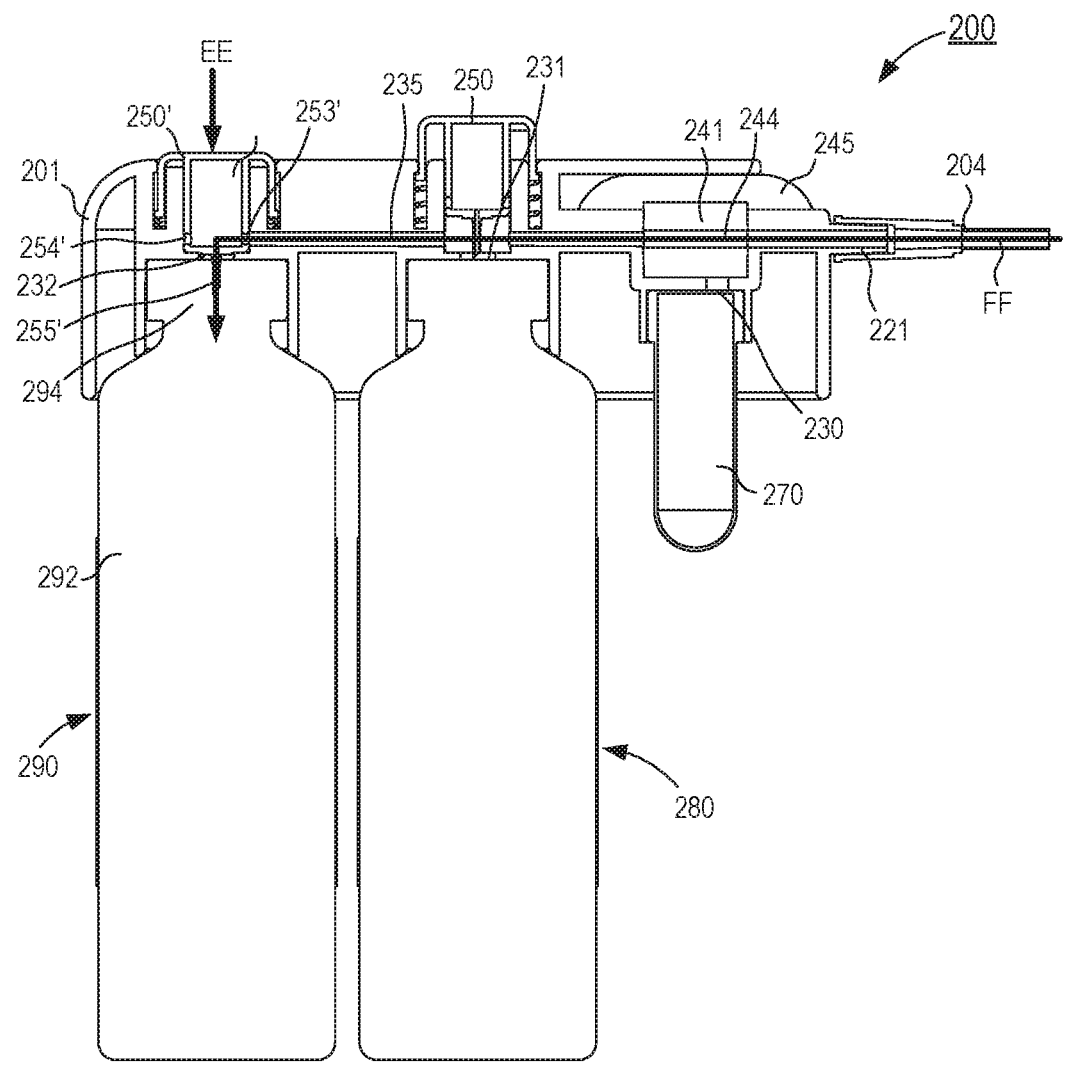

In a similar manner, while the flow controller 240 is in the second configuration, the movable member 250' can be actuated (depressed) from its first position to its second position by the user, as indicated by the arrow EE in FIG. 13. In this manner, fluid communication is established between a part of the body of a patient (e.g., a vein) and the second sample reservoir 290 (via the outlet port 232) in a manner similar to that of the movable member 250 and first sample reservoir 280 described above. Said another way, in the second configuration, the movable member 250' establishes a fluid flow path between the inner flow channel 235 and the second sample reservoir 290 as indicated by the arrow FF in FIG. 13. Once a desired volume of bodily-fluid (e.g., the third amount) is collected in the second sample reservoir 290, the user can release the movable member 250' allowing the bias member 259' to move the button 250' back to its first position. Although shown and described as being a sequential process, the order of fill and/or sequencing is not necessarily required (i.e., sample reservoir 280 does not necessarily have to be filled before sample reservoir 290, etc.). Said another way, once the flow controller 240 is moved to the second configuration, the first sample reservoir 280 and the second sample reservoir 290 (and any additional sample reservoirs) can be filled in any order, at the same time (e.g., simultaneously), and/or at overlapping time intervals. For example, the user can begin to fill the first sample reservoir 280 and then after the first sample reservoir 280 is partially filled, the user can depress the movable member 250' to being filling the second sample reservoir 290 while the first sample reservoir 280 is finished filling. Additionally, adjustments in the volume of the bodily-fluid collected in the sample reservoirs 280 and/or 290 can be made possible by actuating (inserting) the movable members 250 and/or 250' repeatedly. As described above, the second member 245 can have a third position corresponding to a third configuration of the flow controller 240 that can substantially prevent fluid flow between the patient and the collection device 200 altogether to substantially seal the samples in the collection device 200 from the external environment.

Although not shown in FIGS. 2-13, the collection device 200 can include a flow metering device or the like that can be configured to meter a volume of bodily-fluid that is transferred to the pre-sample reservoir 270, the first sample reservoir 280, and/or the second sample reservoir 290. For example, in some embodiments, the first member 241 of the flow controller 240 can include a flow metering device that is in fluid communication with the first flow channel 242 and the second flow channel 244. In other embodiments, a flow metering device can be disposed within the inner cavity 252 of the movable members 250 and/or 250'. Thus, a volume of bodily-fluid sample transferred to and disposed in the first sample reservoir 280 and the second sample reservoir 290 can be metered and/or controlled such that the volume of bodily-fluid sample disposed in each sample reservoir 280 and 290 is a predetermined volume such as, for example, 10 mL, 20 mL, 30 mL, etc.

Although the collection device 200 is shown and described as including a first sample reservoir 280 and a second sample reservoir 290, in other embodiments, a collection device can include any number of sample reservoirs. For example, in some embodiments, a collection device substantially similar to the collection device 200 can be used with, for example, one, two, three, four, five, six, or more sample reservoirs.

FIGS. 14-20 illustrate a collection device 300 according to an embodiment. The collection device 300 includes a diversion mechanism 320, a flow controller 340, and sample reservoirs 380, 380', 390 and 390'. As further described herein, the collection device 300 can be moved between a first, a second, a third, a fourth, and a fifth configuration to deliver a flow of a bodily-fluid that is substantially free from microbes exterior the body, such as, for example, dermally residing microbes and/or other undesirable external contaminants. The collection device 300 can be any suitable shape, size, or configuration. For example, while shown in FIGS. 14-20 with the sample reservoirs 380, 380', 390 and 390' oriented vertically with respect to the housing 301, the collection device 300 can have the sample reservoirs 380, 380', 390 and 390' oriented in any suitable plane with respect to the housing 301, or conically disposed with respect to the housing 301, and/so forth.

The sample reservoirs 380, 380', 390 and 390' are substantially similar or the same in form and function to the sample reservoirs 280 and/or 290 of the collection device 200 and thus, are not described in detail herein. As discussed above, the sample reservoirs 380, 380', 390 and 390' maintain negative pressure conditions (vacuum conditions) that can allow drawing of bodily-fluid from a patient to the sample reservoirs 380, 380', 390 and 390' via suction. In some embodiments, sample reservoirs 380 and 380' can be aerobic culture bottles and sample reservoirs 390 and 390' can be anaerobic culture bottles and the collection device 300 can be used to collect multiple aerobic and multiple anaerobic blood culture samples from a single venipuncture. As described in further detail herein, the sample reservoirs 380, 380', 390 and 390' can each be placed in fluid communication with at least a portion of the diversion mechanism 320 to receive a volume of a bodily-fluid sample. The volume of the bodily-fluid samples can be a predetermined or undetermined amount. Moreover, once a desired volume of bodily-fluid is disposed in the sample reservoirs 380, 380', 390, 390', each sample reservoir 380, 380', 390, and 390' can be fluidically isolated from at least a portion of the diversion mechanism 320, as described in further detail herein.

The diversion mechanism 320 includes a housing 301 and a distribution member 329. The housing 301 of the diversion mechanism 320 is physically and fluidically coupled to the distribution member 329, and provides and/or defines a set of fluid flow pathways for collecting bodily-fluids from the patient. The housing 301 defines a recess 366 and a set of outlet apertures 303. The recess 366 is configured to receive a seal member 341 included in the flow controller 340, as described in further detail herein. The set of outlet apertures 303 includes a first outlet aperture 303a, a second outlet aperture 303b, a third outlet aperture 303c, a fourth outlet aperture 303d, and a fifth outlet aperture 303e that are each configured to define a different fluid flow path in fluid communication with different portions of the distribution member 329. More specifically, the distribution member 329 defines and/or forms at least a portion of a pre-sample reservoir 370 in fluid communication with the first outlet aperture 303a, and a first flow channel 335a in fluid communication with the second outlet aperture 303b, second flow channel 335b in fluid communication with the third outlet aperture 303b, a third flow channel 335c in fluid communication with the fourth outlet aperture 303d, and a fourth flow channel 335 in fluid communication with the fifth outlet aperture 303e.

Figure 15:
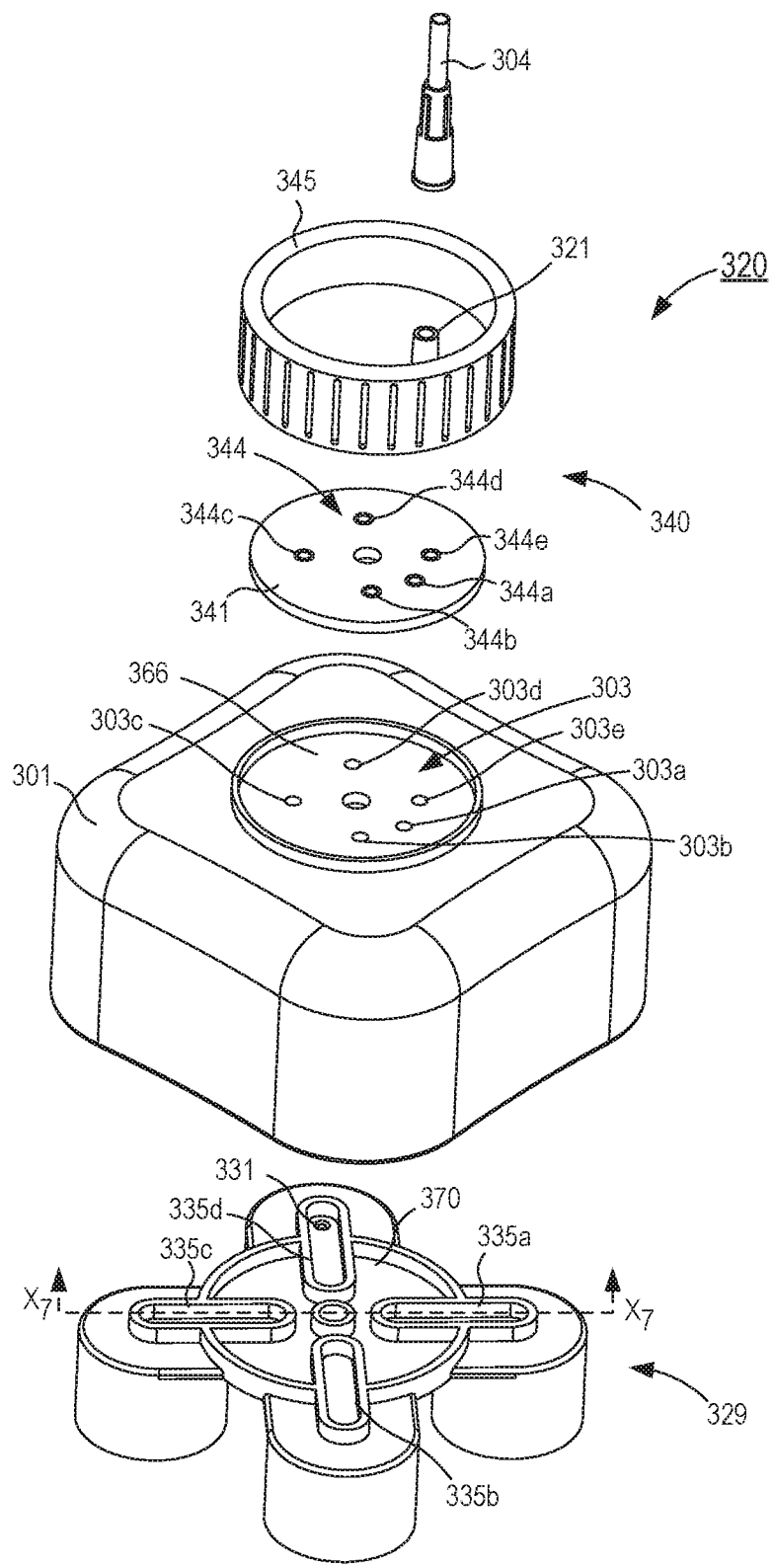
FIG. 15 is an exploded perspective view of a diversion mechanism included in the bodily-fluid collection device of FIG. 14.
Figure 16:
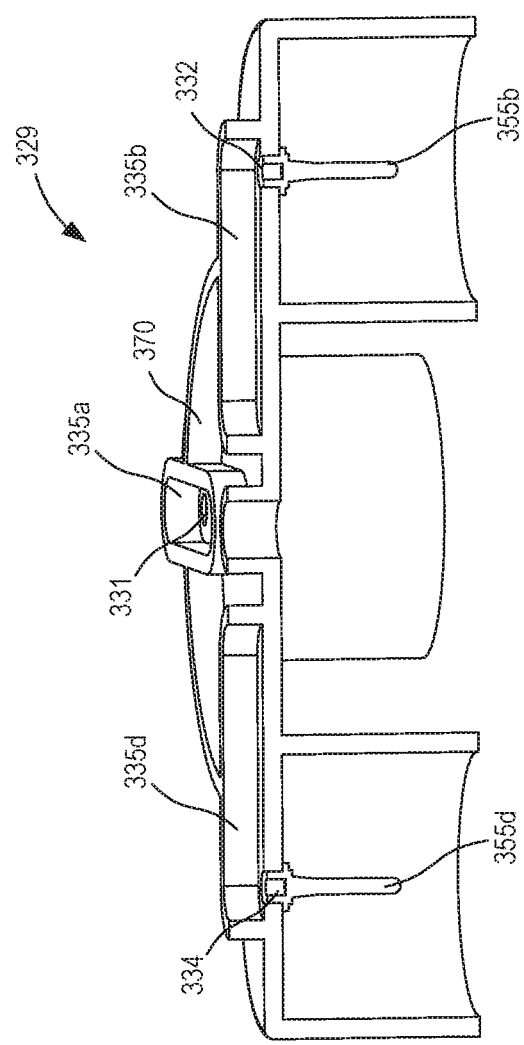
FIG. 16 is a cross-sectional side view of a distribution member included in the bodily-fluid collection device of FIG. 14, taken along the line $X_7$-$X_7$ in FIG. 15.

As shown in FIGS. 15 and 16, the distribution member 329 defines a chamber or volume that defines at least a portion of the pre-sample reservoir 370. The pre-sample reservoir 370 is configured to contain bodily-fluids such as, for example, blood, plasma, urine, and/or the like. The first outlet aperture 303a of the housing 301 can be substantially aligned with an open portion of the pre-sample reservoir 370 to allow the pre-sample reservoir 370 to receive a flow of bodily-fluid from the patient. For example, the pre-sample reservoir 370 can receive and contain a first amount or volume of the bodily-fluid, where the first amount of bodily-fluid can be a predetermined or undetermined amount. Moreover, the arrangement of the diversion mechanism 320 can be such that the pre-sample reservoir 370 is maintained in fluidic isolation from the flow channels 335a, 335b, 335c, and 335d and/or subsequent volumes of bodily-fluid withdrawn from the patient, as described in further detail herein. While the pre-sample reservoir 270 is described above as maintaining a negative pressure, the pre-sample reservoir 370 does not maintain negative pressure conditions (vacuum conditions), and hence other mechanisms such as, for example, gravitational pull can be used to draw the bodily-fluid into the pre-sample reservoir 370.

The flow channels 335a-335d extend radially from a center of the distribution member 329 and are arranged such that each flow channel. 335a, 335b, 335c, and 335d is fluidically isolated from the pre-sample reservoir 370 and the other flow channels. In this manner, the flow channels 335a, 335b, 335c, and 335d can direct and/or otherwise define a fluid flow path between a first end portion that is substantially aligned with the outlet apertures 303b, 303c, 303d, and 303e, respectively, and a second end portion. As shown in FIGS. 15 and 16, the distribution member 329 defines a first outlet port 331 disposed at the second end portion of the first flow channel 335a, a second outlet port 332 disposed at the second end portion of the second flow channel 335b, a third outlet port 333 disposed at the second end portion of the third flow channel 335c, and a fourth outlet port 334 disposed at the second end portion of the fourth flow channel 335d. Moreover, the distribution member 329 includes a first piercing member 355a, a second piercing member 355b, a third piercing member 355c, and a fourth piercing member 355d that are physically and fluidically coupled to the first outlet port 331, the second outlet port 332, the third outlet port 333, and the fourth outlet port 334, respectively. As such, the piercing members 355a-355d can be used to puncture a vacuum seal of the sample reservoirs 380, 380', 390 and 390' which can initiate a flow of bodily-fluid, as described in further detail herein. Although not shown in FIGS. 15 and 16, the sample reservoirs 380, 380', 390 and 390' can be physically coupled to a portion of the distribution member 329 (either directly or via an intervening structure such as sterile flexible tubing) in any suitable manner that can allow the sample reservoirs 380, 380', 390, and 390' to be placed in fluid communication with the outlet ports 331, 332, 333, and 334, respectively The flow controller 340 includes a dial 345 and a seal member 341. The seal member 341 is disposed in the recess 366 of the housing 301 (see e.g., FIG. 18). More particularly, the flow controller 340 can be coupled to the housing 301 such that the seal member 341 is disposed between and in contact with a surface of the housing 301 defining the recess 366 and a surface of the dial 345. Moreover, the seal member 341 can have a size and a shape such that, when the flow controller 340 is coupled to the housing 301, the seal member 341 forms a substantially fluid tight seal with the surface of the dial 345 and the surface of the housing 301 that defines the recess 366 (see e.g., FIG. 18), as described in further detail herein. The seal member 341 can be made of any number of materials that are biocompatible such as, for example, silicone, polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, nylons, polyesters, polycarbonates, polyacrylates, polymers of ethylene-vinyl acetates and other acyl substituted cellulose acetates, polystyrenes, polyvinyl chloride, polyvinyl fluoride, poly(vinyl imidazole), chlorosulphonate polyolefins, polyethylene oxide, and/or blends and copolymers thereof.

As shown in FIG. 15, the seal member 341 defines a set of apertures 344 that can direct a flow of bodily-fluid following a venipuncture (or other method of accessing bodily-fluid). For example, the set of apertures 344 defined by the seal member 341 includes a first aperture 344a, a second aperture 344b, a third aperture 344c, a fourth aperture 344d, and a fifth aperture 344e. The arrangement of the seal member 341 is such that when the seal member 341 is disposed in the recess 366, the first aperture 344a, the second aperture 344b, the third aperture 344c, the fourth aperture 344d, and the fifth aperture 344e are substantially aligned with the first outlet aperture 303a, the second outlet aperture 303b, the third outlet aperture 303c, the fourth outlet aperture 303d, and the fifth outlet aperture 303e of the housing 301, respectively.

The dial 345 of the flow controller 340 is rotatably coupled to the housing 301 and movable between a first position, a second position, a third position, a fourth position, and a fifth position relative to the housing 301. The dial 345 includes an inlet port 321 that defines a lumen 302. The inlet port 321 can be fluidically coupled to a medical device (not shown) that defines a fluid flow pathway for withdrawing and/or conveying bodily-fluid from a patient to the collection device 300. For example, the inlet port 321 can be fluidically coupled to a needle or other lumen-defining device (e.g., flexible sterile tubing) either directly or indirectly via an adapter 304. Similarly stated, the inlet lumen 302 defined by the inlet port 321 is placed in fluid communication with a lumen defined by a lumen-defining device, when the lumen-defining device is coupled to the inlet port 321. In this manner, the inlet port 321 can be configured to selectively place the pre-sample reservoir 370, the first sample reservoir 380, the second sample reservoir 380', the third sample reservoir 390, and the fourth sample reservoir 390' in fluid communication with the patient, as described in further detail herein.

As described above, the dial 345 is movable between the first, the second, the third, the fourth, and the fifth positions. When the dial 345 is in the first position, the flow controller 340 is placed in a first configuration and the inlet port 321 can be substantially aligned with the first aperture 344a of the seal member 341 and the first outlet aperture 303a of the housing 301. In this manner, first aperture 344a of the seal member 341 establishes fluid communication between the inlet port 321 and the first outlet aperture 303a while fluidically isolating the inlet port 321 from the outlet apertures 303b, 303c, 303d, and 303e which in turn, fluidically isolates the inlet port 321 from the flow channels 335a-335d. With the first outlet port 303a aligned with an open portion of the pre-sample reservoir 370, the first aperture 344a and the first outlet aperture 303a establish fluid communication between the inlet port 321 and the pre-sample reservoir 370. When the dial 345 is rotated (or actuated) to the second position, the flow controller 340 is placed in a second configuration and the second outlet aperture 344b establishes fluid communication between the inlet port 321 and the second outlet aperture 303b while fluidically isolating the inlet port 321 from the outlet apertures 303a, 303c, 303d, and 303e. With the second outlet aperture 303b aligned with the first end portion of the first flow channel 335a, the second aperture 344b and the second outlet aperture 303b establish fluid communication between the inlet port 321 and the first flow channel 335a.

The collection device 300 works in a similar manner when the dial 345 is rotated to the third, fourth and fifth positions. Thus, when the inlet lumen 302 is placed in fluid communication with the patient (e.g., via the medical device coupled to the inlet port 321), the first outlet port 330, the second outlet port 331, the third outlet port 332, the fourth outlet port 333, and the fifth outlet port 334 can be selectively placed in fluid communication with the inlet lumen 302 to allow all the bodily-fluid to flow into at least one of the pre-sample reservoir 370, or one or more of the sample reservoirs 380, 380', 390 and 390'. In some embodiments, additional dial 345 positions corresponding to additional seal outlet apertures and/or flow controller 340 configurations can be included to further direct/isolate fluid flow between the patient and the collection device 300. For example, the dial 345 can have a sixth position corresponding to a sixth configuration of the flow controller 340 that substantially prevents fluid flow between the patient and the collection device 300 altogether. Said another way, in some embodiments, the dial 345 can be moved to a sixth position after all bodily-fluid samples are taken from the patient to substantially seal the samples in the collection device 300 from the external environment.

In some embodiments, the bodily-fluid is prevented from flowing to the outlet ports associated with the sample reservoirs (e.g., outlet ports 331-334) until after a predetermined volume of bodily-fluid is collected in the pre-sample reservoir 370. In some embodiments, the outlet ports associated with the sample reservoirs (e.g., outlet ports 331-334) can only be placed in fluid communication with the inlet lumen 302 sequentially (e.g., outlet port 331 must be in fluid communication with the inlet lumen 302 before outlet port 332, and so on). In some embodiments, the outlet ports associated with subsequent sample reservoirs (e.g., outlet ports 332-334) can only be placed in fluid communication with the inlet lumen 302 after a confirmed volume of bodily-fluid has been collected. In some embodiments, the outlet ports associated with the sample reservoirs (e.g., outlet ports 331-334) can be placed in fluid communication with the inlet lumen 302 in any random manner without any preference for order (e.g., outlet port 334 can be in fluid communication with the inlet lumen 302 before outlet port 331, outlet port 332 can be in fluid communication with the inlet lumen 302 before outlet port 333, and so on).

In some embodiments, the housing 301 can selectively limit movement of the dial 345 from its first position to its second, third, fourth, and fifth positions. In some embodiments, the housing 301 can be configured to prevent movement of the dial 345 once it has been moved to the fifth position. Said another way, the housing 301 can include a locking mechanism that prevents the dial 345 from being moved from the fifth position back to the first position. The dial 345 and/or the housing 301 can also include mechanical detents and/or other indicators that provide visual or tactile feedback to ensure precise positioning of the dial 345 with respect to the outlet apertures 303a-303e of the housing 301.

Figure 18:
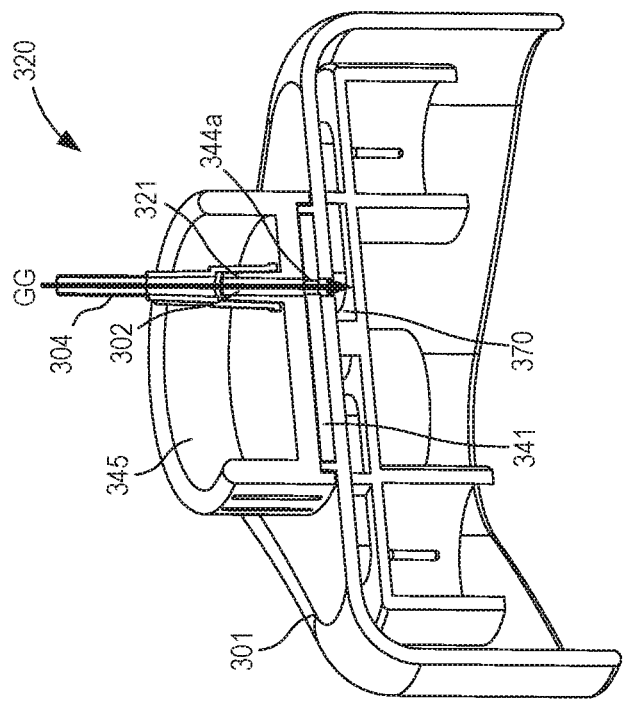
FIG. 18 is a cross-sectional view of a portion the bodily-fluid collection device of FIG. 14 in the first configuration, taken along the line $X_8$-$X_8$ in FIG. 17.
Figure 17:
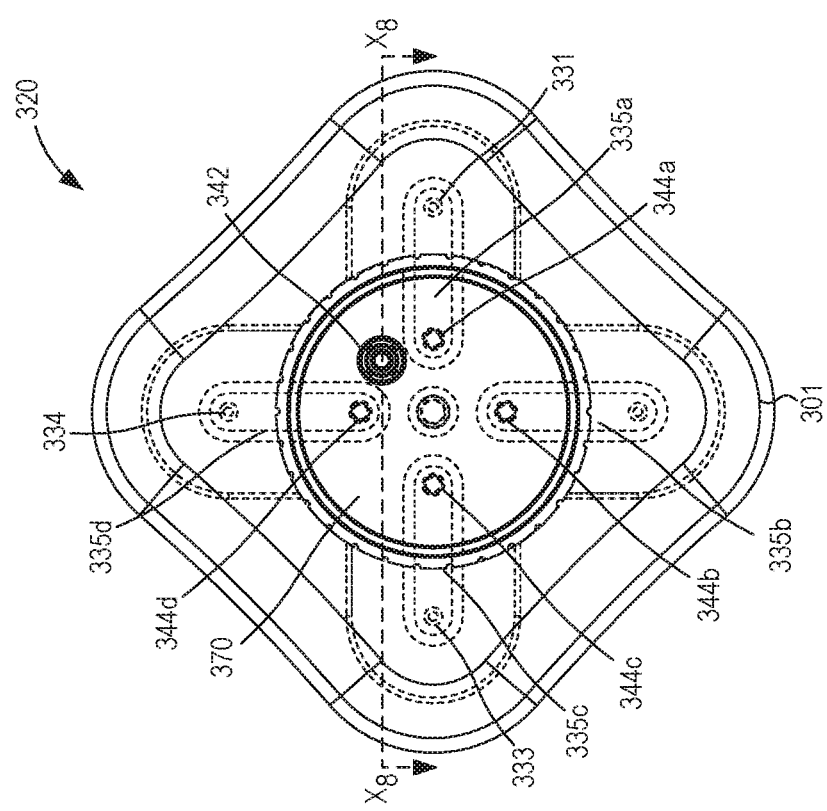
FIG. 17 is a top view of the bodily-fluid collection device of FIG. 14 in a first configuration.

In operation, the collection device 300 can be used to collect bodily-fluids (e.g., blood, plasma, urine, and/or the like) from a patient with reduced contamination. For example, the inlet port 321 of the collection device 300 can be fluidically coupled to a needle or other lumen-defining device (e.g., flexible sterile tubing). Following venipuncture (or other method of accessing bodily-fluid), the dial 345 is actuated (or rotated) until it reaches the first position, as shown in FIGS. 17 and 18. Alternatively, the dial 345 can be pre-set in the first position and the collection device 300 can be otherwise sealed to preserve the sterility of the collection device 300. For example, the inlet port 321 can include a valve that is opened when the collection device 300 is coupled to the needle or other lumen-defining device.

As described above, when the dial 345 is in the first position, the flow controller 340 is placed in the first configuration and the first aperture 344a of the seal member 341 establishes fluid communication between the inlet port 321 and the first outlet port 330 (contained within the housing 301) while fluidically isolating the inlet port 321 from the four flow channels 335a-335d. Additionally, the sample reservoirs 380, 380', 390 and 390' are fluidically isolated from the inlet port 321 in the first configuration and a fluid flow path is defined between a portion of the body of a patient (e.g. a vein) and the pre-sample reservoir 370 as indicated by the arrow GG in FIG. 18. In this first configuration, the bodily-fluid flows (e.g., by gravitation force, vacuum, etc.) from the portion of the body of the patient through the inlet lumen 302 of the inlet port 321, the first aperture 344a of the seal member 341, the first outlet port 330, and into the pre-sample reservoir 370. In the first configuration, the flow controller 340 also fluidically isolates the pre-sample reservoir 370 from the flow channels 335a-335d. Thus, a first amount (predetermined or undetermined) of bodily-fluid can be received into the pre-sample reservoir 370 immediately after venipuncture and isolated from subsequent samples. In this manner, the collection device 300 can be used to prevent the first amount of bodily-fluid, which is most likely to contain bodily surface microbes and/or other undesirable external contaminants, from contaminating subsequent amounts of the bodily-fluid samples that are collected and used for diagnostic or other testing that can be impacted by the contaminants.

Figure 19:
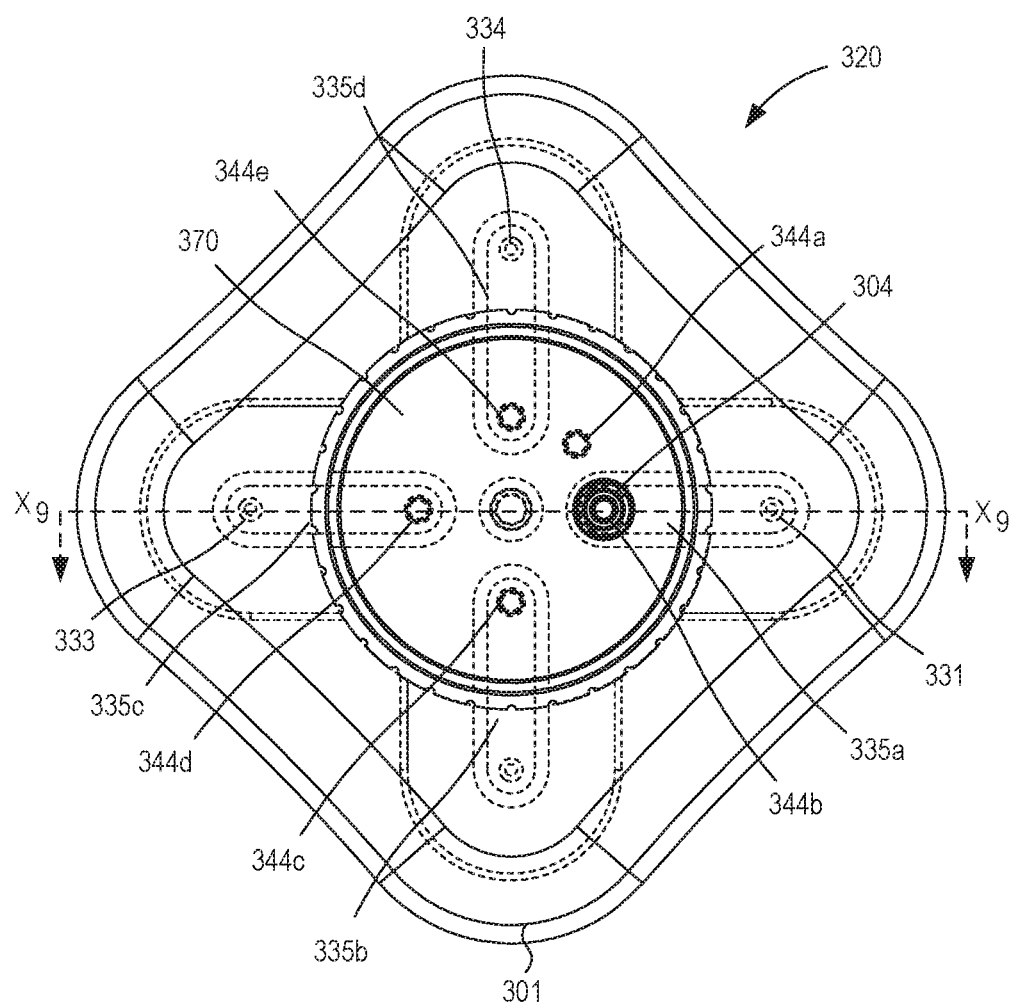
FIG. 19 is a top view of the bodily-fluid collection device of FIG. 14 in a second configuration.
Figure 20:
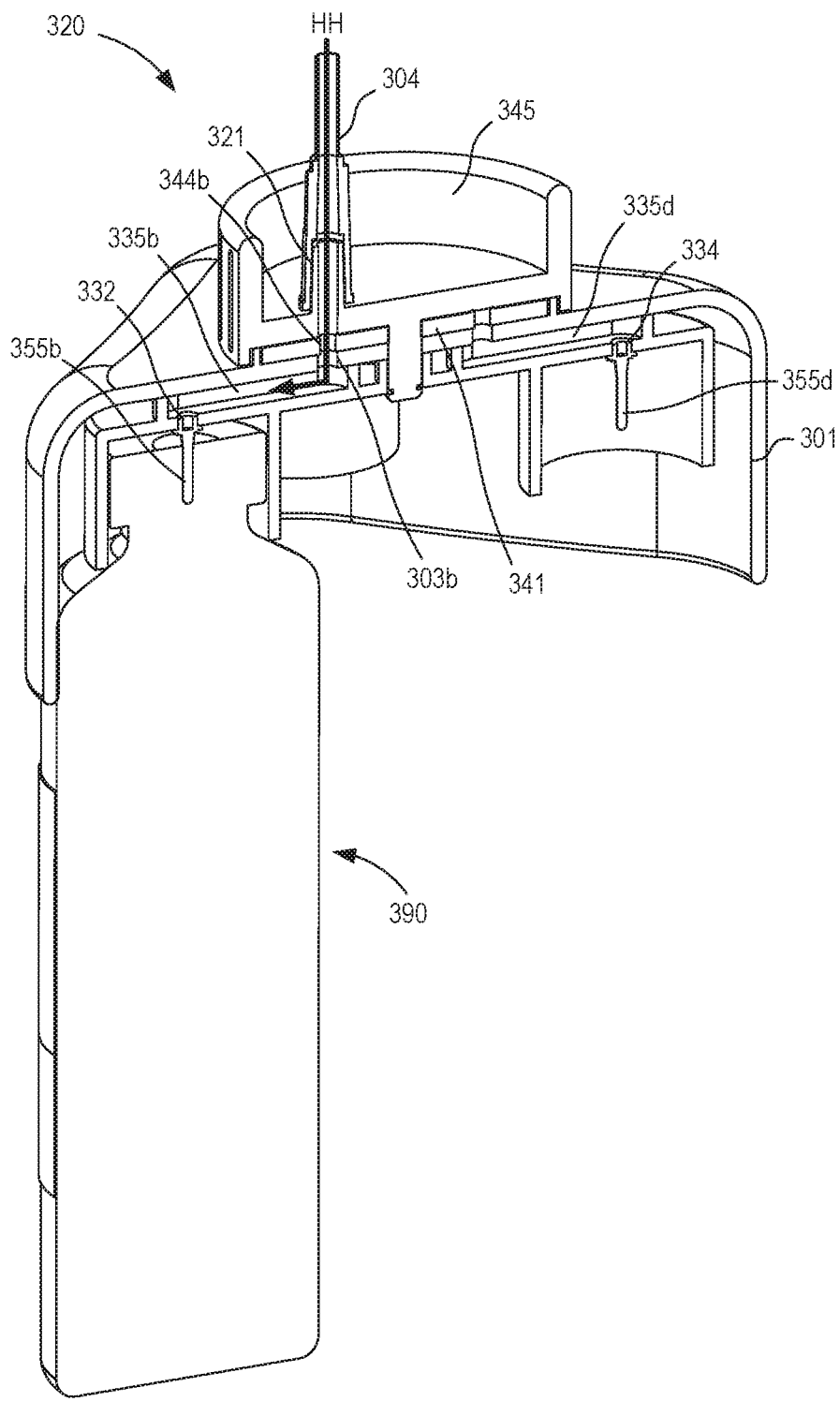
FIG. 20 is a cross-sectional view of the bodily-fluid collection device of FIG. 14 in the second configuration, taken along the line $X_9$-$X_9$ in FIG. 19.
Figure 21:
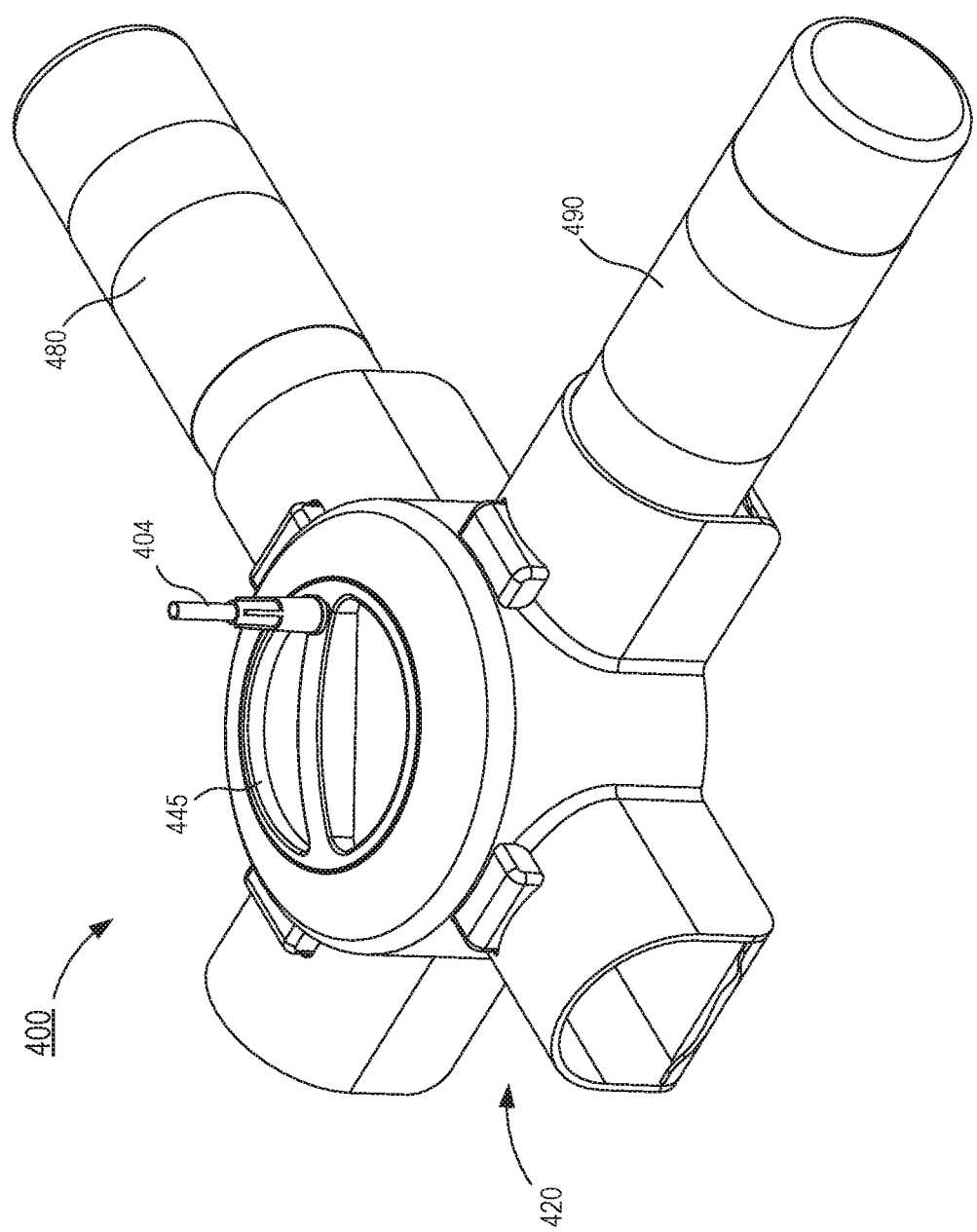
FIG. 21 is a perspective view of a bodily-fluid collection device according to an embodiment.

Following collection of the bodily-fluid pre-sample in the pre-sample reservoir 370, the dial 345 can be actuated (or rotated) until it reaches the second position as shown in FIGS. 19 and 20. When the dial 345 is in the second position, the flow controller 340 is placed in the second configuration and the second aperture 344b of the seal member 341 establishes fluid communication between the inlet port 321 and the flow channel 335a, while fluidically isolating the pre-sample reservoir 370 from the inlet port 321. Said another way, in the second configuration, the flow controller 340 establishes a fluid flow path between a portion of the body of a patient (e.g. a vein) and the flow channel 335a, as indicated by the arrow HH in FIG. 20. With the flow controller 340 in the second configuration, the sample reservoir 380 can be actuated by the user (e.g., pushed against the piercing member 355a) from a first configuration to a second configuration to establish fluid communication between a part of the body of a patient (e.g., a vein) and the first sample reservoir 380.

As described above, moving the sample reservoir 380 to the second configuration results in the piercing member 355a puncturing the vacuum seal of the sample reservoir 380 to be disposed inside the sample reservoir 380. In this second configuration, the part of the body of a patient (e.g., a vein) is exposed to vacuum suction force from the sample reservoir 380 due to the negative pressure conditions (vacuum) therein. The pressure differential between the sample reservoir 380 (e.g., vacuum or negative pressure) and the part of the body of the patient draws the bodily-fluid into the sample reservoir 380. The bodily-fluid flows from the part of the body of a patient through the inlet lumen 302 of the inlet port 321, the second aperture 344b of the seal member 341, the second outlet aperture 303b of the housing 301, and into the first flow channel 335a. The vacuum suction draws the flow of bodily-fluid through the first flow channel 335a into the sample reservoir 380 via the second outlet port 331 and the piercing member 355a. Said another way, in the second configuration, the flow controller 340 establishes a fluid flow path between the inlet port 321 and the sample reservoir 380. Once a desired volume of bodily-fluid (e.g., the second amount) is collected in the sample reservoir 380, the user can actuate (rotate) the flow controller 340 to the third position and/or move the sample reservoir 380 back to its first configuration to isolate the first sample reservoir 380 from the flow channel 335a. When the sample reservoir 380 is back in the first configuration, the piercing member 355a is removed from the sample reservoir 380 and the seal of the sample reservoir 380 (e.g., a self sealing septum) fluidically isolates the first sample reservoir 380 from the flow channel 335a. Filling the other sample reservoirs is done in a similar manner with the flow controller 340 being placed in the third, fourth and fifth configurations respectively.

Note that the order of fill and/or sequencing is not necessarily required (i.e., sample reservoir 380 does not necessarily have to be filled before sample reservoir 390, etc.). Said another way, the first sample reservoir 380 and the second sample reservoir 390 (and any additional sample reservoirs) can be filled in any order. For example, the user can begin to fill the first sample reservoir 380 and then after the first sample reservoir 380 is partially filled, the user can fill the second sample reservoir 390. Additionally, adjustments in the volume of the bodily-fluid collected in the sample reservoirs 380 and/or 390 can be made possible by repeated filling of the sample reservoirs 380 and/or 390. However, in other embodiments, the order of fill can be mechanically manipulated such that the second sample reservoir cannot be accessed until a specified amount of bodily-fluid is confirmed to have been placed into the first reservoir and so on. As described above, the dial 345 can have a sixth position corresponding to a sixth configuration of the flow controller 340 that can substantially prevent fluid flow between the patient and the collection device 300 altogether to substantially seal the samples in the collection device 300 from the external environment.

Although the collection device 300 is shown and described above as including and/or otherwise coupling to a set of four sample reservoirs (e.g., the first sample reservoir 380, the second sample reservoir 380', the third reservoir 390, and the fourth reservoir 390'), in other embodiments, a collection device can include and/or can be coupled to any suitable number of sample reservoirs (e.g., one, two, three, four, five, six, or more).

FIGS. 21-27 present a collection device 400 according to an embodiment. The collection device 400 includes a diversion mechanism 420, a flow controller 440, and sample reservoirs 480 and 490 (although there are holders present for four sample reservoirs, only two sample reservoirs are included in the figures for purposes of clarity and additional sample reservoirs (e.g. a fifth, sixth and so on) may be included as part of the collection device 400). As further described herein, the collection device 400 can be moved between a first, a second, a third, a fourth, and a fifth configuration to deliver a flow of a bodily-fluid that is substantially free from microbes exterior to the body, such as, for example, dermally residing microbes and/or other undesirable external contaminants. The collection device 400 can be any suitable shape, size, or configuration. For example, aspects and/or portions of the collection device 400 can be substantially similar in form and/or function as corresponding aspects and/or portions of any of the collection devices 100, 200, and/or 300, described above. Thus, such similar aspects and/or portions are not described in further detail herein. By way of example, in some embodiments, the sample reservoirs 480 and 490 of the collection device 400 can be substantially similar and/or the same in form and function as the sample reservoirs 380 and 390, respectively, included in the collection device 300 of FIGS. 14-20.

The diversion mechanism 420 includes a housing 401, a distribution member 429, and a base plate 471. As described above with reference to the collection device 300, the housing 401 defines a first outlet aperture 403a, a second outlet aperture 403b, a third outlet aperture 403c, a fourth outlet aperture 403d, and a fifth outlet aperture. 403e that are each configured to be in fluid communication with a different portion of the distribution member 429. More specifically, the distribution member 429 defines and/or forms at least a portion of a pre-sample reservoir 470 in fluid communication with the first outlet aperture 403a, and a first fluid chamber 435a in fluid communication with the second outlet aperture 403b, a second fluid chamber 435b in fluid communication with the third outlet aperture 403b, a third fluid chamber 435c in fluid communication with the fourth outlet aperture 403d, and a fourth fluid chamber 435d in fluid communication with the fifth outlet aperture 403e. Furthermore, the housing 401 defines a recess 466 that is configured to movably receive at least a portion of the flow controller 440, as described in further detail herein.

Figure 22:
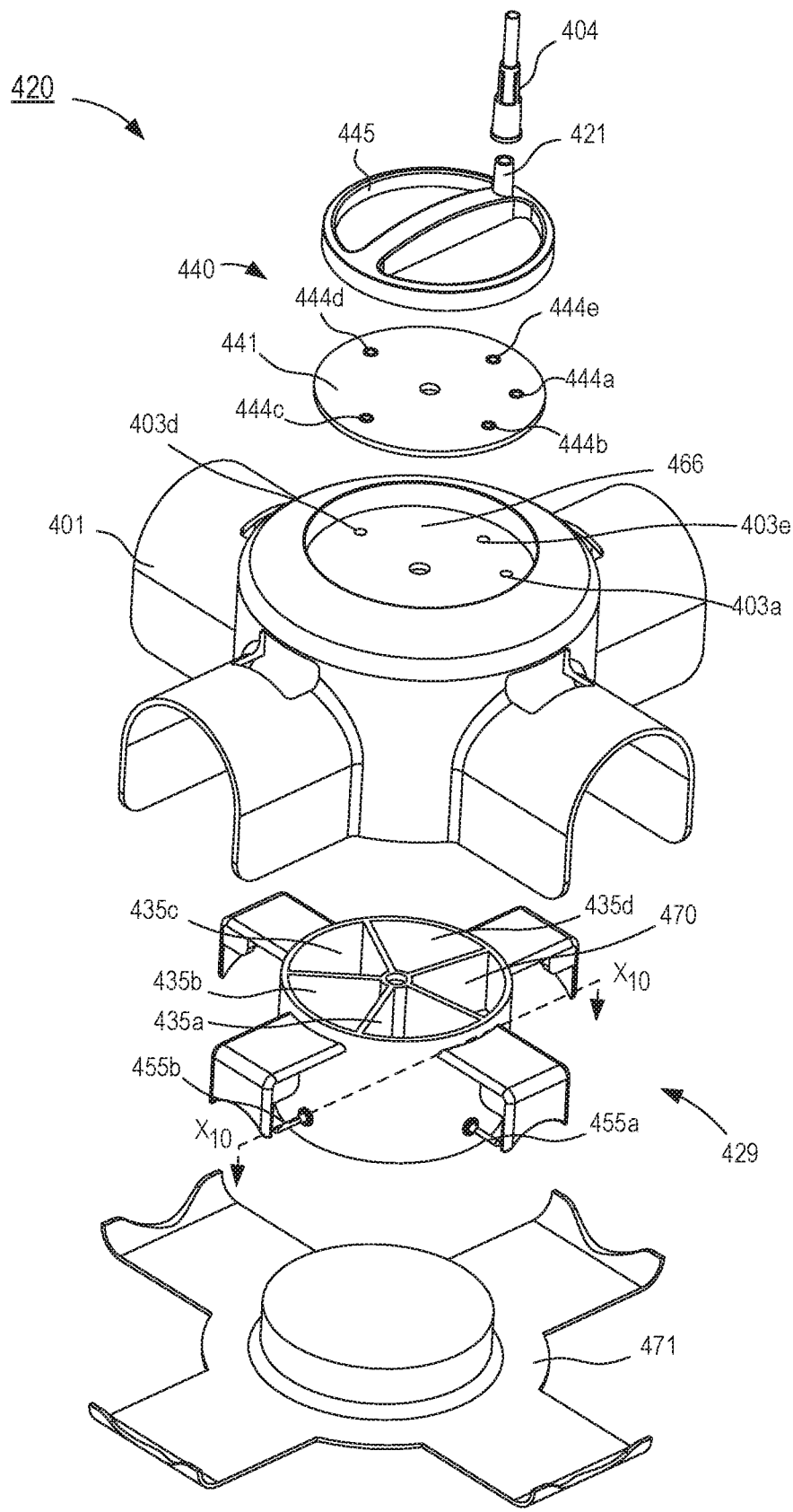
FIG. 22 is an exploded perspective view of a diversion mechanism included in the bodily-fluid collection device of FIG. 21.
Figure 23:
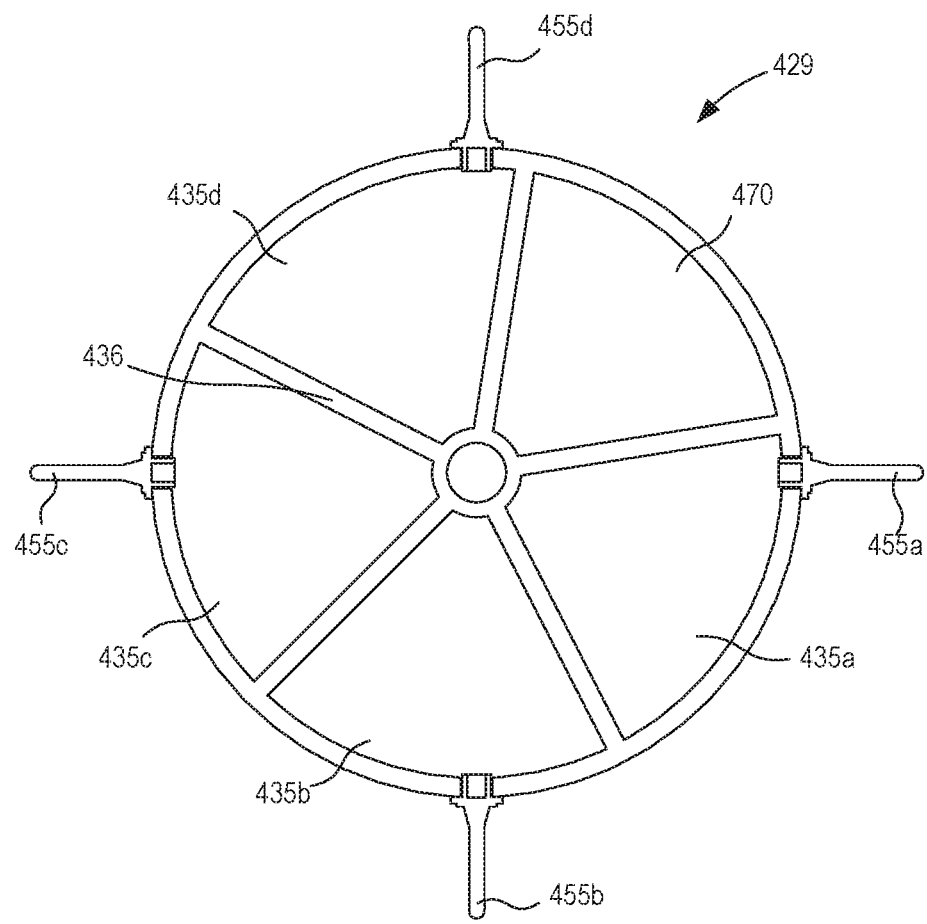
FIG. 23 is a cross-sectional view of a distribution member included in the diversion mechanism of FIG. 22 taken along the line $X_{10}$-$X_{10}$.

As shown in FIGS. 22 and 23, the distribution member 429 defines a chamber or volume that forms at least a portion of the pre-sample reservoir 470. The pre-sample reservoir 470 is configured to contain bodily-fluids such as, for example, blood, plasma, urine, and/or the like. The first outlet aperture 403a of the housing 401 can be substantially aligned with an open portion of the pre-sample reservoir 470 to allow the pre-sample reservoir 470 to receive a flow of bodily-fluid from the patient, as described in detail above. Expanding further, the distribution member 429 includes a set of walls 436 that can, for example, divide an inner volume of the distribution member 429 into portions and/or volumes that are fluidically isolated from one another. For example, as shown in FIG. 23, the set of walls 436 can divide an inner volume of the distribution member 429 into the pre-sample reservoir 470, the first fluid chambers 435a, the second fluid chamber 435b, the third fluid chamber 435c, and the fourth fluid chamber 435d. In some embodiments, the walls 436 can define and/or form the pre-sample reservoir 470 and the fluid chambers 435a-435d equally. In other embodiments, the pre-sample reservoir 470 can have define a volume that is different from a volume defined by the fluid chambers 435a-435d.

The distribution member 429 further includes a first piercing member 455a, a second piercing member 455b, a third piercing member 455c, and a fourth piercing member 455d that are in fluid communication with the first fluid chamber 435a, the second fluid chamber 435b, the third fluid chamber 435c, and the fourth fluid chamber 435d, respectively. As such, the piercing members 455a-455d can be used to puncture a vacuum seal of the sample reservoirs 480 and 490 (and corresponding sample reservoirs not shown in FIGS. 21-27) which can initiate a flow of bodily-fluid, as described in further detail herein.

The flow controller 440 of the collection device 400 includes a dial 445 and a seal member 441. The seal member 441 is disposed in the recess 466 of the housing 401 (see e.g., FIGS. 25 and 27). More particularly, the flow controller 440 can be coupled to the housing 401 such that the seal member 441 is disposed between and in contact with a surface of the housing 401 defining the recess 466 and a surface of the dial 445. The seal member 441 can be configured to form a substantially fluid tight seal with the surface of the dial 445 and the surface of the housing 401 that defines the recess 466, as described in detail above. As shown in FIG. 22, the seal member 441 defines a first aperture 444a, a second aperture 444b, a third aperture 444c, a fourth aperture 444d, and a fifth aperture 444e. The arrangement of the seal member 441 is such that when the seal member 441 is disposed in the recess 466, the first aperture 444a, the second aperture 444b, the third aperture 444c, the fourth aperture 444d, and the fifth aperture are substantially aligned with the first outlet aperture 403a, the second outlet aperture 403b, the third outlet aperture 403c, the fourth outlet aperture 403d, and the fifth outlet aperture 403e of the housing 401, respectively.

The dial 445 of the flow controller 440 is rotatably coupled to the housing 401 and movable between a first position, a second position, a third position, a fourth position, and a fifth position relative to the housing 401. The dial 445 includes an inlet port 421 that can be fluidically coupled to a medical device (either directly or indirectly via an adapter 404) that defines a fluid flow pathway for withdrawing and/or conveying bodily-fluid from a patient to the collection device 400. In this manner, the inlet port 421 can be configured to selectively place the pre-sample reservoir 470, the first sample reservoir 480, the second sample reservoir 480', the third sample reservoir 490, and the fourth sample reservoir 490' in fluid communication with the patient, as described in further detail herein. When the dial 445 is in the first position, the flow controller 440 is placed in a first configuration and the inlet port 421 can be substantially aligned with the first aperture 444a of the seal member 441 and the first outlet aperture 403a of the housing 401. In this manner, first aperture 444a of the seal member 441 establishes fluid communication between the inlet port 421 and the first outlet aperture 403a while fluidically isolating the inlet port 421 from the outlet apertures 403b, 403c, 403d, and 403e which in turn, fluidically isolates the inlet port 421 from the fluid chambers 435a-335d. When the dial 445 is rotated (or actuated) to the second position, the flow controller 440 is placed in a second configuration and the second outlet aperture 444b establishes fluid communication between the inlet port 421 and the second outlet aperture 403b while fluidically isolating the inlet port 421 from the pre-sample reservoir 470 and the fluid chambers 435b-435d. The collection device 400 works in a similar manner when the dial 445 is rotated to the third, fourth and fifth positions. Thus, when the inlet port 421 is placed in fluid communication with the patient (e.g., via the medical device coupled to the inlet port 421), the first outlet aperture 403a, the second outlet aperture 403b, the third outlet aperture 403c, the fourth outlet aperture 403d, and the fifth outlet aperture 403e can be selectively placed in fluid communication with the inlet port 421 to allow all the bodily-fluid to flow into at least one of the pre-sample reservoir 470, first sample reservoir 480, or the second sample reservoir 490 (or any other fluid reservoir coupled thereto).

In some embodiments, the housing 401 can selectively limit movement of the dial 445 from its first position to its second, third, fourth, and fifth positions. In some other embodiments, the housing 401 can be configured to prevent movement of the dial once it has been moved to the fifth position. Said another way, the housing 401 can include a locking mechanism to that prevents the dial 445 from being moved from the fifth position back to the first position. This feature can reduce the risk of contaminating the bodily-fluid collected in the flow chambers 435a-435d and/or sample reservoirs 480 and 490 from the bodily-fluid contained in the pre-sample reservoir 470 (which has a high risk of containing surface bound microbes and/or other undesirable external contaminants). This locking mechanism can also protect health care practitioners from exposure to blood-borne pathogens in patient samples which can include HIV, Hepatitis C, etc. The dial 445 and/or the housing 401 can also include mechanical detents and/or other indicators that provide visual or tactile feedback to ensure precise positioning of the dial 445 with respect to the outlet port 403a and outlet apertures 403a-403d in the housing 401.

Similar to the collection device 300 presented in FIGS. 14-20, the collection device 400 includes a pre-sample reservoir 470 that is a chamber contained within and/or otherwise defined by the distribution member 429. The pre-sample reservoir 470 can contain bodily-fluids such as, for example, blood, plasma, urine, and/or the like. The pre-sample reservoir 470 is configured to be fluidically coupled to the first outlet port 403a of the collection device 400 (located in the housing 401). During operation of the collection device 400, when the flow controller 440 is in the first position, bodily-fluid is drawn from a part of the body of a patient (e.g., a vein) into the pre-sample reservoir 470, the aperture for the pre-sample reservoir 444a located in the seal member 441, and the first outlet port 403a, via the inlet port 421. The pre-sample reservoir 470 is configured to contain the first amount of the bodily-fluid withdrawn from the patient, where the first amount of bodily-fluid can be a pre-determined or undetermined amount, such that the first amount of bodily-fluid is fluidically isolated from a second and/or third and/or fourth and/or fifth amount of the bodily-fluid that is subsequently withdrawn from the patient.

Figure 24:
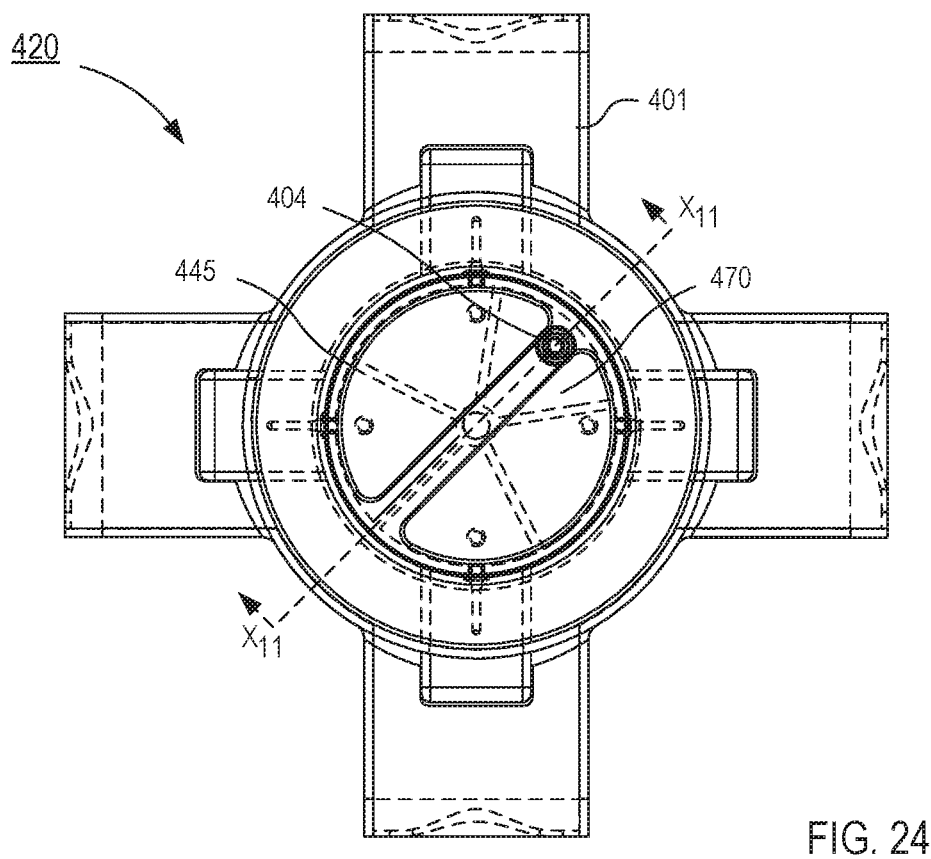
FIG. 24 is a top view of a portion of the bodily-fluid collection device of FIG. 21 in a first configuration.
Figure 25:
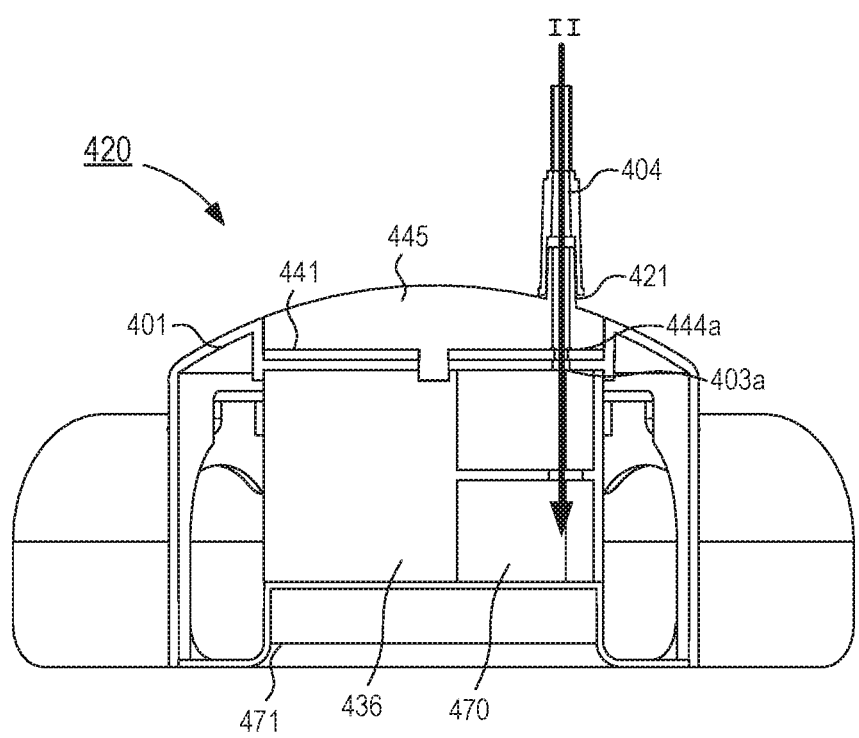
FIG. 25 is a cross-sectional view of the portion the bodily-fluid collection device of FIG. 24 in the first configuration, taken along the line $X_{11}$-$X_{11}$.

In operation, the collection device 400 can be used to collect bodily-fluids (e.g., blood, plasma, urine, etc.) from a patient with reduced contamination. For example, the inlet port 421 of the collection device 400 can be fluidically coupled to a needle or other lumen-defining device (e.g., flexible sterile tubing). Following venipuncture, the dial 445 is rotated until it reaches the first position, as shown in FIGS. 24 and 25. Alternatively, the dial 445 can be pre-set in the first position and the collection device 400 can be otherwise sealed to preserve the sterility of the collection device 400, as described above. With the dial 445 in the first position, the flow controller 440 is placed in a first configuration and the first outlet aperture 444a of the seal member 441 establishes fluid communication between the inlet port 421 and the first outlet port 403a (contained within the housing 401) while fluidically isolating the inlet port 421 from the four sample flow channels 435a-435d. In this first configuration, the bodily-fluid flows from the portion of the body of the patient through the inlet port 421, the first outlet aperture 444a of the seal member 441, the first outlet port 403a of the housing 401, and into the pre-sample reservoir 470 defined by the distribution member 470, as indicated by the arrow II in FIG. 25. Thus, a first amount (pre-determined or undetermined) of bodily-fluid can be received into the pre-sample reservoir 470 immediately after venipuncture and isolated from subsequent samples, as described in detail above.

Figure 26:
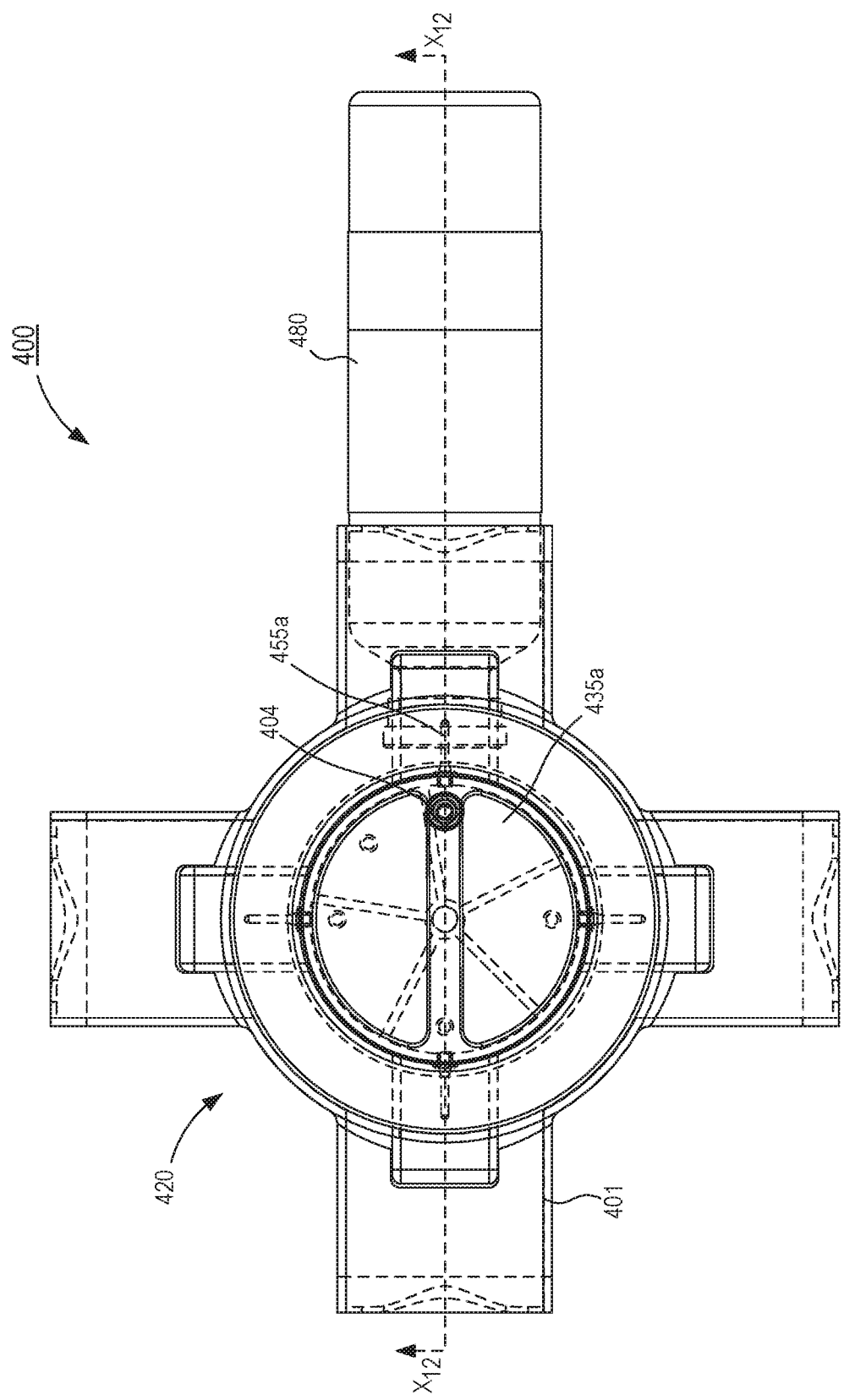
FIG. 26 is a top view of the bodily-fluid collection device of FIG. 21 in a second configuration.
Figure 27:
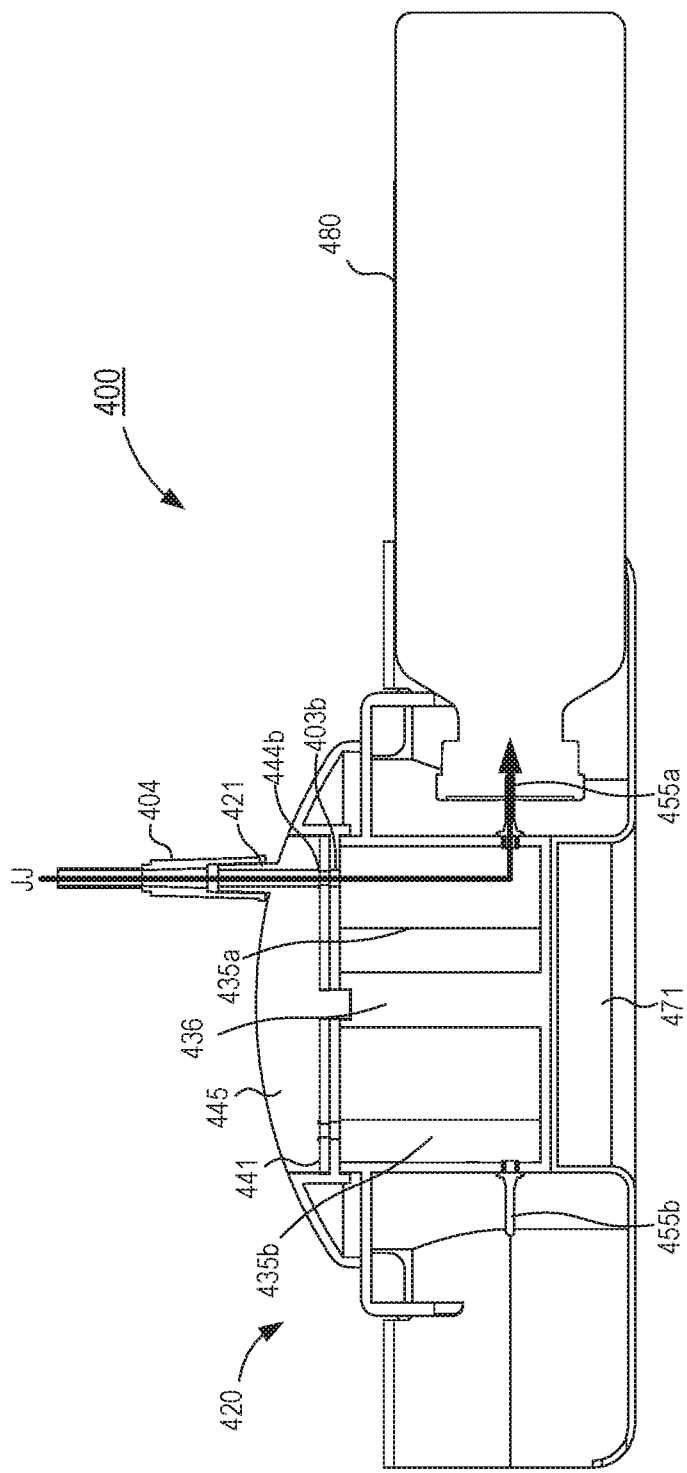
FIG. 27 is a cross-sectional view of the bodily-fluid collection device of FIG. 21 in the second configuration, taken along the line $X_{12}$-$X_{12}$ in FIG. 26.
Figure 28:
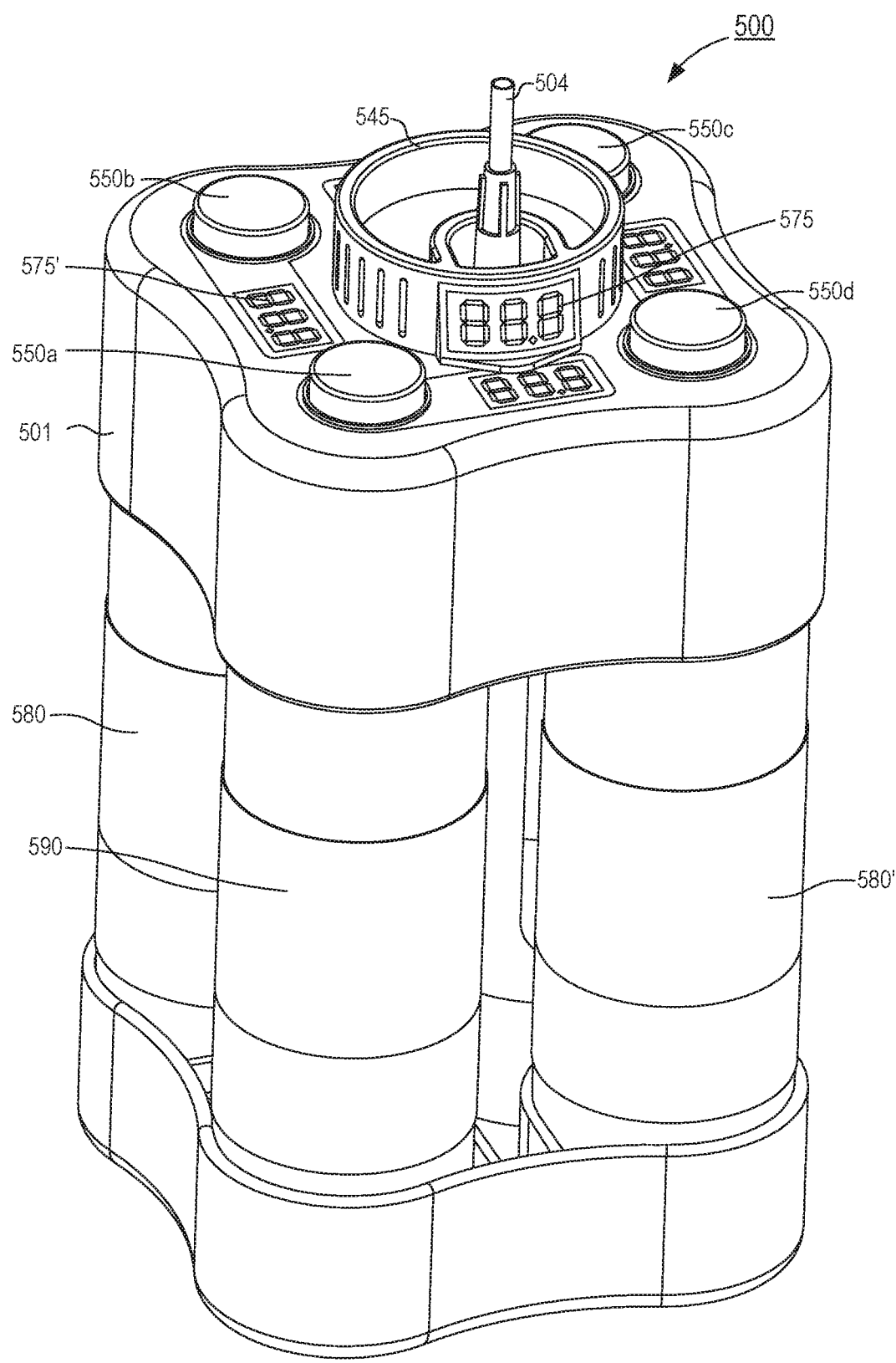
FIG. 28 is a perspective view of a bodily-fluid collection device in a first configuration according to an embodiment.

Following collection of the bodily-fluid pre-sample in the pre-sample reservoir 470, the dial 445 can be actuated (or rotated) until it reaches the second position as shown in FIGS. 26 and 27. When the dial 445 is in the second position, the flow controller 440 is placed in a second configuration and the second outlet aperture 444a of the seal member 441 establishes fluid communication between the inlet port 421 and the first fluid chamber 435a while fluidically isolating the pre-sample reservoir 470 from the inlet port 421. Once the first fluid chamber 435a is filled with the bodily-fluid, the flow controller 440 can be moved to a third position to isolate and seal the first fluid channel 435a from an external environment. Additionally, the sample reservoir 480 can be actuated from the first configuration to the second configuration to transfer the bodily-fluid from the first fluid chamber 435a to the sample reservoir 480. For example, the sample reservoir 480 can be actuated (pushed against the piercing member 455a) from the first configuration to the second configuration by the user, or automatically, to establish fluid communication between a part of the body of a patient (e.g., a vein) and the sample reservoir 480. As described above, moving the sample reservoir 480 to the second configuration causes the piercing member 455a to puncture the vacuum seal of the sample reservoir 480, and be disposed inside the sample reservoir 480. In the second configuration, the part of the body of a patient (e.g., a vein) is exposed to vacuum suction from the sample reservoir 480 due to the negative pressure conditions (vacuum) that in certain embodiments exist inside the sample reservoir 480. Thus, bodily-fluid flows from the part of the body of the patient through the inlet port 421, the second outlet aperture 444b of the seal member 441, the second outlet aperture 403b of the housing 401, the second fluid chamber 435b, and into the first sample reservoir 480, as indicated by the arrow JJ in FIG. 27.

Once a desired volume of bodily-fluid (e.g., the second amount) is collected in the sample reservoir 480, the user can actuate (rotate) the flow controller 440 to the third position and/or move the sample reservoir 480 back to its first configuration to isolate the first sample reservoir 480 from the inlet port 421. When the sample reservoir 480 is back in the first configuration, the piercing member 455a is removed from the sample reservoir 480 and the seal of the sample reservoir 480 (e.g., a self sealing septum) fluidically isolates the first sample reservoir 480 from the second fluid chamber 435b and the external environment. Filling the other sample reservoirs is done in an identical manner with the flow controller 440 in the third, fourth and fifth configurations respectively.

Although the distribution member 429 of the collection device 400 is shown and described above as including the set of walls 436 separating the different fluid chambers 435a-435d (see e.g., FIG. 23), in other embodiments, the distribution member 429 can include and/or define a single fluid chamber or the like. In such embodiments, the distribution member 429 is divided between a pre-sample reservoir 470 and a combined fluid chamber 435 (i.e. the fluid chambers are not separated into four separate sections by the walls 436). In such embodiments, the user can fill all four sample reservoirs at one time by actuating (rotating) the dial 445 to either the second, third, fourth or fifth positions.

Any of the embodiments described herein can be used with, for example, a metering device that can be used to meter (e.g., quantify) a flow of bodily-fluid into a pre-sample reservoir and/or a sample reservoir. In some instances, laboratory standard practices do not ensure consistent compliance with accurate inoculation volumes of bodily-fluids (e.g., blood specimens) due to the fact that the fill volume is visually determined by the clinician and/or phlebotomist and is thus subject to human error. The fact that the volume indicators on the blood collection bottle are difficult to read when being held and that often the collection bottle is not held upright during the draw procedure can contribute to inaccurate volumes of a bodily-fluid sample received from a patient. Insufficient sample volumes (e.g., below the manufacturer's recommendation) can decrease the sensitivity of culture tests, leading to false-negative results. Additionally, fill volumes above manufacturer's recommendations can cause false-positivity as is indicated in overview materials and instructions for use for specific types of testing supplies and apparatuses (e.g., blood culture bottles designed for use with automated microbial detection systems produced by manufacturers such as Becton Dickinson, Franklin Lakes, N.J.). Thus, flow metering and volume display features can allow a lab technician and/or a health care practitioner (e.g. phlebotomist) to confirm the volume of bodily-fluid that is collected into each individual sample reservoir before placing the sample reservoirs in an incubator or into other laboratory test equipment depending on how the sample needs to be processed. The lab technician and/or phlebotomist can also record (e.g., in a medical record, database, spreadsheet, etc.) the precise volume information for a clinician to evaluate when results are received, thereby helping reduce the possibility of misinterpretation of false-negative and/or false-positive results.

FIGS. 28-35 illustrate a collection device 500 according, to an embodiment. The collection device 500 includes a diversion mechanism 520, a flow controller 540, and sample reservoirs 580, 580', 590 and 590'. As further described herein, the collection device 500 can be moved between a first, a second, a third, a fourth, and a fifth configuration to deliver a flow of a bodily-fluid that is substantially free from microbes exterior the body, such as, for example, dermally residing, microbes and/or other undesirable external contaminants. The collection device 500 can be any suitable shape, size, or configuration. For example, aspects and/or portions of the collection device 500 can be substantially similar in form and/or function as corresponding aspects and/or portions of any of the collection devices 100, 200, 300, and/or 400 described above. Thus, such similar aspects and/or portions are, not described in further detail herein. By way of example, in some embodiments, the sample reservoirs 580, 580', 590, and 590' of the collection device 500 can be substantially similar and/or the same in form and function as the sample reservoirs 380, 380', 390, and 390', respectively, included in the collection device 300 of FIGS. 14-20.

The diversion mechanism 520 includes a housing 501, a distribution member 529, and movable members 550a, 550b, 550c, and 550d. The housing 501 is physically and fluidically coupled to the distribution member 529, and provides and/or defines a set of fluid flow pathways for collecting bodily-fluids from the patient. The housing 501 includes a set of displays 575' (e.g., liquid crystal displays (LCDs) or the like) that can be included in and/or otherwise coupled (e.g., electrically and/or mechanically) to a flow metering device, as described in further detail herein. The housing 501 defines a recess 566, outlet apertures 503a, 503b, 503c, 503d, 503e, and movable member openings 550a, 550b, 550c, 550d (also referred to herein as "openings"). The recess 566 is configured to receive a seal member 541 included in the flow controller 540, as described in further detail herein. The first outlet aperture 503a, the second outlet aperture 503b, the third outlet aperture 503c, the fourth outlet aperture 503d, and the fifth outlet aperture 503e are each configured to define a different fluid flow path in fluid communication with different portions of the distribution member 529. More specifically, the distribution member 529 defines and/or forms at least a portion of a pre-sample reservoir 570 in fluid communication with the first outlet aperture 503a, and a first flow channel 535a in fluid communication with the second outlet aperture 503b, second flow channel 535b in fluid communication with the third outlet aperture 503b, a third flow channel 535c in fluid communication with the fourth outlet aperture 503d, and a fourth flow channel 535 in fluid communication with the fifth outlet aperture 503e.

Figure 29:
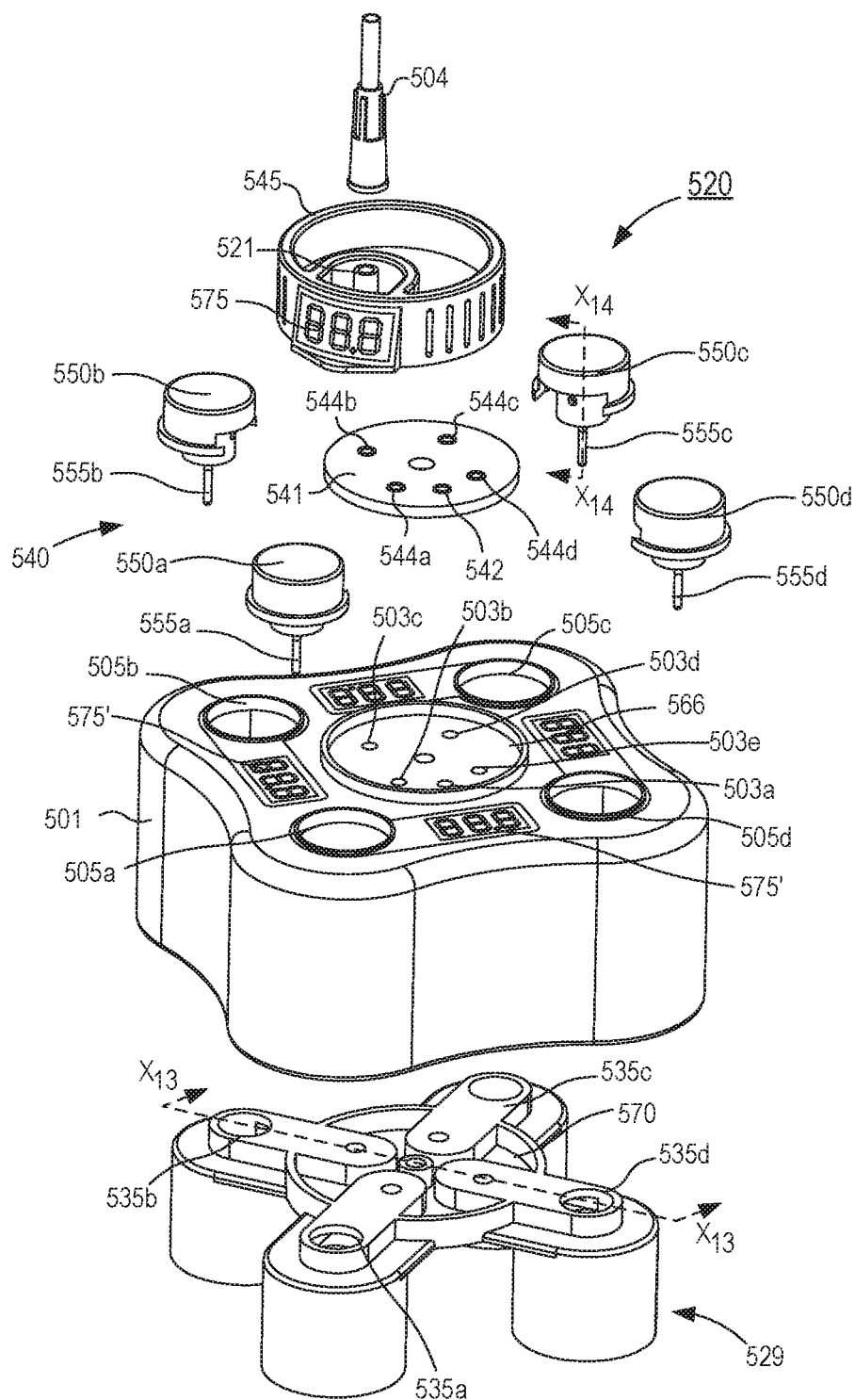
FIG. 29 is an exploded perspective view of a portion of the bodily-fluid collection device of FIG. 28.
Figure 30:
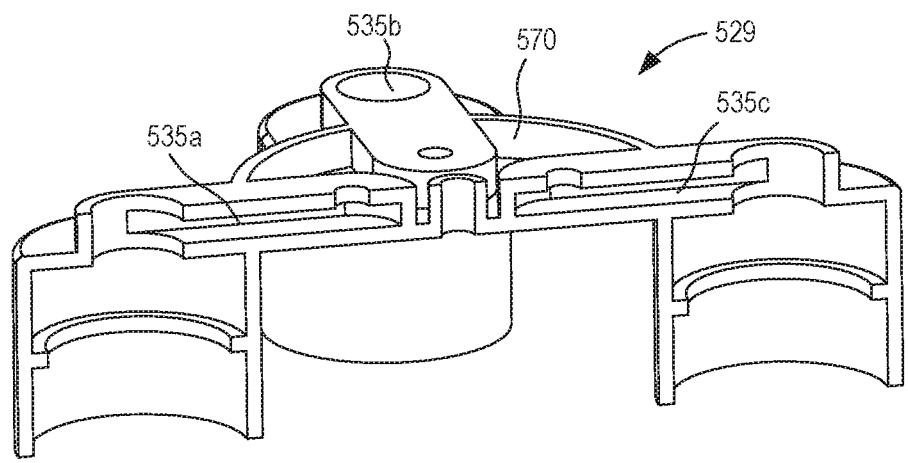
FIG. 30 is a cross-sectional side view of a distribution member included in the bodily-fluid collection device of FIG. 28, taken along the line $X_{13}$-$X_{13}$ in FIG. 29.

As shown in FIGS. 29 and 30, the distribution member 529 defines a chamber or volume that defines at least a portion of the pre-sample reservoir 570. The pre-sample reservoir 570 is configured to contain bodily-fluids such as, for example, blood, plasma, urine, and/or the like. The first outlet aperture 503a of the housing 501 can be substantially aligned with an open portion of the pre-sample reservoir 570 to allow the pre-sample reservoir 570 to receive a flow of bodily-fluid from the patient, as described in detail above with reference to the pre-sample reservoir 370 in FIGS. 14-20. The flow channels 535a-535d extend radially from a center of the distribution member 529 and are arranged such that each flow channel 535a, 535b, 535c, and 535d is fluidically isolated from the pre-sample reservoir 570 and the other flow channels. In this manner, the flow channels 535a, 535b, 535c, and 535d can direct and/or otherwise define a fluid flow path between a first end portion that defines an opening substantially aligned with the outlet apertures 503b, 503c, 503d, and 503e, respectively, and a second end portion that defines an opening or port configured to receive the movable members 550a, 550b, 550c, and 550d, respectively. Although the distribution member 529 is shown in FIGS. 29 and 30 as including flow channels 535a-535d that are substantially closed, in other embodiments, the flow channels 535a-535d can be substantially open as shown and described above with reference to the distribution member 329 of FIGS. 15 and 16. As such, the distribution member 529 of the collection device 500 can function in a substantially similar manner as the distribution member 329 of the collection device 300.

The movable members 550a, 550b, 550c, and 550d are movably disposed in the openings 505a, 505b, 505c, and 505d, respectively, of the housing 501 and the corresponding openings defined by the second end portion of the distribution member 529. Although not shown in FIGS. 28-35, in some embodiments, the movable members 550a, 550b, 550c, and 550d can be operably coupled to a bias member or the like, as described in detail above with reference to the movable members 250 and 250' of the collection device 200. In this manner, the movable members 550a, 550b, 550c, and 550d can be actuated (e.g., moved) by the user from a first position and a second position relative to the housing 501 and distribution member 529 to direct fluid flow into the first sample reservoir 580, the second fluid reservoir 580', the third fluid reservoir 590, and the fourth sample reservoir 590', respectively. The movable members 550a, 550b, 550c, and 550d are substantially the same and therefore are described with reference to a single movable member 550 in FIG. 31. Moreover, portions of the movable member 550 can be substantially similar to the movable member 250 described above. Thus, portions of the movable member 550 are not described in further detail herein. The movable member 550 defines an inner cavity 552 that is in fluid communication with an inlet port 553 and a piercing member 555. The piercing member is substantially similar to those described in detail above. The inlet port 553 extends through a set of walls that defines the inner chamber 552 to selectively place the inner volume 552 of the movable member 550 in fluid communication with the corresponding flow channel 535a, 535b, 535c, or 535d.

Figure 31:
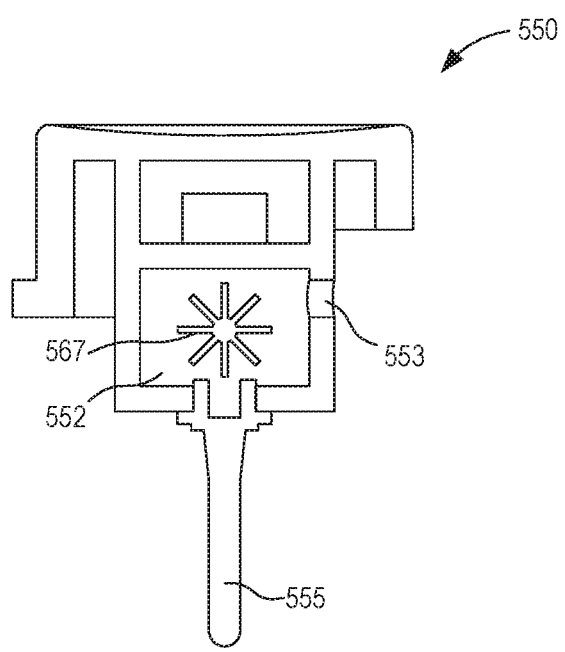
FIG. 31 is a cross-sectional view of a movable member included in the bodily-fluid collection device of FIG. 28, taken along the line $X_{14}$-$X_{14}$ in FIG. 29.

As shown in FIG. 31, the movable member 550 includes a flow control mechanism 567 rotatably disposed in the inner volume 552 and in substantially direct fluid communication with the inlet port 553. The flow metering mechanism 567 can be, for example, a wheel or the like that can include a set of spokes or fins (e.g., a turbine or the like). In this manner, bodily-fluid can enter the inlet port 553 of the movable member 550 and flow past the flow metering device 567, which in turn, can result in a rotation of the flow metering device 567 relative to the movable member 550. Thus, characteristics of the rotation of the flow metering device 567 can be operable in determining a volume of bodily-fluid transferred to the inner volume 552 of the movable member 550, a volumetric flow rate, and/or the like. Although not shown in FIGS. 28-35, the flow control mechanism 567 of the movable member 550 is operably coupled to the display 575' of the housing 501. Thus, as bodily-fluid is transferred, for example, to the sample reservoirs 580, 580', 590, and/or 590', volumetric information associated with the flow of bodily-fluid can be presented on the displays 575'. In this manner, a user can manipulate the collection device 500 to collect a bodily-fluid sample from a patient and can visualize at least one of the displays 575' to determine a precise volume of the bodily-fluid sample transferred to, for example, the sample reservoir 580.

The flow controller 540 of the collection device 500 includes a dial 545 and a seal member 541. The seal member 541 is disposed in the recess 566 of the housing 501. More particularly, the flow controller 540 can be coupled to the housing 501 such that the seal member 541 is disposed between and in contact with a surface of the housing 501 defining the recess 566 and a surface of the dial 545. The seal member 541 can be configured to form a substantially fluid tight seal with the surface of the dial 545 and the surface of the housing 501 that defines the recess 566, as described in detail above. As shown in FIG. 29, the seal member 541 defines a first aperture 544a, a second aperture 544b, a third aperture 544c, a fourth aperture 544d, and a fifth aperture 544e. The arrangement of the seal member 541 is such that when the seal member 541 is disposed in the recess 566, the first aperture 544a, the second aperture 544b, the third aperture 544c, the fourth aperture 544d, and the fifth aperture 544e are substantially aligned with the first outlet aperture 503a, the second outlet aperture 503b, the third outlet aperture 503c, the fourth outlet aperture 503d, and the fifth outlet aperture 503e of the housing 501, respectively.

The dial 545 of the flow controller 540 is rotatably coupled to the housing 501 and movable between a first position, a second position, a third position, a fourth position, and a fifth position relative to the housing 501. The dial 545 includes an inlet port 521 that can be fluidically coupled to a medical device (either directly or indirectly via an adapter 504) that defines a fluid flow pathway for withdrawing and/or conveying bodily-fluid from a patient to the collection device 500. In this manner, the inlet port 521 can be configured to selectively place the pre-sample reservoir 570, the first sample reservoir 580, the second sample reservoir 580', the third sample reservoir 590, and the fourth sample reservoir 590' in fluid communication with the patient, as described in further detail herein. The dial 545 can be configured to rotate through the first position, the second position, the third position, the fourth position, and the fifth position in a substantially similar manner as described above with reference to the dial 345 of the collection device 300 and is therefore, not described in further detail herein.

As shown, the dial 545 can further include a display 575 that can be configured to present volumetric information associated with a flow of bodily-fluid. For example, although not shown in FIGS. 28-35, the dial can include a flow metering device or the like such as the flow metering device 567 included in the movable member 550. In this manner, the flow metering device can meter a flow of bodily-fluid through, for example, the inlet port 521 and can be operably coupled to the display 575 such that volumetric information associated with the flow of bodily-fluid through the inlet port 521 is presented on the display 575 of the dial 545.

Figure 32:
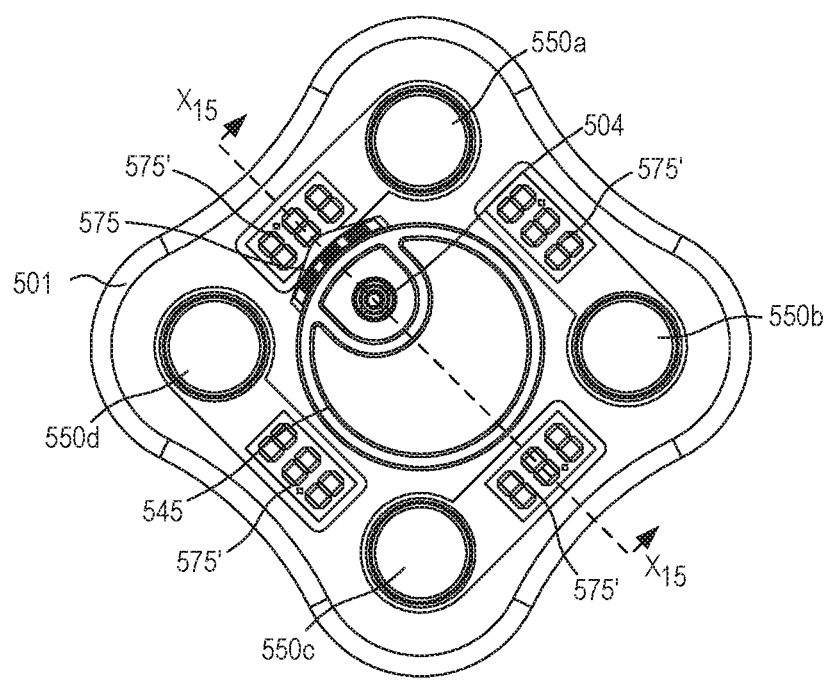
FIG. 32 is a top view of the bodily-fluid collection device of FIG. 28 in a first configuration.
Figure 33:
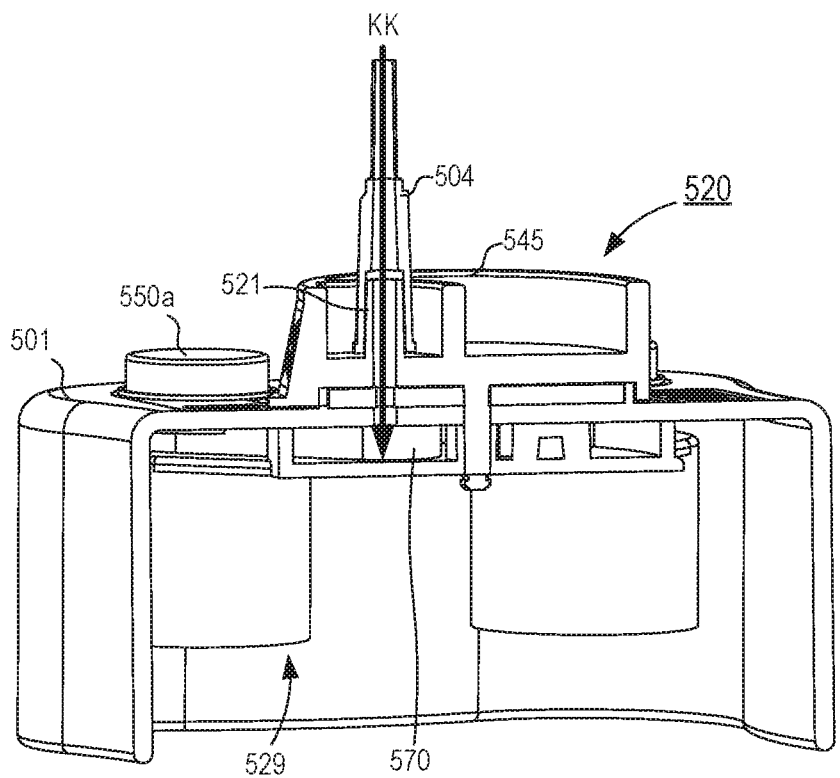
FIG. 33 is a cross-sectional view of a portion the bodily-fluid collection device of FIG. 21 in the first configuration, taken along the line $X_{15}$-$X_{15}$ in FIG. 32.

In operation, the collection device 500 can be used to collect bodily-fluids (e.g., blood, plasma, urine, and/or the like) from a patient with reduced contamination. For example, the inlet port 521 of the collection device 500 can be fluidically coupled to a needle or other lumen-defining device (e.g., flexible sterile tubing). Following venipuncture (or other method of accessing bodily-fluid), the dial 545 is actuated (or rotated) until it reaches the first position, as shown in FIGS. 32 and 33. Alternatively, the dial 545 can be pre-set in the first position and the collection device 500 can be otherwise sealed to preserve the sterility of the collection device 500.

As described above, when the dial 545 is in the first position, the flow controller 540 is placed in the first configuration and the first aperture 544*a* of the seal member 541 establishes fluid communication between the inlet port 521 and the first outlet port 530 (contained within the housing 501) while fluidically isolating the inlet port 521 from the four flow channels 535*a*-535*d*. Additionally, the sample reservoirs 580, 580', 590 and 590' are fluidically isolated from the inlet port 521 in the first configuration and a fluid flow path is defined between a portion of the body of a patient (e.g. a vein) and the pre-sample reservoir 570 as indicated by the arrow KK in FIG. 33. In this first configuration, the bodily-fluid flows (e.g., by gravitation force, vacuum, etc.) from the portion of the body of the patient through the inlet port 521, the first aperture 544*a* of the seal member 541, the first outlet port 503*a* of the housing 501, and into the pre-sample reservoir 570. In the first configuration, the flow controller 540 also fluidically isolates the pre-sample reservoir 570 from the flow channels 535*a*-535*d*. Thus, a first amount (predetermined or undetermined) of bodily-fluid can be received into the pre-sample reservoir 570 immediately after venipuncture and isolated from subsequent samples. In this manner, the collection device 500 can be used to prevent the first amount of bodily-fluid, which is most likely to contain bodily surface microbes and/or other undesirable external contaminants, from contaminating subsequent amounts of the bodily-fluid samples that are collected and used for diagnostic or other testing that can be impacted by the contaminants. Moreover, the display 575 can present, for example, information received from the flow control mechanism (not shown) that is associated with a volume of bodily-fluid transferred to the pre-sample reservoir 570. Thus, a precise volume of bodily-fluid can be transferred to and fluidically isolated within the pre-sample reservoir.

Figure 34:
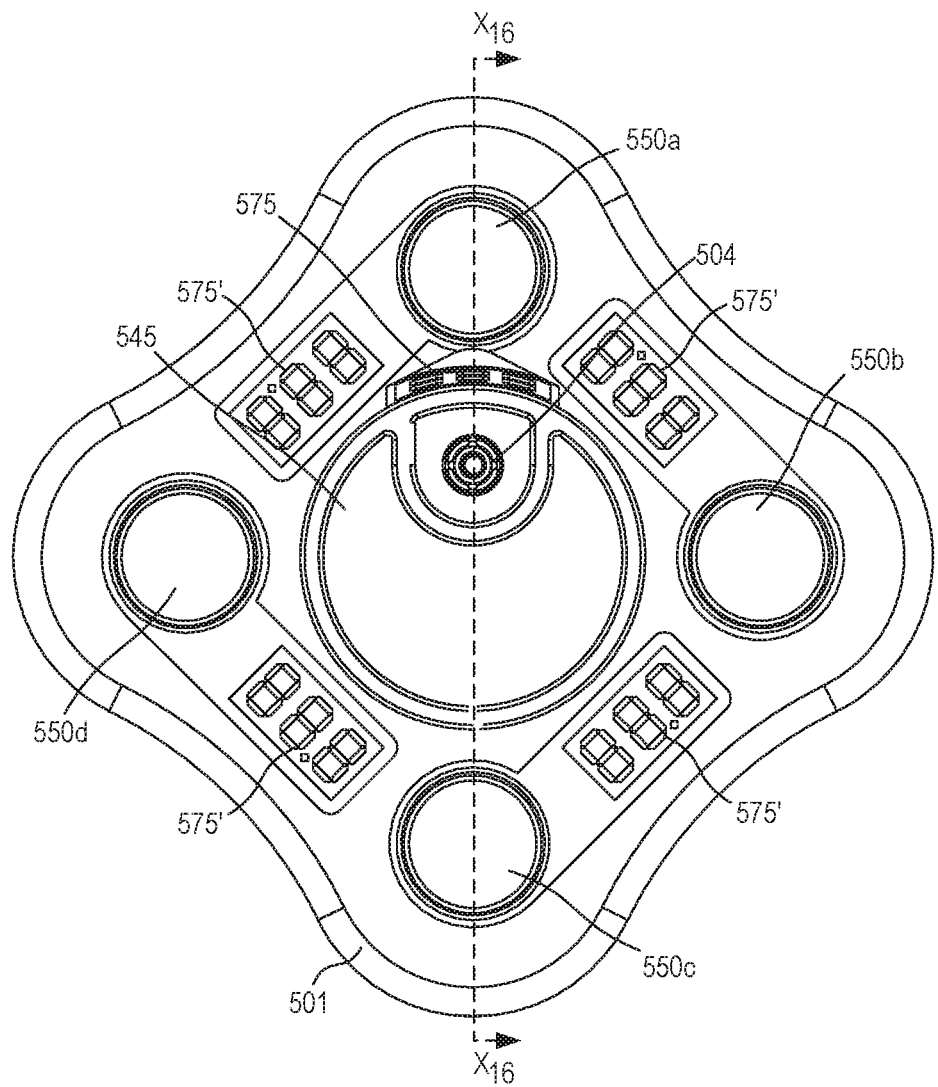
FIG. 34 is a top view of the bodily-fluid collection device of FIG. 28 in a second configuration.
Figure 35:
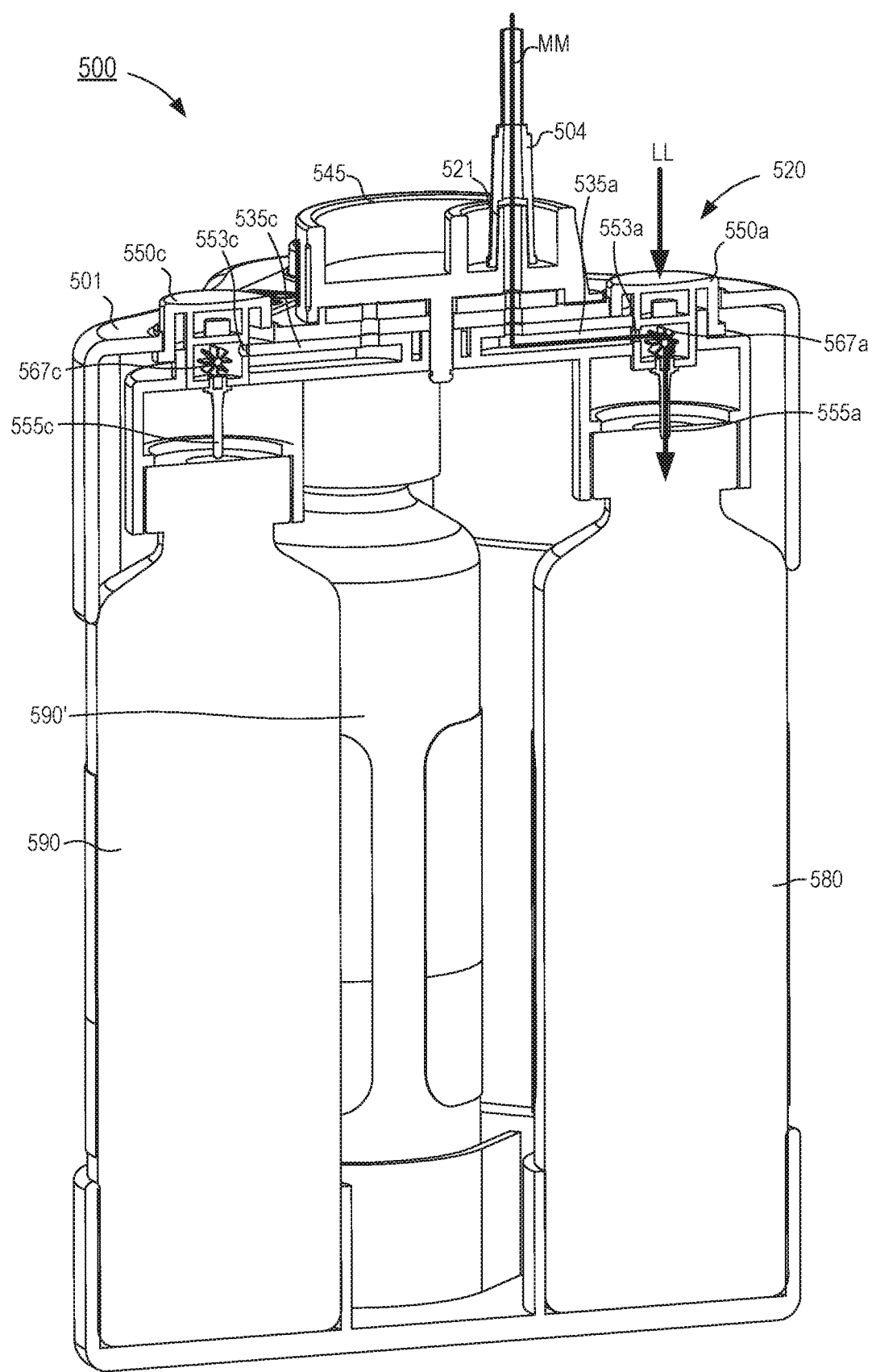
FIG. 35 is a cross-sectional view of the bodily-fluid collection device of FIG. 28 in the second configuration, taken along the line $X_{16}$-$X_{16}$ in FIG. 34.

Following collection of the bodily-fluid pre-sample in the pre-sample reservoir 570, the dial 545 can be actuated (or rotated) until it reaches the second position as shown in FIGS. 34 and 35. When the dial 545 is in the second position, the flow controller 540 is placed in the second configuration and the second aperture 544*b* of the seal member 541 establishes fluid communication between the inlet port 521 and the flow channel 535*a*, while fluidically isolating the pre-sample reservoir 570 from the inlet port 521. With the flow controller 540 in the second configuration, the movable member 550*a* can be actuated (i.e., depressed) from the first position to the second position by the user to establish fluid communication between the patient (e.g., a vein) and the first sample reservoir 580. More specifically, the movable member 550 is moved from its first position to its second configuration to pass the piercing member 555 through a vacuum seal of the first sample reservoir 580 to be disposed therein, as indicated by the arrow LL in FIG. 35.

While in the second position, the inlet port 553 of the movable member 550 is substantially aligned with, and in fluid communication with, the first flow channel 535*a*, which allows the bodily-fluid to flow from the first flow channel 535*a*, into the inner cavity 552 of the movable member 550, and out of the piercing member 555 into the first sample reservoir 580. The pressure differential between the sample reservoir 580 (e.g., vacuum or negative pressure) and the first flow channel 535*a* draws the bodily-fluid into the sample reservoir 580. Said another way, in the second configuration, the flow controller 540 and the movable member 550*a* establish a fluid flow path between the inlet port 521 of the dial 545 and the first sample reservoir 580, as indicated by the arrow MM in FIG. 35. Moreover, the flow of bodily-fluid through the movable member 550*a* rotates the flow metering mechanism 567 relative to the movable member 550. Thus, the rotation of the flow metering mechanism 567 can be operable in determining a volume of bodily-fluid sample transferred to the sample reservoir 580. In addition, the display 575' can present, for example, information received from the flow control mechanism 567 that is associated with a volume of bodily-fluid transferred to the sample reservoir 580. Therefore, a precise volume of bodily-fluid can be transferred to the sample reservoir 580. For example, in some instances, the collection device 500 can be used to collect three sample volumes of 20 mL each in the first sample reservoir 580, the second sample reservoir 580', and the third sample reservoir 590 (i.e., 60 mL of total sample volume collected).

Once a desired volume of bodily-fluid (e.g., the second amount) is collected in the first sample reservoir 580, the user can release the movable member 550 allowing the bias member (not shown) to move the back to its first position. With the movable member 550 back in its first position, the piercing member 555 is removed from the first sample reservoir 580 and the seal (e.g., a self sealing septum) fluidically isolates the first sample reservoir 580 from the inner flow channel 535. The collection device 500 can be used to transfer a second sample volume to the second sample reservoir 580', a third sample volume to the third sample reservoir 590, and a fourth sample volume to the fourth sample reservoir 590' in the same manner by rotating the dial 545 to its third position, fourth position, and fifth position, respectively.

In some instances, the bodily-fluid collection device 500 can allow a clinician and/or a phlebotomist to open the package containing the bodily-fluid collection device 500 and remove the only the housing 501 (that contains the distribution members) and take the housing 501 to a patient's bedside. The clinician and/or a phlebotomist can perform venipuncture (or employ any other method of accessing patient's bodily-fluid) on the portion of the body of a patient (e.g. a vein) using any standardized technique. Following venipuncture, the clinician and/or a phlebotomist can collect the total blood volume required for all samples. For example, the clinician and/or a phlebotomist can collect a 2.5 mL pre-sample diversion volume and a 10 mL sample volume for each of the four sample reservoirs that amounts to a total of 32.5 mL of collected bodily-fluid (e.g., blood). Following collection of the desired amount of bodily-fluid, the hypodermic needle can be removed from the portion of the body of a patient (e.g. a vein) and the clinician and/or a phlebotomist can place the housing 501 (that contains the bodily-fluid) on top of a 3-pack (or 2-pack) of pre-sterilized sample reservoirs with septum tops that are pre-positioned in a custom tray that matches the geometry of housing 501. By using such a pre-sterilized pack of sample reservoirs, the clinician does not need to perform the process step of "wiping" the top of the sample reservoirs with a sterilizing agent, thereby reducing the likelihood of contamination if, for example, the reservoir tops are improperly and/or insufficiently sterilized. The clinician and/or a phlebotomist can then activate the automated inoculation of the sample reservoirs with the bodily-fluid with precise volume control. In certain embodiments, after the inoculation of the sample reservoirs is complete, the entire device 500 with volume information displayed for each individual sample reservoir can be sent to the laboratory for analysis. It other embodiments, sample reservoirs 580 and/or 590 can be removed individually and sent to the laboratory for analysis.

Although, the collection device 500 is shown and described with reference to FIGS. 28-35 as including a set of displays 575 and 575' that can present volumetric data associated with a volume of bodily-fluid transferred through a portion of the collection device, in other embodiments, a collection device can include any suitable flow metering mechanism having any suitable output indicator. For example, in some embodiments, a display can include a set of three lights with a first light with low volume (e.g., 10 mL), a second light associated with medium volume (e.g., 20 mL), and a third light associated with high volume (e.g., 30 mL). In this manner, as a flow of bodily-fluid is transferred through the flow controller 540 and the diversion mechanism 520, and into, for example, the first movable member 550a, the flow metering mechanism included therein can send a signal or the like to the display that is operable in lighting the first light, the second light, and/or the third light according to a volume of bodily-fluid that is transferred through the movable member 550. In some embodiments, the movable members 550a, 550b, 550c, and 550d can be moved from a first position to a second, third, or fourth position, relative to the housing 501. In such embodiments, the positions can be associated with, for example, an intended volume of bodily-fluid to be transferred to a sample reservoir. For example, in some embodiments, a user can actuate (e.g., move) the movable member 550a from its first position to its second position. In such embodiments, the second position can be associated with, for example, a low volume of bodily-fluid (e.g., 10 mL) to be transferred to a sample reservoir. In some embodiments, the housing 501 and/or the movable member 550a can include a detent, lock, catch, protrusion, recess, and/or the like that can temporarily retain the movable member 550a in the second position until a predetermined volume of sample has been transferred to the sample reservoir. Moreover, once placed in the second position, the display can be configured to illuminate, for example, a light or the like associated with the predetermined volume to indicate to the user the volume of bodily-fluid to be transferred to the sample reservoir. Once the desired volume of bodily fluid is transferred to and fluidically isolated in the sample reservoir, the diversion mechanism 520 can be configured to automatically return the movable member 550a back to its first position. In this manner, the diversion mechanism 520 and the flow controller 540 can be physically and fluidically coupled to any number of sample reservoirs and used to transferred a precise volume of bodily-fluid to each sample reservoir.

Figure 36:
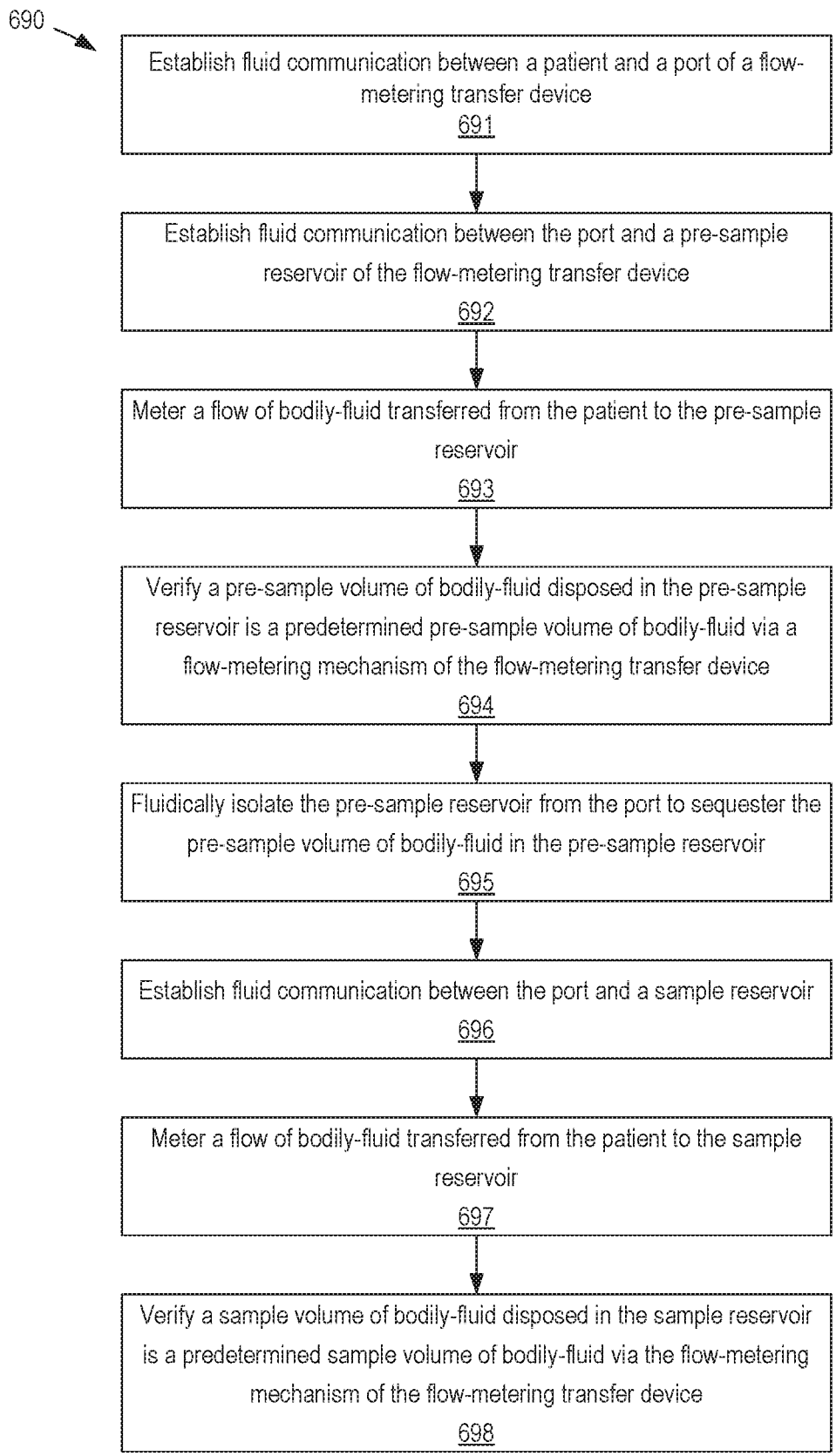
FIG. 36 is a flowchart illustrating a method of obtaining a bodily-fluid sample with reduced contamination using a collection device according to an embodiment.

FIG. 36 is a flowchart illustrating a method 690 of using a flow-metering transfer device to obtain a predetermined sample volume of a bodily-fluid from a patient. The flow metering transfer device can be any of the transfer devices (also referred to herein as "collection devices") described herein. By way of example, in some embodiments, the transfer device can be the collection device 500 described above with reference to FIGS. 28-35. As such, the transfer device can include a diversion mechanism with an inlet port configured to be selectively placed in fluid communication with the patient, a pre-sample reservoir and a sample reservoir, and a flow-metering mechanism configured to meter a flow of bodily-fluid from the patient to the pre-sample reservoir and to the sample reservoir. The method 690 includes establishing fluid communication between the patient and the port of the flow-metering transfer device, at 691. For example, the port can be fluidically coupled to a needle or other lumen-defining device (e.g., flexible sterile tubing), which in turn can be inserted into the patient (e.g., a venipuncture event or other method of accessing bodily-fluid).

With the port in fluid communication with the patient, fluid communication between the port and the pre-sample reservoir is established, at 692. In some embodiments, the flow-metering transfer device can include a flow controller or the like (e.g., such as the flow controller 540 included in the collection device 500) that can be actuated and/or manipulated (e.g., rotated) to a position that establishes fluid communication between the port and the pre-sample reservoir (e.g., a first position). In some embodiments, the actuating of the flow controller can be such that the flow controller and the diversion mechanism collectively define at least a portion of a fluid flow path between the port and the pre-sample reservoir. In some embodiments, the pre-sample reservoir can include a negative pressure or the like that can, for example, initiate a flow of bodily-fluid from the patient to the pre-sample reservoir. In other embodiments the flow of bodily-fluid can be initiated in any other suitable manner (e.g., gravity or the like).

The flow of bodily-fluid transferred from the patient to the pre-sample reservoir is metered, at 693. For example, in some embodiments, the port can include the flow control mechanism which can be meter a flow of bodily-fluid that passes through the port (e.g., in a similar manner as described above with reference to the flow metering mechanism 567 of the collection device 500). Thus, a pre-sample volume of bodily-fluid is transferred to the pre-sample reservoir. The method 690 includes verifying the pre-sample volume of bodily-fluid disposed in the pre-sample reservoir is a predetermined pre-sample volume of bodily-fluid via the flow metering mechanism of the flow-metering transfer device, at 694. For example, the flow metering mechanism can include and/or can be operably coupled to a display of the like (e.g., the display 575 and/or 575' of the collection device 500). The flow metering mechanism can be configured to present on the display volumetric information, as described above.

Once the pre-sample volume of bodily-fluid is disposed in the pre-sample reservoir, the pre-sample reservoir is fluidically isolated from the port to sequester the pre-sample volume of bodily-fluid in the pre-sample reservoir, at 695. For example, in some instances, the flow controller and/or the diversion mechanism can be actuated (or rotated) from the first position and/or configuration to a second position and/or configuration. With the flow controller and/or diversion mechanism in the second configuration, the pre-sample reservoir is fluidically isolated from a volume outside of the pre-sample reservoir. In some embodiments, when the flow controller and/or diversion mechanism is actuated to its second position and/or configuration, fluid communication is established between the port and a sample reservoir, at 696. For example, in some embodiments, the flow-metering transfer device can include a movable member (e.g., the movable member 550) or the like that can include a piercing member configured to pierce a portion of the sample reservoir (e.g., a septum or the like). Therefore, with the flow controller and/or diversion mechanism in its second position and/or configuration, the piercing of the portion of the sample reservoir places the sample reservoir in fluid communication with the port. As described above, the sample reservoir can include a negative pressure or the like that can, for example, initiate a flow of bodily-fluid from the patient to the sample reservoir.

The flow of bodily-fluid transferred from the patient to the pre-sample reservoir is metered, at 697. For example, as described above, the port can include the flow control mechanism which can be meter a flow of bodily-fluid that passes through the port (e.g., in a similar manner as described above with reference to the flow metering mechanism 567 of the collection device 500). In some embodiments, the flow control mechanism can be included in, for example, a movable member or the like such as the movable member 550 of FIG. 31. Thus, a sample volume of bodily-fluid is transferred to the sample reservoir. The method 690 includes verifying the sample volume of bodily-fluid disposed in the sample reservoir is a predetermined sample volume of bodily-fluid via the flow metering mechanism of the flow-metering transfer device, at 698. For example, the display or the like can be configured to present volumetric information, as described above.

In this manner, the predetermined pre-sample volume of bodily-fluid is collected that can contain, for example, externally residing microbes. For example, in some embodiments, the predetermined pre-sample volume can be about 0.1 mL, about 0.3 mL, about 0.5 mL, about 1.0 mL, about 2.0 mL, about 3.0 mL, about 4.0 mL, about 5.0 mL, about 10.0 mL, about 20 mL, about 50 mL, and/or any volume or fraction of a volume therebetween. In other embodiments, the pre-sample volume can be greater than 50 mL or less than 0.1. In other embodiments, the predetermined pre-sample volume can be between about 2 mL and about 5 mL. In still other embodiments, the predetermined pre-sample volume can be about 3 mL. Furthermore, by collecting the predetermined pre-sample volume, the predetermined sample volume disposed in one or more sample reservoirs can be substantially free-from externally residing microbes. In some embodiments, the predetermined sample volume can be between 10 mL and 60 mL. In other embodiments, the predetermined sample volume can be between 30 mL and 60 mL. In still other embodiments, the predetermined sample volume can be 60 mL. Although described above as transferring the sample volume of the bodily-fluid to a single sample reservoir, in other embodiments, the flow-metering transfer device can be used to transfer a predetermined sample volume to more than one sample reservoir. For example, in some embodiments, a pre-determined pre-sample volume of bodily-fluid can be collected and fluidically isolated in a pre-sample reservoir, as described above. With the pre-sample volume fluidically isolated, the flow-metering transfer device can be used to transfer a predetermined sample volume to a first sample reservoir, the predetermined sample volume to a second sample reservoir, and the predetermined sample volume to a third sample reservoir. In such instances, the predetermined sample volume can be, for example, 20 mL such that a total sample volume disposed in the first, second, and third sample reservoirs is 60 mL.

The various embodiments of the bodily-fluid collection devices described herein can allow the collection of two (or more) sets of bodily-fluids (e.g., blood) samples from a single venipuncture. The current standard of care dictates that certain tests (e.g. blood cultures) be conducted with samples procured from distinct, separate bodily-fluid access points (e.g. via two separate venipunctures, via a catheter+a venipuncture and/or any combination thereof). Embodiments described herein can facilitate the procurement of multiple samples for specific diagnostic testing (e.g. blood culture test) from a single bodily-fluid access point (e.g. venipuncture), which can reduce the annual number of venipunctures required for procurement of these samples by a factor of 2. This benefits both patients and health care practitioners alike. A reduction in the number of venipunctures (and/or other bodily-fluid access procedures) can significantly reduce the risk of needle stick injury to heath care practitioners and reduce patient associated complications which result from these procedures (e.g. hematoma, thrombosis, phlebitis, infection, etc.). Additionally, reducing the number of bodily-fluid access procedures (e.g. venipunctures) reduces the utilization of supplies, labor and waste associated with these procedures. The decreased costs realized by the healthcare system are material and represent an opportunity to drive more efficient consumption of resources as well as enhanced patient outcomes due to improved sample integrity which results in more accurate patient diagnoses which inform development and implementation of treatment plan(s). The bodily-fluid collection devices also significantly reduce the occurrence of false-positives from post-collection analysis. The bodily-fluid collection devices described herein can also streamline the bodily-fluid collection process and reduce the number of manual steps and "touch points", thereby decreasing opportunities for external contamination. The devices described herein can also minimize the risk for needle stick injuries and infection for the lab technicians and/or phlebotomists.

Figure 14:
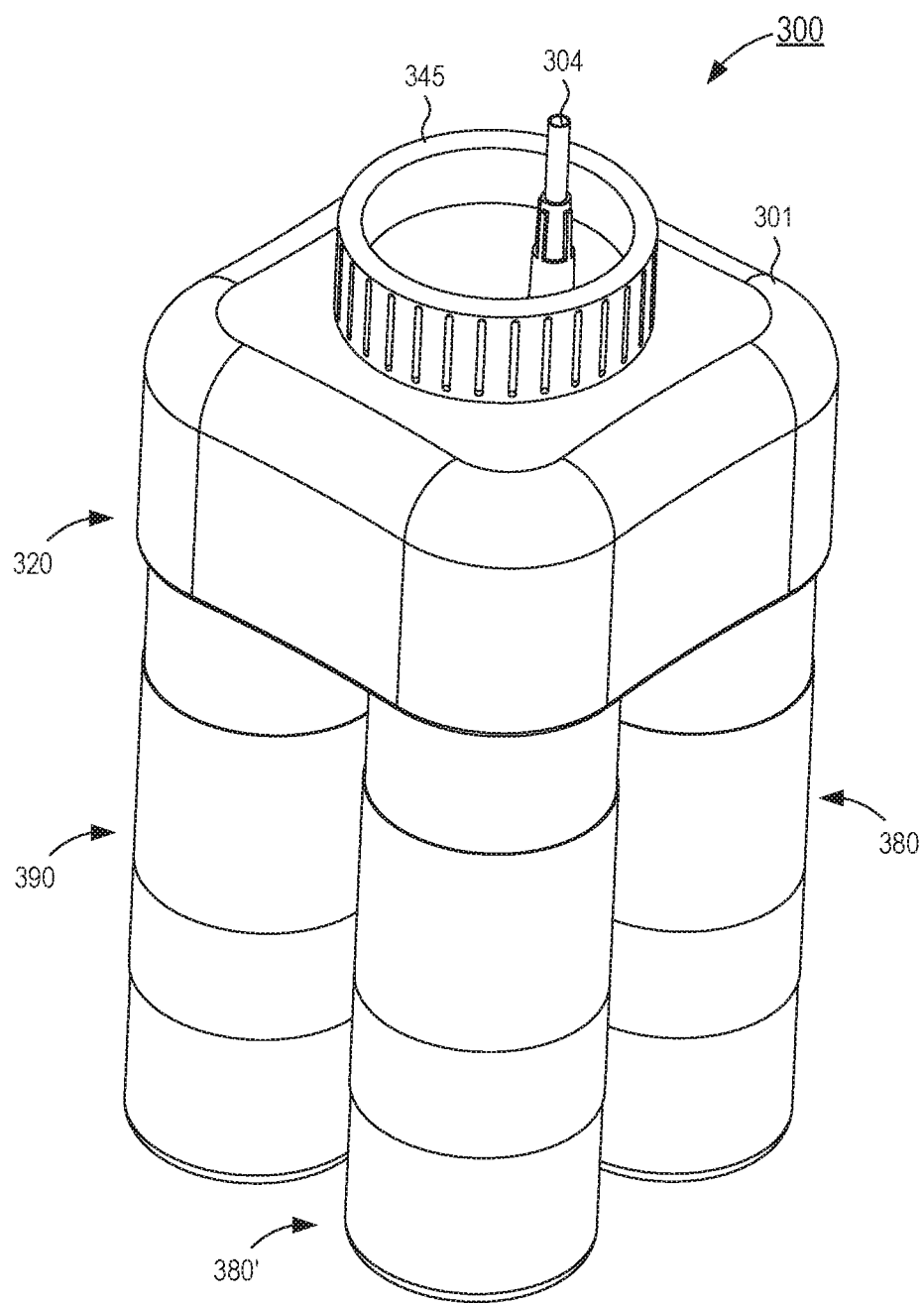
FIG. 14 is a perspective view of a bodily-fluid collection device according to an embodiment.

In some embodiments, the bodily-fluid collection devices described herein (e.g., 100, 200, 300, 400, and 500) can include and/or be partially formed from antisepsis saturated materials (e.g., housing 301). Current standards rely on health care practitioners placing individual antisepsis materials (e.g. isopropyl alcohol swabs) on the top of individual sample reservoirs (e.g., 380, 380', 390, and 390'). To ensure compliance with this protocol, the device 300 (for example) can include antisepsis materials positioned in the device 300 such that when the housing 301 is placed on top of the 4-pack (or 2-pack) of bottles as illustrated in FIG. 14, the first point of contact from the hosing 301 and the tops of the sample reservoirs 380, 380', 390, 390' is the antisepsis material. In this manner, the tops of the sample reservoirs 380, 380', 390, 390' are assured to have an appropriate antisepsis applied prior to inoculation of the bodily-fluid into the sample reservoirs.

While various embodiments have been particularly shown and described, various changes in form and details may be made. For example, while the dial 345 (actuator) is shown and described with respect to FIGS. 17-20 as being rotated in a single direction, in other embodiments, the dial 345 (actuator) can be rotated in a first direction and a second direction, opposite the first. In such embodiments, the rotation in the second direction can be configured to move a collection device through any number of configurations. In other embodiments, the rotation of the actuator in the second direction can be limited. In some embodiments, the dial can include a mechanical stop or lock to fluidically isolate the first volume of bodily-fluid received from the patient (i.e., the contaminated sample). Said another way, once the first reservoir (pre-sample reservoir) is filed with a predetermined volume of bodily-fluid and the user has rotated the dial (actuator) to begin drawing additional sample, the dial (actuator) cannot be moved back to establish fluid communication with the first sample volume (contained in the pre-sample reservoir).

While embodiments have been described above, it should be understood that they have been presented by way of example only, and not limitation. Although various embodiments have been described as having particular features and/or combinations of components, other embodiments are possible having any combination or sub-combination of any features and/or components from any of the embodiments described herein. For example, while the collection device 400 is shown and described with respect to FIGS. 21-27 as having a first, second, third, fourth, or fifth configuration, in other embodiments, the collection devices described herein may have more or fewer configurations. In addition, while the collection device 200 is shown and described with respect to in FIGS. 2-13 as having a vacuum based collection tube as the pre-sample reservoir 270, in other embodiments, the collection device 200 can have a chamber contained within the housing 201 similar to the collection device 300 of the embodiment presented in FIGS. 14-20, which includes a pre-sample reservoir 370 that is a chamber contained within the distribution member 329, and vice versa.

The specific configurations of the various components can also be varied. For example, the size and specific shape of the various components can be different from the embodiments shown, while still providing the functions as described herein. More specifically, the size and shape of the various components can be specifically selected for a desired rate of bodily-fluid flow into a fluid reservoir. Furthermore, while the flow metering mechanism 567 is particularly shown in FIG. 31, any of the collection devices described herein can be used with any suitable flow metering mechanism. For example, in some embodiments, a collection device can include a flow metering mechanism and/or any other mechanism, device, or method configured to measure volumetric characteristics of a bodily-fluid such as, for example, a pressure sensor, a voltage sensor, a photo sensor, a velocity sensor, a flow meter, a strain gauge, a valve, a turbine, a float, displacement analysis, density analysis, weight analysis, optical analysis, ultrasound analysis, thermal analysis, Doppler analysis, electromagnetic field (emf) analysis, reflection analysis, obstruction analysis, area analysis, venturi analysis, coriolis analysis, visual analysis, and/or any other suitable sensor, analysis, and/or calculation (e.g., applying and/or using, for example, Boyle's law, ideal gas law, force calculation (force=mass*acceleration), and/or the like).

What is claimed:

1. An apparatus for obtaining a bodily-fluid sample from a patient, the apparatus comprising:
   a distribution member forming at least a portion of a pre-sample reservoir and defining a fluid flow path in fluid communication with an outlet; and
   a flow controller in fluid communication with the distribution member and configured to be placed in fluid communication with the patient,
   the flow controller having a first configuration in which the flow controller is in fluid communication with the pre-sample reservoir to transfer a first volume of bodily-fluid from the patient toward the pre-sample reservoir,
   the flow controller configured to transition from the first configuration to a second configuration after the first volume of bodily-fluid flows into the pre-sample reservoir to:
      sequester the first volume of bodily-fluid in the pre-sample reservoir, and
      transfer a second volume of bodily-fluid to the fluid flow path such that potential contaminants are included in the sequestered volume of bodily-fluid while the second volume of bodily-fluid is substantially free from contaminants,
   the distribution member configured to be coupled to a sample reservoir after the second volume of bodily-fluid is transferred into the fluid flow path, the outlet configured to place the fluid flow path in fluid communication with the sample reservoir when the distribution member is coupled to the sample reservoir to transfer a sample volume of bodily-fluid from the fluid flow path into the sample reservoir.

2. The apparatus of claim 1, wherein the first volume of bodily-fluid is between 0.1 milliliters and 10 milliliters.

3. The apparatus of claim 1, wherein the second volume of bodily-fluid is between 2.5 milliliters and 60 milliliters.

4. The apparatus of claim 1, wherein the fluid flow path is a first fluid flow path, the outlet is a first outlet, and the sample reservoir is a first sample reservoir, the distribution member defines a second fluid flow path in fluid communication with a second outlet,
   the flow controller is configured to be transitioned to a third configuration to transfer a third volume of bodily-fluid to the second fluid flow path after the first volume of bodily-fluid is sequestered in the pre-sample reservoir,
   the distribution member is configured to be coupled to a second sample reservoir after the third volume of bodily-fluid is transferred into the second fluid flow path, the second outlet configured to place the second fluid flow path in fluid communication with the second sample reservoir when the distribution member is coupled to the second sample reservoir to transfer a sample volume of bodily-fluid from the second fluid flow path into the second sample reservoir.

5. The apparatus of claim 1, wherein the flow controller is configured to limit movement from the second configuration toward the first configuration.

6. An apparatus for obtaining a bodily-fluid sample from a patient, the apparatus comprising:
   a housing;

a distribution member disposed within the housing, the distribution member forming at least a portion of a pre-sample reservoir and defining a fluid flow path in fluid communication with an outlet; and a flow controller in fluid communication with the housing and including an inlet configured to be placed in fluid communication with the patient, the flow controller having a first configuration in which the inlet is in fluid communication with the pre-sample reservoir to transfer a first volume of bodily-fluid from the inlet toward the pre-sample reservoir, the flow controller configured to be transitioned from the first configuration to a second configuration to transfer a second volume of bodily-fluid to the fluid flow path after the first volume of bodily-fluid flows into the pre-sample reservoir, the first volume of bodily-fluid including potential contaminants and the second volume of bodily-fluid being substantially free from contaminants, the distribution member configured to be coupled to a sample reservoir after the second volume of bodily-fluid is transferred into the fluid flow path, the outlet configured to place the fluid flow path in fluid communication with the sample reservoir when the distribution member is coupled to the sample reservoir to transfer a sample volume of bodily-fluid from the fluid flow path into the sample reservoir.

7. The apparatus of claim 6, wherein the flow controller is configured to sequester the first volume of bodily-fluid in the pre-sample reservoir when the flow controller is in the second configuration.

8. The apparatus of claim 6, wherein the second volume is between 2.5 milliliters and 60 milliliters.

9. The apparatus of claim 6, wherein the fluid flow path is a first fluid flow path, the outlet is a first outlet, and the sample reservoir is a first sample reservoir, the distribution member defines a second fluid flow path in fluid communication with a second outlet, the flow controller is configured to be transitioned from the second configuration to a third configuration to transfer a third volume of bodily-fluid to the second fluid flow path after the second volume of bodily-fluid is transferred into the first fluid flow path, the distribution member is configured to be coupled to a second sample reservoir after the third volume of bodily-fluid is transferred into the second fluid flow path, the second outlet configured to place the second fluid flow path in fluid communication with the second sample reservoir when the distribution member is coupled to the second sample reservoir to transfer a sample volume of bodily-fluid from the second fluid flow path into the second sample reservoir.

10. The apparatus of claim 9, wherein the first sample reservoir and the second sample reservoir are included in a pack such that the distribution member is coupled to the first sample reservoir and the second sample reservoir substantially concurrently.

11. The apparatus of claim 10, wherein the sample volume transferred to each of first sample reservoir and the second sample reservoir is between 2.5 milliliters and 10 milliliters.

12. An apparatus for obtaining a bodily-fluid sample from a patient, the apparatus comprising:

a distribution member forming at least a portion of a pre-sample reservoir, the distribution member defining a fluid flow path in fluid communication with a coupling portion, the coupling portion configured to be coupled to a sample reservoir; and a flow controller coupled to the distribution member and including an inlet configured to receive bodily-fluids from the patient, the flow controller having a first configuration in which the inlet is placed in fluid communication with the pre-sample reservoir to transfer a first volume of bodily-fluid withdrawn from the patient toward the pre-sample reservoir, the flow controller configured to be transitioned from the first configuration to a second configuration after the first volume of bodily-fluid flows into the pre-sample reservoir to:

sequester the first volume of bodily-fluid in the pre-sample reservoir, and transfer a second volume of bodily-fluid into the fluid flow path such that potential contaminants are included in the sequestered volume of bodily-fluid while the second volume of bodily-fluid is substantially free from contaminants, the coupling portion configured to be coupled to the sample reservoir after the second volume of bodily-fluid is transferred into the fluid flow path to transfer at least a portion of the second volume of bodily-fluid to the sample reservoir.

13. The apparatus of claim 12, wherein at least the portion of the second volume of bodily-fluid is a sample volume of bodily-fluid between about 2.5 milliliters and about 60 milliliters.

14. The apparatus of claim 12, wherein the sample reservoir includes at least one of an aerobic culture media or an anaerobic culture media.

15. The apparatus of claim 12, wherein the sample reservoir is a first sample reservoir and the portion of the second volume of bodily-fluid is a first portion of the second volume of bodily-fluid, the coupling portion of the distribution member is configured to be physically and fluidically coupled to a second sample reservoir configured to receive a second portion of the second volume of bodily-fluid.

16. The apparatus of claim 15, wherein the first sample reservoir and the second sample reservoir are configured to receive, substantially concurrently, the first portion of the second volume of bodily-fluid and the second portion of the second volume of bodily-fluid, respectively.

17. The apparatus of claim 15, wherein the first sample reservoir includes at least one of an aerobic culture media or an anaerobic culture media and the second sample reservoir includes at least one of an aerobic culture media or an anaerobic culture media.

\* \* \* \* \*